(12) United States Patent
Koenig et al.

(10) Patent No.: US 7,425,620 B2
(45) Date of Patent: Sep. 16, 2008

(54) FCγRIIB-SPECIFIC ANTIBODIES AND METHODS OF USE THEREOF

(76) Inventors: Scott Koenig, 10901 Ralston Rd., Rockville, MD (US) 20852; Maria Concetta Veri, 7715 Goodfellow Way, Derwood, MD (US) 20855

( * ) Notice: Subject to any disclaimer, the term of this patent is extended or adjusted under 35 U.S.C. 154(b) by 479 days.

(21) Appl. No.: 10/643,857

(22) Filed: Aug. 14, 2003

(65) Prior Publication Data
US 2004/0185045 A1  Sep. 23, 2004

Related U.S. Application Data

(60) Provisional application No. 60/403,266, filed on Aug. 14, 2002.

(51) Int. Cl.
C07K 16/00 (2006.01)
C12P 21/08 (2006.01)
A61K 39/395 (2006.01)
C07K 1/00 (2006.01)

(52) U.S. Cl. ............... 530/387.1; 530/387.3; 530/388.1; 530/388.2; 530/391.1; 424/130.1; 424/133.1; 424/134.1; 424/136.1

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 5,648,260 A | 7/1997 | Winter et al. | |
| 5,711,944 A | 1/1998 | Gilbert et al. | |
| 5,837,243 A | 11/1998 | Deo et al. | |
| 5,888,533 A | 3/1999 | Dunn | |
| 5,945,115 A | 8/1999 | Dunn et al. | |
| 6,019,968 A | 2/2000 | Platz et al. | |
| 6,132,764 A | 10/2000 | Li et al. | |
| 6,194,551 B1 | 2/2001 | Idusogie et al. | |
| 6,218,149 B1 | 4/2001 | Morrison et al. | |
| 6,339,069 B1 | 1/2002 | Meers et al. | |
| 6,420,149 B1 | 7/2002 | Fukuda et al. | |
| 6,472,511 B1 | 10/2002 | Leung et al. | |
| 6,528,624 B1 | 3/2003 | Idusogie et al. | |
| 6,737,056 B1 | 5/2004 | Presta | |
| 2001/0036459 A1 | 11/2001 | Ravetch | |
| 2002/0028486 A1 | 3/2002 | Morrison et al. | |
| 2003/0115614 A1 | 6/2003 | Kanda et al. | |
| 2004/0002587 A1 | 1/2004 | Watkins et al. | |
| 2004/0185045 A1 | 9/2004 | Koenig et al. | |
| 2005/0037000 A1 | 2/2005 | Stavenhagen et al. | |
| 2005/0064514 A1* | 3/2005 | Stavenhagen et al. | 435/7.1 |
| 2005/0215767 A1 | 9/2005 | Koenig et al. | |
| 2005/0260213 A1 | 11/2005 | Koenig et al. | |
| 2006/0013810 A1 | 1/2006 | Johnson et al. | |
| 2006/0073142 A1 | 4/2006 | Chan et al. | |
| 2006/0177439 A1 | 8/2006 | Koenig et al. | |
| 2007/0253948 A1 | 11/2007 | Chan et al. | |

FOREIGN PATENT DOCUMENTS

| | | |
|---|---|---|
| EP | 0 332 865 | 9/1989 |
| EP | 0 629 703 | 12/1994 |
| EP | 0 359 096 | 11/1997 |
| EP | 0 953 639 | 11/1999 |
| EP | 1 006 183 A1 | 6/2000 |
| EP | 0 343 950 B1 | 10/2000 |
| WO | WO 94/18330 | 8/1994 |
| WO | WO 99/19362 | 4/1999 |
| WO | WO 99/41285 | 8/1999 |
| WO | WO 99/58572 A1 | 11/1999 |
| WO | WO 00/42072 | 7/2000 |
| WO | WO 01/79299 A1 | 10/2001 |
| WO | WO 03/035835 | 5/2003 |
| WO | WO 03/066095 A2 | 8/2003 |
| WO | WO 2004/016750 A2 | 2/2004 |
| WO | WO 2005/110474 A2 | 11/2005 |
| WO | WO 2005/115452 A2 | 12/2005 |
| WO | WO 2006/066078 A2 | 6/2006 |
| WO | PCT/US2007/072151 | 6/2007 |

OTHER PUBLICATIONS

Pluckthun et al. Immunotechnology 1997, 3:83-105.*
Abra et al. The next generation of liposome delivery systems: recent experience with tumor-targeted, sterically-stabilized immunoliposomes and active-loading gradients. J Liposome Res. Feb.-May 2002;12(1-2):1-3.
Bendas G, Immunoliposomes: a promising approach to targeting cancer therapy. BioDrugs. 2001;15(4):215-24.
Billadeau et al., ITAMs versus ITIMs: striking a balance during cell regulation, J Clin Invest. Jan. 2002;109(2):161-8.
Bolland and Ravetch. Inhibitory pathways triggered by ITIM-containing receptors. Adv Immunol. 1999;72:149-177.
Bolland et al. Genetic modifiers of systemic lupus erythematosus in FcgammaRIIB(-/-) mice. J Exp Med. May 6, 2002;195(9):1167-74.
Brauweiler et al., Partially Distinct Molecular Mechanisms Mediate Inhibitory FcγRIIB Signaling In Resting and Activated B Cells, Journal of Immunology, 2001, 167: 204-211.
Brown EJ. In vitro assays of phagocytic function of human peripheral blood leukocytes: receptor modulation and signal transduction. Methods Cell Biol. 1994;45:147-164.

(Continued)

Primary Examiner—Maher M. Haddad
Assistant Examiner—Chun Dahle
(74) Attorney, Agent, or Firm—Jeffrey I. Auerbach; June E. Cohan; Edell, Shapiro & Finnan, LLC

(57) ABSTRACT

The present invention relates to antibodies or fragments thereof that specifically bind FcγRIIB, particularly human FcγRIIB, with greater affinity than said antibodies or fragments thereof bind FcγRIIA, particularly human FcγRIIA. The invention provides methods of enhancing the therapeutic effect of therapeutic antibodies by administering the antibodies of the invention to enhance the effector function of the therapeutic antibodies. The invention also provides methods of enhancing efficacy of a vaccine composition by administering the antibodies of the invention.

15 Claims, 29 Drawing Sheets

OTHER PUBLICATIONS

Figure 1A:
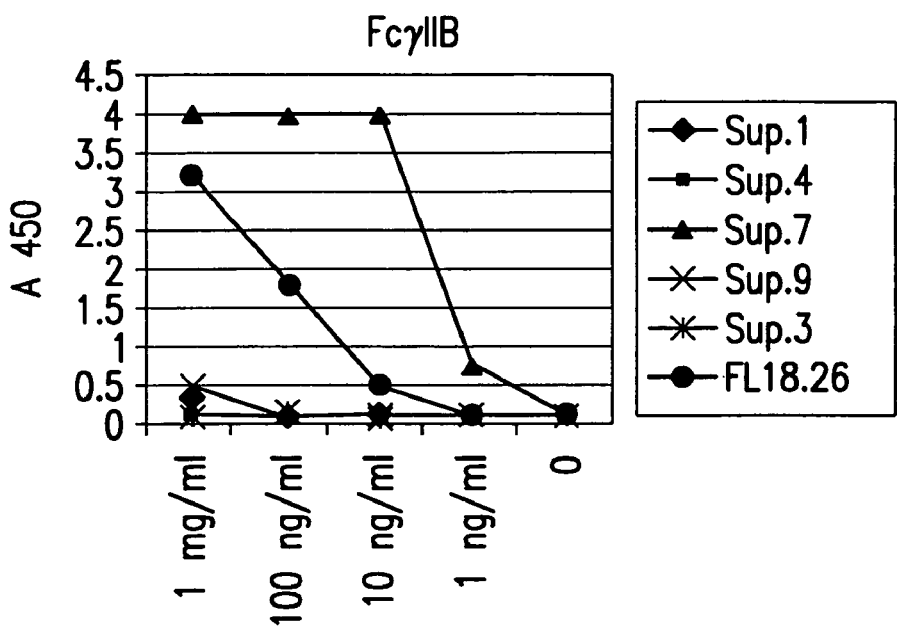

Budde et al., Specificity of CD32 mAB for FcγRIIa, FcγRIIb1, and FcγRIIb2 expressed in transfected mouse B cells and BHK-21 cells, *Leukocyte Typing V: White Cell Differentiation Antigens*. 1995, 828-832. (Schlossman, Boumsell, Gilks, Harlan, Kishomoto, eds.).

Callanan et al., The IgG Fc Receptor, FcγRIIB is a target for deregulation by chromosomal translocation in malignant lymphoma, PNAS, Jan. 2000 97(1): 309-314.

Cameron et al.. Differentiation of the human monocyte cell line, U937, with dibutyryl cyclicAMP induces the expression of the inhibitory Fc receptor, FcgammaRIIb. Immunol Lett. Oct. 1, 2002;83(3):171-9.

Camilleri-Broët et al., FcgammaRIIB is differentially expressed during B cell maturation and in B-cell lymphomas. British Journal of Haematology, 2004; 124:55-62.

Cassard et al., Modulation of tumor growth by inhibitory Fcgamma receptor expressed by human melanoma cells. The Journal of Clinical Investigation, Nov. 2002; 110(10):1549-1557.

Chappel et al., Identification of the FCgamma receptor class I binding site in human IgG through the use of recombinant IgG1/IgG2 hybrid and point-mutated antibodies. Proc. Natl. Acad. Sci., USA, Oct. 1991; 88(20):9036-9040.

Clynes et al. Inhibitory Fc receptors modulate in vivo cytoxicity against tumor targets. Nat Med 2000 6(4): 443-6.

Damle et al., B-cell chronic lymphocytic leukemia cells express a surface membrane phenotype of activated, antigen-experienced B lymphocytes. Blood Jun. 1, 2002; 99(11):4087-4093.

Davies et al. Expression of GnTIII in a recombinant anti-CD20 CHO production cell line: Expression of antibodies with altered glycoforms leads to an increase in ADCC through higher affinity for FC gamma RIII. Biotechnol Bioeng. Aug. 20, 2001;74(4):288-94.

Daëron et al., The Same Tyrosine Based Inhibition Motif, in the Intracytoplasmic Domain of FcγRIIB, regulates Negatively BCR, TCR- and FcR dependent Cell Activation, Immunity, Nov. 3, 1995: 635-646.

Eppstein et al. Biological activity of liposome-encapsulated murine interferon gamma is mediated by a cell membrane receptor. Proc Natl Acad Sci U S A. Jun. 1985;82(11):3688-92.

Fanger et al., Production and Use of Anti-FcR Bispecific Antibodies, Immunomethods 1994, 4: 72-81.

Farag, et al. FcγRIIIa and FcγRIIIa Polymorphisms Do Not Predict Response to Rituximab in B-Cell Chronic Lymphocytic Leukemia. Blood. Oct. 16, 2003.

Fidler, I. J. (1985). "Macrophages and metastasis—a biological approach to cancer therapy." Cancer Res 45(10): 4714-26.

Gerber et al., Stimulatory and inhibitory signals originating from the macrophage Fcgamma receptors, Microbes Infect. Feb. 2001;3(2):131-9.

Holmes et al. Alleles of the Ly-17 alloantigen define polymorphisms of the murine IgG Fc receptor. Proc Natl Acad Sci U S A Nov. 1985;82(22):7706-10.

Hwang et al. Hepatic uptake and degradation of unilamellar sphingomyelin/cholesterol liposomes: a kinetic study. Proc Natl Acad Sci U S A. Jul. 1980;77(7):4030-4.

Isaacs et al., Therapy with monoclonal antibodies. II. The contribution of Fcgamma receptor binding and the influence of $C_H1$ and $C_H3$ domains on in vivo effector function. The Journal of Immunology, 1998; 161:3862-3869.

Jefferis et al. Recognition sites on human IgG for Fc gamma receptors: the role of glycosylation. Immunol Lett Jan. 1995;44(2-3):111-7.

Kagari et al., Essential Role of Fcgamma Receptors in anti-type II collagen antibody induced arthritis, J. Immunol. Apr. 2003 170: 4318-24.

Lifely et al. Glycosylation and biological activity of CAMPATH-1H expressed in different cell lines and grown under different culture conditions. Glycobiology. Dec. 1995;5(8):813-22.

Lin et al. Colony-stimulating factor 1 promotes progression of mammary tumors to malignancy. J Exp Med. 2001 193(6): 727-739.

Lin et al.. The macropage growth factor CSF-1 in mammary gland development and tumor progression. J Mammary Gland Biol Neoplasia 2002 7(2): 147-62.

Lyden et al. The Fc receptor for IgG expressed in the villus endothelium of human placenta is Fc gamma RIIb2. J Immunol Mar. 15, 2001;166(6):3882-9.

Malbec et al., Fcε Receptor I-Associated *lyn*-Dependent Phosphorylation of Fcγ Receptor IIB During Negative Regulation of Mast Cell Activation. J. of Immunology, 1998, 160: 1647-58.

Maruyama K. In vivo targeting by liposomes. Biol Pharm Bull. Jul. 2000;23(7):791-9.

Metcalfe, Mast Cells, Physiol Rev. Oct. 1997;77(4):1033-79.

Micklem et al., Different Isoforms of Human FcRII Distinguished by CDw32 Antibodies, Journal of Immunology, Mar. 1990, 144:2295-2303.

Nakamura et al., Fcgamma receptor IIB-deficient mice develop Goodpasture's Syndrome upon immunization with Type IV collagen: a novel murine model for Autoimmune Glomerular Basement Membrane Disease. J. Exp. Med. Mar. 6, 2000; 191(5):899-905.

Norris et al., A naturally occurring mutation in FcgammaRIIA: A Q to $K^{127}$ change confers unique IgG binding properties to the $R^{131}$ allelic form of the receptor, Blood Jan. 15, 1998; 91(2):656-662.

Ott et al., Downstream of Kinase, p62dok, Is a Mediator of FcγRIIB Inhibition of FcεRI Signaling, J. of Immunology, 2002, 168: 4430-9.

Park et al. Immunoliposomes for cancer treatment. Adv Pharmacol. 1997;40:399-435.

Park YS. Tumor-directed targeting of liposomes. Biosci Rep. Apr. 2002;22(2):267-81.

Presta LG. Engineering antibodies for therapy. Curr Pharm Biotechnol. Sep. 2002;3(3):237-56.

Pricop et al. Differential modulation of stimulatory and inhibitory Fc gamma receptors on human monocytes by Th1 and Th2 cytokines. J Immunol. Jan. 1, 2001;166(1):531-7.

Pulford et al. A new monoclonal antibody (KB61) recognizing a novel antigen which is selectively expressed on a subpopulation of human B lymphocytes. Immunology. Jan. 1986;57(1):71-6.

Qin et al., Fcgamma receptor IIB on follicular dendritic cells regulates the B cell recall response. The Journal of Immunology. 2000; 164:6268-6275.

Ravetch and Bolland IgG Fc receptors. Annu Rev Immunol. 2001;19:275-290. Review.

Ravetch et al., Fc Receptors, Annu Rev Immunol. 1991;9:457-92.

Ravetch et al., Fc receptors: rubor redux. Cell. Aug. 26, 1994;78(4):553-60.

Ravetch et al., Immune inhibitory receptors Science. Oct. 6, 2000;290(5489):84-9.

Reali et al. IgEs targeted on tumor cells: therapeutic activity and potential in the design of tumor vaccines. Cancer Res 2001 61(14): 5517-22.

Routledge et al. The effect of aglycosylation on the immunogenicity of a humanized therapeutic CD3 monoclonal antibody. Transplantation. Oct. 27, 1995;60(8):847-53.

Samuelsson et al., Anti-inflammatory activity of IVIG mediated through the inhibitory Fc receptor. Science, Jan. 19, 2001; 291:484-486.

Sarkar et al., Negative signaling via FcgammaRIIB1 in B cells blocks phospholipase Cgamma2 tyrosine phosphorylation but not Syk or Lyn activation. The Journal of Biological Chemistry, Aug. 16, 1996; 271(33):20182-20186.

Scholl et al.. Is colony-stimulating factor-1 a key mediator of breast cancer invasion and metastasis? Mol Carcinog 7(4): 207-11.

Shields et al. Lack of fucose on human IgG1 N-linked oligosaccharide improves binding to human Fcgamma RIII and antibody-dependent cellular toxicity. J Biol Chem. Jul. 26, 2002;277(30):26733-40.

Sondermann et al. The 3.2-Å crystal structure of the human IgG1 Fc fragment-Fc gammaRIII complex. Nature. Jul. 20, 2000;406(6793):267-273.

Tam et al., A bispecific antibody against human IgE and human FcgammaRII that inhibits antigen-induced histamine release by human mast cells and basophils. Allergy 2004; 59:772-780.

Tao and Morrison, Studies of aglycosylated chimeric mouse-human IgG. Role of carbohydrate in the structure and effector functions mediated by the human IgG constant region. J Immunol. Oct. 15, 1989;143(8):2595-601.

Todorovska et al. Design and application of diabodies, triabodies and tetrabodies for cancer targeting. J Immunol Methods. Feb. 1, 2001;248(1-2):47-66. Review.

Tridandapani et al., Regulated Expression and Inhibitory Function of FcγRIIb in Human Monocytic Cells, Journal of Biol. Chem. 277(7): 50582-9.

Umana et al. Engineered glycoforms of an antineuroblastoma IgG1 with optimized antibody-dependent cellular cytotoxic activity. Nat Biotechnol. Feb. 1999;17(2):176-80.

Van Nguyen et al. Colony stimulating factor-1 is required to recruit macrophages into the mammary gland to facilitate mammary ductal outgrowth. Dev Biol 2002 247(1): 11-25.

Van Sorge et al. FcγR polymorphisms: Implications for function, disease susceptibility and immunotherapy. Tissue Antigens 2003, 61:189-202.

Vingerhoeds et al. Immunoliposomes in vivo. Immunomethods. Jun. 1994;4(3):259-72.

Wallick et al. Glycosylation of a VH residue of a monoclonal antibody against alpha (1-6) dextran increases its affinity for antigen. J Exp Med Sep. 1, 1988;168(3):1099-109.

Warmerdam et al. Molecular basis for a polymorphism of human Fc gamma receptor II (CD32). J Exp Med. Jul. 1, 1990;172(1):19-25.

Weinrich, V. Epitope mapping of new monoclonal antibodies recognizing distinct human FcRII (CD32) isoforms. Hybridoma Nov. 2, 1996; vol. 15:109-116.

Wright and Morrison, Effect of glycosylation on antibody function: implications for genetic engineering. Trends Biotechnol. Jan. 1997;15(1):26-32.

Xu et al., FcgRs Modulate Cytotoxicity of Anti-Fas Antibodies: Implications for Agonistic Antibody Based Therapeutics, Journal of Immunol. 2003, 171: 562-68.

Xu et al., Residue at position 331 in the IgG1 and IgG4 $C_H 2$ domains contributes to their differential ability to bind and activate complement. The Journal of Biological Chemistry, Feb. 4, 1994; 269(5):3469-3474.

*Petition to the Comissioner Regarding Interruption in Postal Service on* Aug. 14 and 15, 2003 with Exhibits A and B filed in the U.S. Patent and Trademark Office as Receiving Office on Oct. 28, 2003.

*Decision on Petition* of the U.S. Patent and Trademark Office dated Feb. 12, 2004.

*Renewed Petition Under 37 C.F.R. § 1.6(e)* with Declaration of Margaret B. Brivanlou and Exhibits A and B filed in the U.S. Patent and Trademark Office as Receiving Office on Apr. 12, 2004.

*Decision on Renewed Petition Under 37 C.F.R. 1.6* of the U.S. Patent and Trademark Office dated May 13, 2004.

*Renewed Petition Under 37 C.F.R. § 1.6(e)* with Exhibits A-C filed in the U.S. Patent and Trademark Office as Receiving Office on Nov. 15, 2004.

*Decision on Renewed Petition* with Attachments 1 and 2 of the U.S. Patent and Trademark Office dated May 10, 2005.

Ding et al., Inhibition of the function of the FcγRIIB by a monoclonal antibody to thymic shared antigen-1, a Ly-6 family antigen. Immunology. Sep. 2001;104(1):28-36.

U.S. Appl. No. 11/754,015, filed May 25, 2007, Johnson et al.

U.S. Appl. No. 11/768,852, filed Jun. 26, 2007, Johnson et al.

Bewarder et al., In vivo and in vitro specificity of protein tyrosine kinases for immunoglobulin G receptor (FcgammaRII) phosphorylation, Mol Cell Biol . 1996; 16(9):4735-43.

Boruchov et al., Activating and inhibitory IgG Fc receptors on human DCs mediate opposing functions. The Journal of Clinical Investigation 115; 10:2914-2923.

Fleit et al., Cross-linking of mAb to FcγRIIB results in tyrosine phosphorlyation of multiple polypeptides including FcγRIIB itself. Leukocyte Typing V: White cell differentiation antigens (Schlossman, Boumsell, Gilks, Harlan, Kishomoto, eds.) 1995; 826-827.

Gamberale et al. To the editor: Expression of Fcγ receptors type II (FcγRII) in chronic lymphocytic leukemia B cells, Blood (Correspondence), 2003; 102(7):2698-2699.

Kurlander et al. Comparison of intravenous gamma globulin and a monoclonal anti-Fc receptor antibody as inhibitors of immune clearance in vivo in mice. J Clin Invest. 1986; 77(6):2010-18.

Looney et al. Human Monocytes and U937 cells bear two distinct Fc receptors for IgG. J Immunol. 1986; 136(5):1641-47.

Maresco et al. The SH2-Containing 5'-inositol phosphate (SHIP) is tyrosine phosphorylated after Fcγ receptor clustering in monocytes. J Immunol. 1999; 162:6458-65.

Ott et al. FcγRIIB as a potential molecular target for intravenous gamma globulin therapy. J Allergy Clin Immunol. 2001; 108:S95-S98.

Pardridge et al., Blood-brain barrier drug targeting: The future of brain drug development. Molecular Interventions. 2003, 3;2:90-105. See particularly pp. 91-96.

Pulford et al. The immunocytochemical distribution of CD16, CD32, and CD64 antigens. Leukocyte Typing V: White Cell Differentiation antigens (Schlossman, Boumsell, Gliks, Harlan, Kishomoto, eds.). 1995;817-821.

Reff et al. A review of modifications to recombinant antibodies: attempt to increase efficacy in oncology applications. Crit Rev Oncol Hematol. 2001; 40(1):25-35.

Schuna et al. New Drugs for the treatment of rheumatoid arthritis. Am J Health Syst Phar. 2000; 57:225-37.

Su et al., Expression profile of FcγRIIB on leukocytes and its dysregulation in systemic lupus erythematosus. J. Immunol. 178:3272-3280, 2007.

Van de Winkel et al. CD32 cluster workshop report. Leukocyte Typing V: White Cell Differentiation Antigens (Schlossman, Boumsell, Gliks, Harlan, Kishomoto, eds.). 1995;823-25.

Vely et al. A new set of monoclonal antibodies against human Fc gamma RII (CD32) and Fc gamma RIII (CD16): characterization and use in various assays. Hybridoma. 1997; 16(6):519-28.

Zola et al. CD32 (FcgammaRII). J Biol Rgul Homeost Agents. 2000; 14(4):311-16.

Boruchov et al., Expression and Modulation of the Inhibitory Fcγ Receptor (CD32b) on Human Dendritic Cells (DCs). presented at , American Society of Hematology 45th Annual Meeting and Exposition, Dec. 7, 2003.

* cited by examiner

Figure 10B:
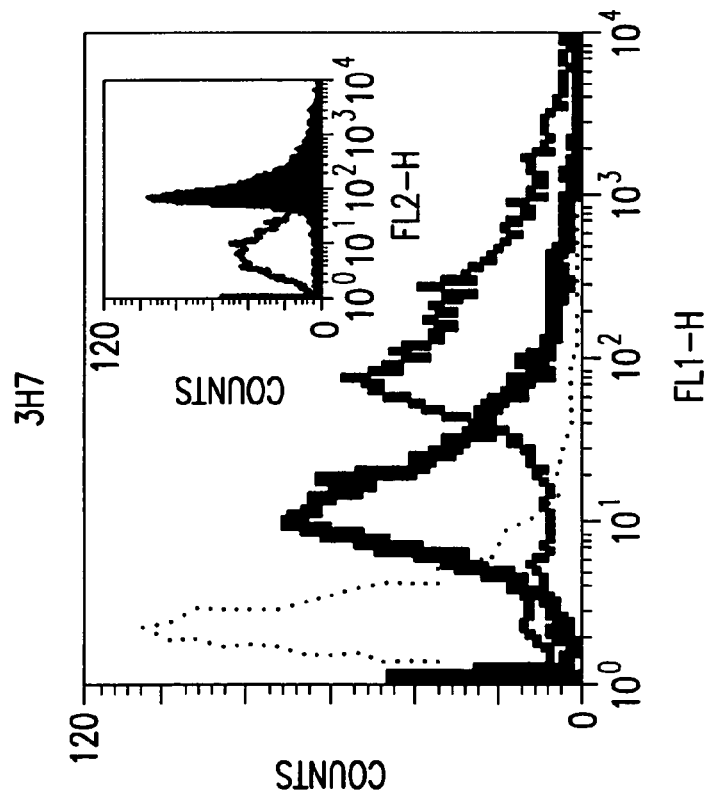
Figure 10A:
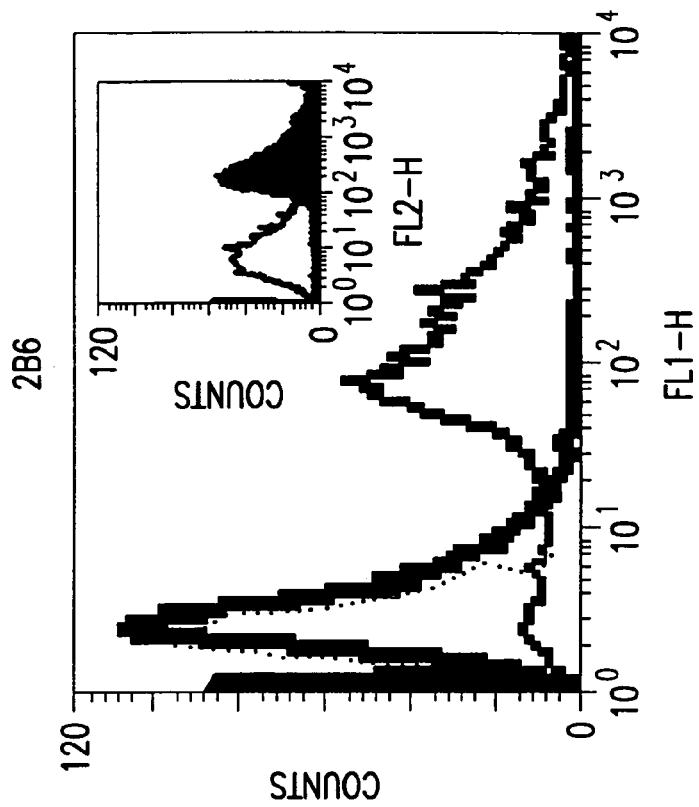
Figure 10D:
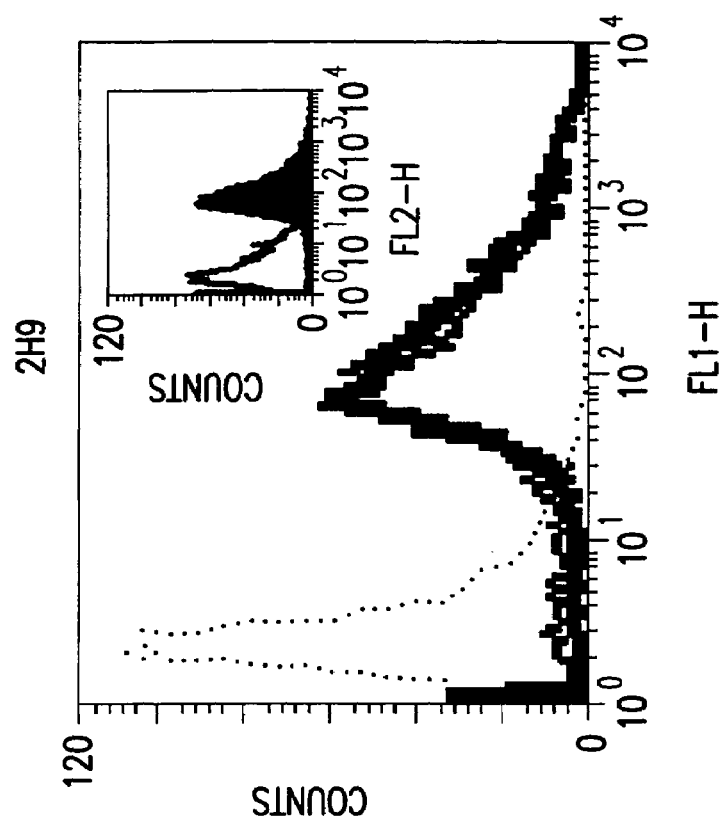
Figure 10C:
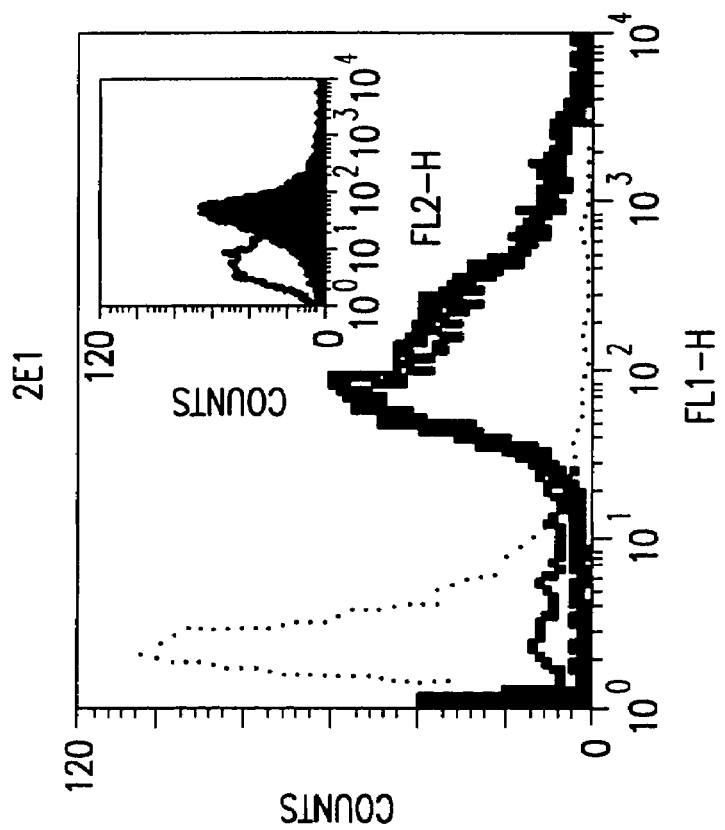

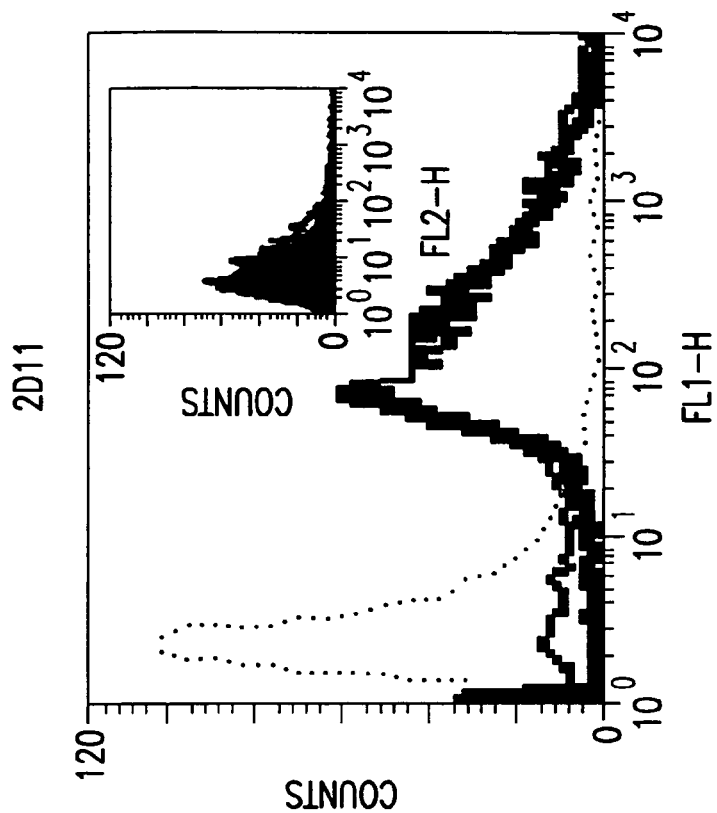
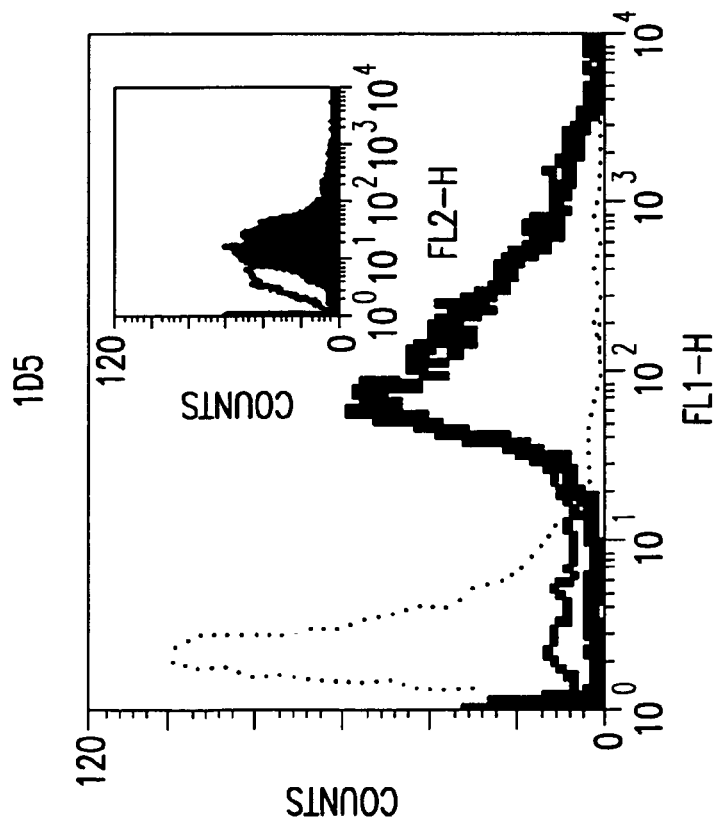
FIG. 10E
FIG. 10F

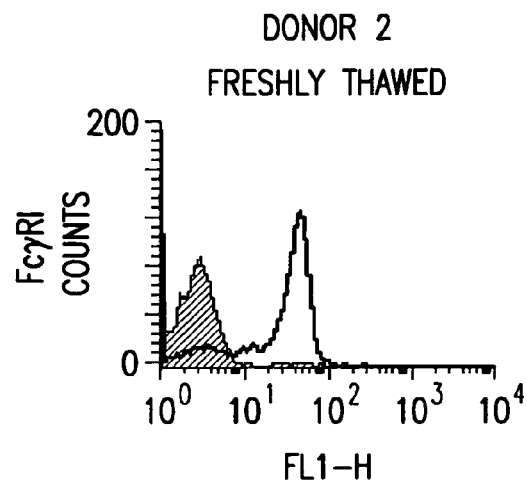
FIG.14Q
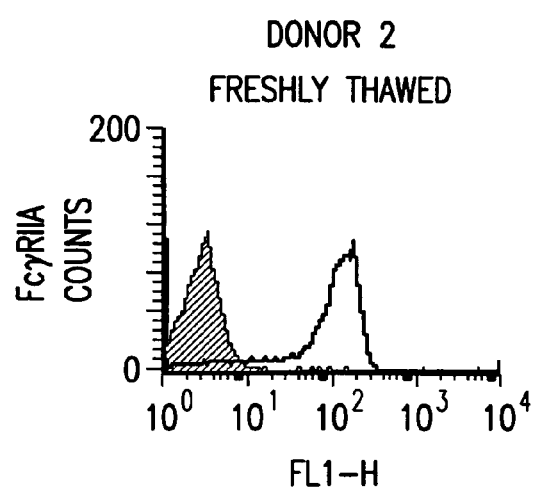
FIG.14-R
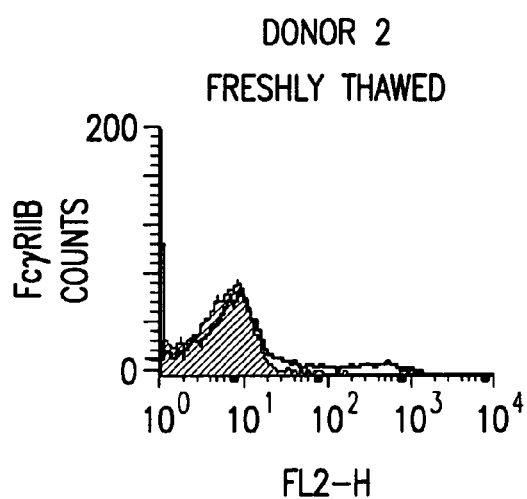
FIG.14-S
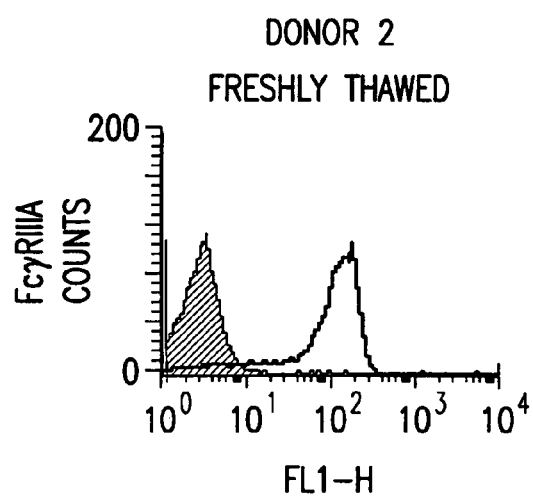
FIG.14-T phate 5'-phosphatase (SHIP), which hydrolyzes phosphoi-
FCγRIIB-SPECIFIC ANTIBODIES AND METHODS OF USE THEREOF This application claims priority to U.S. Provisional Application Ser. No. 60/403,266 filed on Aug. 14, 2002, which is incorporated herein by reference in its entirety.

1. FIELD OF THE INVENTION

The present invention relates to antibodies or fragments thereof that specifically bind FcγRIIB, particularly human FcγRIIB, with greater affinity than said antibodies or fragments thereof bind FcγRIIA, particularly human FcγRIIA. The invention provides methods of enhancing the therapeutic effect of therapeutic antibodies by administering the antibodies of the invention to enhance the effector function of the therapeutic antibodies. The invention also provides methods of enhancing efficacy of a vaccine composition by administering the antibodies of the invention.

2. BACKGROUND OF THE INVENTION

2.1 Fc Receptors and their Roles in the Immune System

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the a chain of the Fc receptor. Fc receptors are defined by their specificity for immunoglobulin subtypes. Fc receptors for IgG are referred to as FcγR, for IgE as FcεR, and for IgA as FcaR. Different accessory cells bear Fc receptors for antibodies of different isotype, and the isotype of the antibody determines which accessory cells will be engaged in a given response (reviewed by Ravetch J. V. et al. 1991, *Annu. Rev. Immunol.* 9: 457-92; Gerber J. S. et al. 2001 *Microbes and Infection*, 3: 131-139; Billadeau D. D. et al 2002, *The Journal of Clinical Investigation*, 2(109): 161-1681; Ravetch J. V. et al. 2000, *Science*, 290: 84-89; Ravetch J. V. et al, 2001 *Annu. Rev. Immunol.* 19:275-90; Ravetch J. V. 1994, *Cell*, 78(4): 553-60). The different Fc receptors, the cells that express them, and their isotype specificity is summarized in Table 1 (adapted from *Immunobiology: The Immune System in Health and Disease*, 4$^{th}$ ed. 1999, Elsevier Science Ltd/Garland Publishing, New York).

Fcγ Receptors

Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology between the three family members suggest they arose from a common progenitor perhaps by gene duplication. This invention specifically focuses on FcγRII(CD32).

FcγRII(CD32)

FcγRII proteins are 40 KDa integral membrane glycoproteins which bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRII-A and FcγRII-B create two functionally heterogenous responses to receptor ligation. The fundamental difference is that the A isoform initiates intracellular signaling leading to cell activation such as phagocytosis and respiratory burst, whereas the β isoform initiates inhibitory signals, e.g., inhibiting B-cell activation.

Signaling Through FcγRs

Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs) or immunoreceptor tyrosine based inhibitory motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., PI$_3$K). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When colligated along with an activating FcγR, the ITIM in FcγRIIB becomes phosphorylated and attracts the SH2 domain of the inositol polyphosphate 5'-phosphatase (SHIP), which hydrolyzes phosphoinositol messengers released as a consequence of ITAM-containing FcγR- mediated tyrosine kinase activation, consequently preventing the flux of intracellular Ca$^{++}$. Thus crosslinking of FcγRIIB dampens the activating response to FcγR ligation and inhibits cellular responsiveness. B cell activation, B cell proliferation and antibody secretion is thus aborted.

TABLE 1

Receptors for the Fc Regions of Immunoglobulin Isotypes

| | Receptor | | | | | | |
|---|---|---|---|---|---|---|---|
| | FcγRI (CD64) | FcγRII-A (CD32) | FcγRII-B2 (CD32) | FcγRII-BI (CD32) | FcγRIII (CD16) | FcϵRI | FcαRI (CD89) |
| Binding | IgG1 $10^8$ $M^{-1}$ | IgG1 $2 \times 10^6$ $M^{-1}$ | IgG1 $2 \times 10^6$ $M^{-1}$ | IgG1 $2 \times 10^6$ $M^{-1}$ | IgG1 $5 \times 10^5$ $M^{-1}$ | IgG1 $10^{10}$ $M^{-1}$ | IgG1, IgA2 $10^7$ $M^{-1}$ |
| Cell Type | Macrophages Neutrophils Eosinophils Dendritic cells | Macrophages Neutrophils Eosinophils Dendritic cells Platelets Langerhan cells | Macrophages Neutrophils Eosinophils | B cells Mast cells | NK cells Eosinophil macrophages Neutrophils Mast Cells | Mast cells Eosinophil Basophils | Macrophages Neutropils Eosinophils |
| Effect of Ligation | Uptake Stimulation Activation of respiratory burst Induction of killing | Uptake Granule release | Uptake Inhibition of Stimulation | No uptake Inhibition of Stimulation | Induction of Killing | Secretion of granules | Uptake Induction of killing |

2.2 Diseases of Relevance 2.2.1 Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A cure for cancer has yet to be found. Current treatment options, such as surgery, chemotherapy and radiation treatment, are oftentimes either ineffective or present serious side effects.

Cancer Therapy

Currently, cancer therapy may involve surgery, chemotherapy, hormonal therapy and/or radiation treatment to eradicate neoplastic cells in a patient (See, for example, Stocekdale, 1998, "Principles of Cancer Patient Management", in Scientific American: Medicine, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., Goodman and Gilman's: The Pharmacological Basis of Therapeutics, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response, for example, hybridoma technology has enabled the development of tumor selective monoclonal antibodies (See Green M. C. et al., 2000 *Cancer Treat Rev.,* 26: 269-286; Weiner L M, 1999 *Semin Oncol.* 26(suppl. 14):43-51), and in the past few years, the Food and Drug Administration has approved the first MAbs for cancer therapy: Rituxin (anti-CD20) for non-Hodgkin's Lymphoma and HERCEPTIN® (trastuzumab) [anti-(c-erb-2/HER-2)] for metastatic breast cancer (Suzanne A. Eccles, 2001, *Breast Cancer Res.,* 3: 86-90). However, the potency of antibody effector function, e.g., to mediate antibody dependent cellular cytotoxicity ("ADCC") is an obstacle to such treatment. Methods to improve the efficacy of such immunotherapy are thus needed.

2.2.2 Inflammatory Diseases and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and dis-ability, as well as costing millions of dollars in healthcare expenses and lost wages. (See, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

2.2.3 Allergy

Immune-mediated allergic (hypersensitivity) reactions are classified into four types (I-IV) according to the underlying mechanisms leading to the expression of the allergic symptoms. Type I allergic reactions are characterized by IgE-mediated release of vasoactive substances such as histamine from mast cells and basophils. The release of these substances and the subsequent manifestation of allergic symptoms are initiated by the cross-linking of allergen-bound IgE to its receptor on the surface of mast cells and basophils. In individuals suffering from type I allergic reactions, exposure to an allergen for a second time leads to the production of high levels of IgE antibodies specific for the allergen as a result of the involvement of memory B and T cells in the 3-cell interaction required for IgE production. The high levels of IgE antibodies produced cause an increase in the cross-linking of IgE receptors on mast cells and basophils by allergen-bound IgE, which in turn leads to the activation of these cells and the release of the pharmacological mediators that are responsible for the clinical manifestations of type I allergic diseases.

Two receptors with differing affinities for IgE have been identified and characterized. The high affinity receptor (FcεRI) is expressed on the surface of mast cells and basophils. The low affinity receptor (FcεRII/CD23) is expressed on many cell types including B cells, T cells, macrophages, eosinophils and Langerhan cells. The high affinity IgE receptor consists of three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the FcεRI on mast cells and basophils is of utmost importance in devising strategies for treatment or prevention of IgE-mediated allergies. For example, the elucidation of the IgE receptor-binding site could lead to the identification of peptides or small molecules that block the binding of IgE to receptor-bearing cells in vivo.

Currently, IgE-mediated allergic reactions are treated with drugs such as antihistamines and corticosteroids which attempt to alleviate the symptoms associated with allergic reactions by counteracting the effects of the vasoactive substances released from mast cells and basophils. High doses of antihistamines and corticosteroids have deleterious side effects (e.g., central nervous system disturbance, constipation, etc). Thus, other methods for treating type I allergic reactions are needed.

One approach to the treatment of type I allergic disorders has been the production of monoclonal antibodies which react with soluble (free) IgE in serum, block IgE from binding to its receptor on mast cells and basophils, and do not bind to receptor-bound IgE (i.e., they are non-anaphylactogenic). Two such monoclonal antibodies are in advanced stages of clinical development for treatment of IgE-mediated allergic reactions (see, e.g., Chang, T. W., 2000, Nature Biotechnology 18:157-62).

One of the most promising treatments for IgE-mediated allergic reactions is the active immunization against appropriate non-anaphylactogenic epitopes on endogenous IgE. Stanworth et al. (U.S. Pat. No. 5,601,821) described a strategy involving the use of a peptide derived from the CεH4 domain of the human IgE coupled to a heterologous carrier protein as an allergy vaccine. However, this peptide has been shown not to induce the production of antibodies that react with native soluble IgE. Further, Hellman (U.S. Pat. No. 5,653,980) proposed anti-IgE vaccine compositions based on fusion of full length CεH2-CεH3 domains (approximately 220 amino acid long) to a foreign carrier protein. However, the antibodies induced by the anti-IgE vaccine compositions proposed in Hellman will most likely it result in anaphylaxis since antibodies against some portions of the CsH2 and CsH3 domains of the IgE molecule have been shown to cross-link the IgE receptor on the surface of mast cell and basophils and lead to production of mediators of anaphylaxis (See, e.g., Stadler et al., 1993, Int. Arch. Allergy and Immunology 102:121-126). Therefore, a need remains for treatment of IgE-mediated allergic reactions which do not induce anaphylactic antibodies.

The significant concern over induction of anaphylaxis has resulted in the development of another approach to the treatment of type I allergic disorders consisting of mimotopes that could induce the production of anti-IgE polyclonal antibodies when administered to animals (See, e.g., Rudolf, et al., 1998, Journal of Immunology 160; 3315-3321). Kricek et al. (International Publication No. WO 97/31948) screened phage-displayed peptide libraries with the monoclonal antibody BSWI7 to identify peptide mimotopes that could mimic the conformation of the IgE receptor binding. These mimotopes could presumably be used to induce polyclonal antibodies that react with free native IgE, but not with receptor-bound IgE as well as block IgE from binding to its receptor. Kriek et al. disclosed peptide mimotopes that are not homologous to any part of the IgE molecule and are thus different from peptides disclosed in the present invention.

As evidenced by a survey of the art, there remains a need for enhancing the therapeutic efficacy of current methods of treating or preventing disorders such as cancer, autoimmune disease, inflammatory disorder, or allergy. In particular, there is a need for enhancing the effector function, particularly, the cytotoxic effect of therapeutic antibodies used in treatment of cancer. The current state of the art is also lacking in treating or preventing allergy disorders (e.g., either by antibody therapy or vaccine therapy).

3. SUMMARY OF THE INVENTION

The extracellular domains of FcγRIIA and FcγRIIB are 95% identical and thus they share numerous epitopes. However, FcγRIIA and FcγRIIB exhibit very different activities. The fundamental difference is that the FcγRIIA initiates intracellular signaling leading to cell activation such as phagocytosis and respiratory burst, whereas the FcγRIIB initiates inhibitory signaling. Prior to this invention, to the knowledge of the inventors, antibodies known to distinguish among native human FcγRIIA and native human FcγRIIB have not been identified; in view of their distinctive activities and role in modulating immune responses, such antibodies that recognize native FcγRIIB, and not native FcγRIIA, are needed. The present invention is based, in part, on the discovery of such FcγRIIB-specific antibodies. As used herein, "native FcγRIIB or FcγRIIA" means FcγRIIB or FcγRIIA which is endogenously expressed in a cell and is present on the cell surface of that cell or recombinantly expressed in a mammalian cell and present on the cell surface, but is not FcγRIIB or FcγRIIA expressed in a bacterial cell or denatured, isolated FcγRIIB or FcγRIIA.

The invention relates to an isolated antibody or a fragment thereof that specifically binds FcγRIIB, particularly human FcγRIIB, more particularly native human FcγRIIB, with a greater affinity than said antibody or a fragment thereof binds FcγRIIA, particularly human FcγRIIA, more particularly native human FcγRIIA. Preferably the antibodies of the invention bind the extracellular domain of native human FcγRIIB. In certain embodiments of the invention, the antibody or a fragment thereof binds FcγRIIB with at least 2 times greater affinity than said antibody or a fragment thereof binds FcγRIIA. In other embodiments of the invention, the antibody or a fragment thereof binds FcγRIIB with at least 4 times, at least 6 times, at least 8 times, at least 10 times, at least 100 times, at least 1000 times, at least $10^4$, at least $10^5$, at least $10^6$, at least $10^7$, or at least $10^8$ times greater affinity than said antibody or a fragment thereof binds FcγRIIA In a preferred embodiment, said antibody or a fragment thereof binds FcγRIIB with 100 times, 1000 times, $10^4$ times, $10^5$ times, $10^6$ times, $10^7$ times, or $10^8$ times greater affinity than said antibody or a fragment thereof binds FcγRIIA. Preferably, these binding affinities are determined with the monomeric IgG, and not the aggregated IgG, and binding is via the variable domain (e.g., Fab fragments of the antibodies have binding characteristic similar to the full immunolobulin molecule).

In one embodiment, the FcγRIIB-specific antibody in accordance with the invention is not the monoclonal antibody designated KB61, as disclosed in Pulford et al, 1986 (*Immunology*, 57: 71-76) or the monoclonal antibody designated MAbII8D2 as disclosed in Weinrich et al., 1996, (*Hybridoma*, 15(2):109-6). In a specific embodiment, the FcγRIIB-specific antibody of the invention does not bind to the same epitope and/or does not compete for binding with the monoclonal antibody KB61 or the monoclonal antibody MAbII8D2. Preferably, the FcγRIIB-specific antibody of the invention does not bind the amino acid sequence Ser-Asp-Pro-Asn-Phe-Ser-Ile corresponding to amino acid positions 135-141 of FcγRIIb2 isoform.

The invention relates to an isolated antibody or a fragment thereof that specifically binds FcγRIIB with a greater affinity than said antibody or a fragment thereof binds FcγRIIA, as determined by any standard method known in the art for assessing specificities. The invention relates to an isolated antibody or a fragment thereof that specifically binds FcγRIIB with a greater affinity than said antibody or a fragment thereof binds FcγRIIA, as determined, for example, by western blot, BIAcore or radioimmunoassay. The invention relates to an isolated antibody or a fragment thereof that specifically binds FcγRIIB with a greater affinity than said antibody or a fragment thereof binds FcγRIIA, as determined in an ELISA assay, in the linear range for FcγRIIB binding. In one embodiment of the invention, the invention relates to an isolated antibody, or a fragment thereof that specifically binds FcγRIIB, produced in mammalian system, with a greater affinity than said antibody or a fragment thereof binds FcγRIIA, as determined in an ELISA assay.

In a particular embodiment, the invention relates to an isolated antibody or a fragment thereof that specifically binds FcγRIIB with a greater affinity than said antibody or a fragment thereof binds FcγRIIA, and the constant domain of said antibody further has an enhanced affinity for at least one or more Fc activation receptors. In yet another specific embodiment, said Fc activation receptor is FcγRIII.

In one embodiment of the invention said antibody or a fragment thereof blocks the IgG binding site of FcγRIIB and blocks the binding of aggregated labeled IgGs to FcγRIIB in, for example, a blocking ELISA assay. In one particular embodiment, said antibody or a fragment thereof blocks the binding of aggregated labeled IgGs in an ELISA blocking assay by at least 50%, 60%, 70%, 80%, 90%, 95%, 99%, or 99.9%. In yet another particular embodiment, the antibody or a fragment thereof completely blocks the binding of said aggregated labeled IgG in said ELISA assay.

In another embodiment of the invention, said antibody or a fragment thereof blocks the IgG binding site of FcγRIIB and blocks the binding of aggregated labeled IgG to FcγRIIB, as determined by a double-staining FACS assay.

The invention encompasses the use of antibodies that modulate (i.e., agonize or antagonize) the activity of FcγRIIB. In one embodiment of the invention, the antibodies of the invention agonize at least one activity of FcγRIIB, i.e., elicit signaling. Although not intending to be bound by any mechanism of action, agonistic antibodies of the invention may mimic clustering of FcγRIIB leading to dampening of the activating response to FcγR ligation and inhibition of cellular responsiveness.

In another embodiment of the invention, the antibodies of the invention antagonize at least one activity of FcγRIIB, i.e., block signaling. For example, the antibodies of the invention block the binding of aggregated IgGs to FcγRIIB.

The invention provides antibodies that inhibit FcεRI-induced mast cell activation. The invention further provides anti-FcγRIIB antibodies that inhibit FcγRIIA-mediated macrophage activation in monocytic cells. The invention also provides anti-FcγRIIB antibodies that inhibit B-cell receptor mediated signaling.

In one particular embodiment, the anti-FcγRIIB antibodies block the ligand binding site of FcγRIIB. In a further specific embodiment, the blocking activity can block the negative regulation of immune-complex-triggered activation and consequently enhance the immune response. In a further specific embodiment, the enhanced immune response is an increase in antibody-dependent cellular response. In another specific embodiment, the anti-FcγRIIB antibodies of the invention block crosslinking of FcγRIIB receptors to B cell and/or Fc receptors, leading to B cell, mast cell, dendritic cell, or macrophage activation.

The present invention encompasses the production of novel monoclonal antibodies with specificities for FcγRIIB relative to FcγRIIA. In particular, the invention provides a method for producing FcγRIIB monoclonal antibodies that specifically bind FcγRIIB, particularly human FcγRIIB, with a greater affinity than said monoclonal antibodies bind FcγRIIA, particularly human FcγRIIA, said method comprising: (a) immunizing one or more FcγRIIA transgenic mice with purified FcγRIIB or an immunogenic fragment thereof; (b) producing hybridoma cells lines from spleen cells of said one or more mice; (c) screening said hybridoma cell lines for one or more hybridoma cell lines that produce antibodies that specifically bind FcγRIIB with a greater affinity than the antibodies bind FcγRIIA. The invention encompasses any antibody produced by said method. In one specific embodiment, the invention provides a method for producing FcγRIIB monoclonal antibodies that specifically bind FcγRIIB, particularly human FcγRIIB, with a greater affinity than said monoclonal antibodies bind FcγRIIA, particularly human FcγRIIA, said method comprising: (a) immunizing one or more FcγRIIA transgenic mice with purified FcγRIIB or an immunogenic fragment thereof; (b) booster immunizing said mice for a time sufficient to elicit an immune response; (c) producing hybridoma cells lines from spleen cells of said one or more mice; (d) screening said hybridoma cell lines for one or more hybridoma cell lines that produce antibodies that specifically bind FcγRIIB with a greater affinity than the antibodies bind FcγRIIA. In a preferred embodiment, said mice are booster immunized at least four times over a period of four months. In one embodiment of the invention, said mice are immunized with purified FcγRIIB, which has been mixed with adjuvants known in the art to enhance immune response in said mice. In one particular embodiment of the invention, said immunogenic fragment is the soluble extracellular domain of FcγRIIB. The hybridoma cell lines can be screened using standard techniques known in the art (e.g., ELISA).

In a preferred embodiment, the invention provides a monoclonal antibody produced by clone 2B6 or 3H7, having ATCC accession numbers PTA-4591 and PTA-4592, respectively. In another embodiment, the invention provides an isolated antibody or a fragment thereof that competes for binding with the monoclonal antibody produced by clone 2B6 or 3H7 and binds FcγRIIB, preferably native human FcγRIIB with a greater affinity than said antibody or a fragment thereof binds FcγRIIA, preferably native human FcγRIIA and/or binds to the same epitope of FcγRIIB as the monoclonal antibody produced from clone 2B6 or 3H7 and binds FcγRIIB with a greater affinity than said antibody or a fragment thereof binds FcγRIIA. Furthermore, the invention provides hybridoma cell line 2B6 or 3H7, having ATCC accession numbers PTA-4591 and PTA-4592, respectively.

The methods of the invention also encompass polynucleotides that encode the antibodies of the invention. In one embodiment, the invention provides an isolated nucleic acid sequence encoding a heavy chain or a light chain of an antibody or a fragment thereof that specifically binds FcγRIIB with greater affinity than said antibody or a fragment thereof binds FcγRIIA. The invention also relates to a vector comprising said nucleic acid. The invention further provides a vector comprising a first nucleic acid molecule encoding a heavy chain and a second nucleic acid molecule encoding a light chain, said heavy chain and light chain being of an antibody or a fragment thereof that specifically binds FcγRIIB with greater affinity than said antibody or a fragment thereof binds FcγRIIA. In one specific embodiment, said vector is an expression vector. The invention further provides host cells containing the vectors of or polynucleotides encoding the antibodies of the invention. Preferably, the invention encompasses polynucleotides encoding heavy and light chains of the antibodies produced by the deposited hybridoma clones, having ATCC accession numbers PTA-4591 and PTA-4592, respectively, or portions thereof, e.g., CDRs, variable domains, etc. and humanized versions thereof.

The invention further provides methods for the production of antibodies of the invention or fragments thereof. The antibodies of the invention or fragments thereof can be produced by any method known in the art for the production of antibodies, in particular, by secretion from cultured hybridoma cells, chemical synthesis or by recombinant expression techniques known in the art. In one specific embodiment, the invention relates to a method for recombinantly producing a FcγRIIB-specific antibody, said method comprising:

(i) culturing under conditions suitable for the expression of said antibody in a medium, a host cell containing a first nucleic acid molecule, operably linked to a heterologous promoter and a second nucleic acid operably linked to the same or a different heterologous promoter, said first nucleic acid and second nucleic acid encoding a heavy chain and a light chain, respectively, of an antibody or a fragment thereof that specifically binds FcγRIIB with greater affinity than said antibody or a fragment thereof binds FcγRIIA; and (ii) recovery of said antibody from said medium.

Preferably, the antibodies of the invention are monoclonal antibodies, and more preferably, humanized or human antibodies. In one specific preferred embodiment, the antibodies of the invention bind to the extracellular domain of human FcγRIIB, particularly native human FcγRIIB. In another specific embodiment, the antibodies of the invention specifically or selectively recognize one or more epitopes of FcγRIIB, particularly native human FcγRIIB. Another embodiment of the invention encompasses the use of phage display technology to increase the affinity of the antibodies of the invention for FcγRIIB. Any screening method known in the art can be used to identify mutant antibodies with increased avidity for FcγRIIB (e.g., ELISA). In another specific embodiment, antibodies of the invention are screened using antibody screening assays well known in the art (e.g., BIACORE assays) to identify antibodies with $K_{off}$ rate less than $3 \times 10^{-3}$ s$^{-1}$.

The invention encompasses the use of the antibodies of the invention to detect the presence of FcγRIIB specifically (i.e., FcγRIIB and not FcγRIIA) in a biological sample.

Activating and inhibitory Fc receptors, e.g., FcγRIIA and FcγRIIB, are critical for the balanced function of these receptors and proper cellular immune responses. The invention encompasses the use of the antibodies of the invention for the treatment of any disease related to loss of such balance and regulated control in the Fc receptor signaling pathway. Thus, the FcγRIIB antibodies of the invention have uses in regulating the immune response, e.g., in inhibiting immune response in connection with autoimmune or inflammatory disease, or allergic response. The FcγRIIB antibodies of the invention can also be used to alter certain effector functions to enhance, for example, therapeutic antibody-mediated cytotoxicity.

The antibodies of the invention are useful for prevention or treatment of cancer, for example, in one embodiment, as a single agent therapy. In one embodiment of the invention, the antibodies of the invention are useful for prevention or treatment of B-cell malignancies, particularly non-Hodgkin's lymphoma or chronic lymphocytic leukemia. In a preferred embodiment, the antibodies of the invention are used for the treatment and/or prevention of melanoma. In another embodiment, the antibodies are useful for prevention or treatment of cancer, particularly in potentiating the cytotoxic activity of cancer antigen-specific therapeutic antibodies with cytotoxic activity to enhance tumor cell killing and/or enhancing antibody dependent cytotoxic cellular ("ADCC") activity, complement dependent cytotoxic ("CDC") activity, or phagocytosis of the therapeutic antibodies. The invention provides a method of treating cancer in a patient having a cancer characterized by a cancer antigen, said method comprising administering to said patient a therapeutically effective amount of a first antibody or a fragment thereof that specifically binds FcγRIIB with greater affinity than said antibody or a fragment thereof binds FcγRIIA, and a second antibody that specifically binds said cancer antigen and is cytotoxic. The invention also provides a method of treating cancer in a patient having a cancer characterized by a cancer antigen, said method comprising administering to said patient a therapeutically effective amount of an antibody or a fragment thereof that specifically binds FcγRIIB, particularly native human FcγRIIB with greater affinity than said antibody or a fragment thereof binds FcγRIIA, preferably native human FcγRIIA, and the constant domain of which further has an increased affinity for one or more Fc activation receptors, when the antibody is monomeric, such as FcγRIIIA, and an antibody that specifically binds said cancer antigen and is cytotoxic. In one particular embodiment, said Fc activation receptor is FcγRIIIA.

In another embodiment, the invention provides a method of enhancing an antibody mediated cytotoxic effect in a subject being treated with a cytotoxic antibody, said method comprising administering to said patient an antibody of the invention or a fragment thereof, in an amount sufficient to enhance the cytotoxic effect of said cytotoxic antibody. In yet another embodiment, the invention provides a method of enhancing an antibody-mediated cytotoxic effect in a subject being treated with a cytotoxic antibody, said method comprising administering to said patient an antibody of the invention or a fragment thereof, further having an enhanced affinity for an Fc activation receptor, when monomeric, in an amount sufficient to enhance the cytotoxic effect of said cytotoxic antibody. In yet another embodiment, the invention provides a method further comprising the administration of one or more additional cancer therapies.

The invention further provides a pharmaceutical composition comprising (i) a therapeutically effective amount of the antibody or a fragment thereof that specifically binds FcγRIIB with greater affinity than said antibody or a fragment thereof binds FcγRIIA; and (ii) a pharmaceutically acceptable carrier. The invention additionally provides a pharmaceutical composition comprising (i) a therapeutically effective amount of the antibody or a fragment thereof that specifically binds FcγRIIB with greater affinity than said antibody or a fragment thereof binds FcγRIIA; (ii) a cytotoxic antibody that specifically binds a cancer antigen; and (iii) a pharmaceutically acceptable carrier.

The invention encompasses the use of the antibodies of the invention in combination with any therapeutic antibody that mediates its therapeutic effect through cell killing to potentiate the antibody's therapeutic activity. In one particular embodiment, the antibodies of the invention potentiate the antibody's therapeutic activity by enhancing antibody-mediated effector function. In another embodiment of the invention, the antibodies of the invention potentiate the cytotoxic antibody's therapeutic activity by enhancing phagocytosis and opsonization of the targeted tumor cells. In yet another embodiment of the invention, the antibodies of the invention potentiate the antibody's therapeutic activity by enhancing antibody-dependent cell-mediated cytotoxicity ("ADCC") in destruction of the targeted tumor cells.

In some embodiments, the invention encompasses use of the antibodies of the invention in combination with a therapeutic antibody that does not mediate its therapeutic effect through cell killing to potentiate the antibody's therapeutic activity. In a specific embodiment, the invention encompasses use of the antibodies of the invention in combination with a therapeutic apoptosis inducing antibody with agonistic activity, e.g., anti-Fas antibody. Therapeutic apoptosis inducing antibodies may be specific for any death receptor known in the art for the modulation of apoptotic pathway, e.g., TNFR receptor family member.

The invention encompasses using the antibodies of the invention to block macrophage mediated tumor cell progression and metastasis. The antibodies of the invention are particularly useful in the treatment of solid tumors, where macrophage infiltration occurs. The antagonistic antibodies of the invention are particularly useful for controlling, e.g., reducing or eliminating, tumor cell metastasis, by reducing or eliminating the population of macrophages that are localized at the tumor site. The invention further encompasses antibodies that effectively deplete or eliminate immune effector cells other than macrophages that express FcγRIIB, e.g., dendritic cells. Effective depletion or elimination of immune effector cells using the antibodies of the invention may range from a reduction in population of the effector cells by 50%, 60%, 70%, 80%, preferably 90%, and most preferably 99%.

In some embodiments, the agonistic antibodies of the invention are particularly useful for the treatment of tumors of non-hematopoietic origin, including tumors of melanoma cells.

In some embodiments, the invention encompasses use of the antibodies of the invention in combination with therapeutic antibodies that immunospecifically bind to tumor antigens that are not expressed on the tumor cells themselves, but rather on the surrounding reactive and tumor supporting, non-malignant cells comprising the tumor stroma. In a preferred embodiment, an antibody of the invention is used in combination with an antibody that immunospecifically binds a tumor antigen on a fibroblast cell, e.g., fibroblast activation protein (FAP).

The invention provides a method of treating an autoimmune disorder in a patient in need thereof, said method comprising administering to said patient a therapeutically effective amount of one or more antibodies of the invention. The invention also provides a method of treating an autoimmune disorder in a patient in need thereof, said method further comprising administering to said patient a therapeutically effective amount of one or more anti-inflammatory agents, and/or one or more immunomodulatory agents.

The invention also provides a method of treating an inflammatory disorder in a patient in need thereof, said method comprising administering to said patient a therapeutically effective amount of one or more antibodies of the invention. The invention also provides a method of treating an inflammatory disorder in a patient in need thereof, said method further comprising administering to said patient a therapeutically effective amount of one or more anti-inflammatory agents, and/or one or more immunomodulatory agents.

The invention provides a method of enhancing an immune response to a vaccine composition in a subject, said method comprising administering to said subject an antibody or a fragment thereof that specifically binds FcγRIIB with greater affinity than said antibody or a fragment thereof binds FcγRIIA, and a vaccine composition, such that said antibody or a fragment thereof is administered in an amount effective to enhance the immune response to said vaccine composition in said subject. The antibodies of the invention may be used to enhance a humoral and/or cell mediated response against the antigen(s) of the vaccine composition. The antibodies of the invention may be used in combination with any vaccines known in the art. The invention encompasses the use of the antibodies of the invention to either prevent or treat a particular disorder, where an enhanced immune response against a particular antigen or antigens is effective to treat or prevent the disease or disorder.

The invention also provides a method for enhancing immune therapy for an infectious agent wherein the antibodies of the invention are administered to a patient that is already infected by a pathogen, such as HIV or HSV, to enhance opsonization and phagocytosis of infected cells.

The invention provides a method of treating diseases with impaired apoptotic mediated signaling, e.g., cancer, autoimmune disease. In a specific embodiment, the invention encompasses a method of treating a disease with deficient Fas-mediated apoptosis, said method comprising administering an antibody of the invention in combination with an anti-Fas antibody.

In another embodiment, the invention provides a method of diagnosis of an autoimmune disease in a subject comprising: (i) contacting a biological sample from said subject with an effective amount of an antibody of the invention; and (ii) detecting binding of said antibody or a fragment thereof, wherein detection of said detectable marker above a background or standard level indicates that said subject has an autoimmune disease.

The invention further provides a method for treating or preventing an IgE-mediated allergic disorder in a patient in need thereof, comprising administering to said patient a therapeutically effective amount of the agonistic antibodies of the invention. The invention also provides a method for treating or preventing an IgE-mediated allergic disorder in a patient in need thereof, comprising administering to said patient the antibodies of the invention in combination with other therapeutic antibodies or vaccine compositions used for the treatment or prevention of IgE-mediated allergic disorders.

3.1 Definitions

As used herein, the term "specifically binds to FcγRIIB" and analogous terms refer to antibodies or fragments thereof that specifically bind to FcγRIIB or a fragment thereof and do not specifically bind to other Fc receptors, in particular to FcγRIIA. Further it is understood to one skilled in the art, that an antibody that specifically binds to FcγRIIB, may bind through the variable domain or the constant domain of the antibody. If the antibody that specifically binds to FcγRIIB binds through its variable domain, it is understood to one skilled in the art that it is not aggregated, i.e., is monomeric. An antibody that specifically binds to FcγRIIB may bind to other peptides or polypeptides with lower affinity as determined by, e.g., immunoassays, BIAcore, or other assays known in the art. Preferably, antibodies or fragments that specifically bind to FcγRIIB or a fragment thereof do not cross-react with other antigens. Antibodies or fragments that specifically bind to FcγRIIB can be identified, for example, by immunoassays, BIAcore, or other techniques known to those of skill in the art. An antibody or a fragment thereof binds specifically to a FcγRIIB when it binds to FcγRIIB with higher affinity than to any cross-reactive antigen as determined using experimental techniques, such as western blots, radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

As used herein, the term "native FcγRIIB" refers to FcγRIIB which is endogenously expressed and present on the surface of a cell. In some embodiments, "native FcγRIIB" encompasses a protein that is recombinantly expressed in a mammalian cell. Preferably, the native FcγRIIB is not expressed in a bacterial cell, i.e., *E. coli*. Most preferably the native FcγRIIB is not denatured, i.e., it is in its biologically active conformation.

As used herein, the term "native FcγRIIA" refers to FcγRIIA which is endogenously expressed and present on the surface of a cell. In some embodiments, "native FcγRIIA" encompasses a protein that is recombinantly expressed in a mammalian cell. Preferably, the native FcγRIIA is not expressed in a bacterial cell, i.e., *E. coli*. Most preferably the native FcγRIIA is not denatured, i.e., it is in its biologically active conformation.

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

The term "derivative" as used herein refers to a polypeptide that comprises an amino acid sequence of a FcγRIIB polypeptide, a fragment of a FcγRIIB polypeptide, an antibody that immunospecifically binds to a FcγRIIB polypeptide, or an antibody fragment that immunospecifically binds to a FcγRIIB polypeptide, that has been altered by the introduction of amino acid residue substitutions, deletions or additions (i.e., mutations). In some embodiments, an antibody derivative or fragment thereof comprises amino acid residue substitutions, deletions or additions in one or more CDRs. The antibody derivative may have substantially the same binding, better binding, or worse binding when compared to a non-derivative antibody. In specific embodiments, one, two, three, four, or five amino acid residues of the CDR have been substituted, deleted or added (i.e., mutated). The term "derivative" as used herein also refers to a FcγRIIB polypeptide, a fragment of a FcγRIIB polypeptide, an antibody that immunospecifically binds to a FcγRIIB polypeptide, or an antibody fragment that immunospecifically binds to a FcγRIIB polypeptide which has been modified, i.e., by the covalent attachment of any type of molecule to the polypeptide. For example, but not by way of limitation, a FcγRIIB polypeptide, a fragment of a FcγRIIB polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of a FcγRIIB polypeptide, a fragment of a FcγRIIB polypeptide, an antibody, or antibody fragment may be modified by chemical modifications using techniques known to those of skill in the art, including, but not limited to, specific chemical cleavage, acetylation, formulation, metabolic synthesis of tunicamycin, etc. Further, a derivative of a FcγRIIB polypeptide, a fragment of a FcγRIIB polypeptide, an antibody, or antibody fragment may contain one or more non-classical amino acids. In one embodiment, a polypeptide derivative possesses a similar or identical function as a FcγRIIB polypeptide, a fragment of a FcγRIIB polypeptide, an antibody, or antibody fragment described herein. In another embodiment, a derivative of a FcγRIIB polypeptide, a fragment of a FcγRIIB polypeptide, an antibody, or antibody fragment has an altered activity when compared to an unaltered polypeptide. For example, a derivative antibody or fragment thereof can bind to its epitope more tightly or be more resistant to proteolysis.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen.

As used herein, the term "immunomodulatory agent" and variations thereof including, but not limited to, immunomodulatory agents, refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide. Preferably, antibody fragments are epitope binding fragments.

As used herein, the term "humanized antibody" refers to forms of non-human (e.g., murine) antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to a FcγRIIB polypeptide, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519, 596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169: 1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp): 5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596.

As used herein, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain Chothia and Lesk, 1987, *J. Mol. Biol.* 196:901-917). CDR residues for Eph099B-208.261 and Eph099B-233.152 are listed in Table 1. "Framework Region" or "FR" residues are those variable domain residues other than the hypervariable region residues as herein defined.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994). In specific embodiments, scFvs include bi-specific scFvs and humanized scFvs.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, the terms "treat," "treating" and "treatment" refer to the eradication, reduction or amelioration of symptoms of a disease or disorder related to the loss of regulation in the Fc receptor signaling pathway or to enhance the therapeutic efficacy of another therapy, e.g., a therapeutic antibody, vaccine therapy. In some embodiments, treatment refers to the eradication, removal, modification, or control of primary, regional, or metastatic cancer tissue that results from the administration of one or more therapeutic agents. In certain embodiments, such terms refer to the minimizing or delaying the spread of cancer resulting from the administration of one or more therapeutic agents to a subject with such a disease.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art, see, e.g., the *Physicians' Desk Reference* (56$^{th}$ ed., 2002), which is incorporated herein by reference in its entirety.

As used herein, a "therapeutically effective amount" refers to that amount of the therapeutic agent sufficient to treat or manage a disease or disorder associated with FcγRIIB and any disease related to the loss of regulation in the Fc receptor signaling pathway or to enhance the therapeutic efficacy of another therapy, e.g., therapeutic antibody, vaccine therapy, etc. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of FcγRIIB antibody of the invention, the term can encompass an amount that improves overall therapy, reduces or avoids unwanted effects, or enhances the therapeutic efficacy of or synergies with another therapeutic agent.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of an FcγRIIB antibody of the invention, the term can encompass an amount that improves overall prophylaxis or enhances the prophylactic efficacy of or synergies with another prophylactic agent, such as but not limited to a therapeutic antibody. In certain embodiments, the term "prophylactic agent" refers to an agonistic FcγRIIB-specific antibody. In other embodiments, the term "prophylactic agent" refers to an antagonistic FcγRIIB-specific antibody. In certain other embodiments, the term "prophylactic agent" refers to cancer chemotherapeutics, radiation therapy, hormonal therapy, biological therapy (e.g., immunotherapy), and/or FcγRIIB antibodies of the invention. In other embodiments, more than one prophylactic agent may be administered in combination.

As used herein, the terms "manage," "managing" and "management" refer to the beneficial effects that a subject derives from administration of a prophylactic or therapeutic agent, which does not result in a cure of the disease. In certain embodiments, a subject is administered one or more prophylactic or therapeutic agents to "manage" a disease so as to prevent the progression or worsening of the disease.

As used herein, the terms "prevent", "preventing" and "prevention" refer to the prevention of the recurrence or onset of one or more symptoms of a disorder in a subject resulting from the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

4. BRIEF DESCRIPTION OF THE DRAWINGS

FIGS. 1A-1D: Direct binding of the antibody produced from the 3H7 clone to FcγRIIB and FcγRIIA.

A (FIGS. 1A-1B) The direct binding of antibodies from some of the hybridoma cultures to the FcγRIIs were compared to a commercially available anti-FcγRII antibody in an ELISA assay where the plate was coated with the receptors. Different dilutions (1:10) of the supernatants were incubated on the plate. The bound antibodies were detected with a goat anti-mouse HRP conjugated antibody and the absorbance was monitored at 650 nm.

B. (FIGS. 1C-1D) The direct binding of the antibody from the 3H7 hybridoma culture (supernatant n. 7 from the FIGS. 1A-B), in crude (FIG. 1C) and purified from (FIG. 1D), to FcγRIIA and FcγRIIB, were compared using the same ELISA assay as in 1A.

Figure 2:
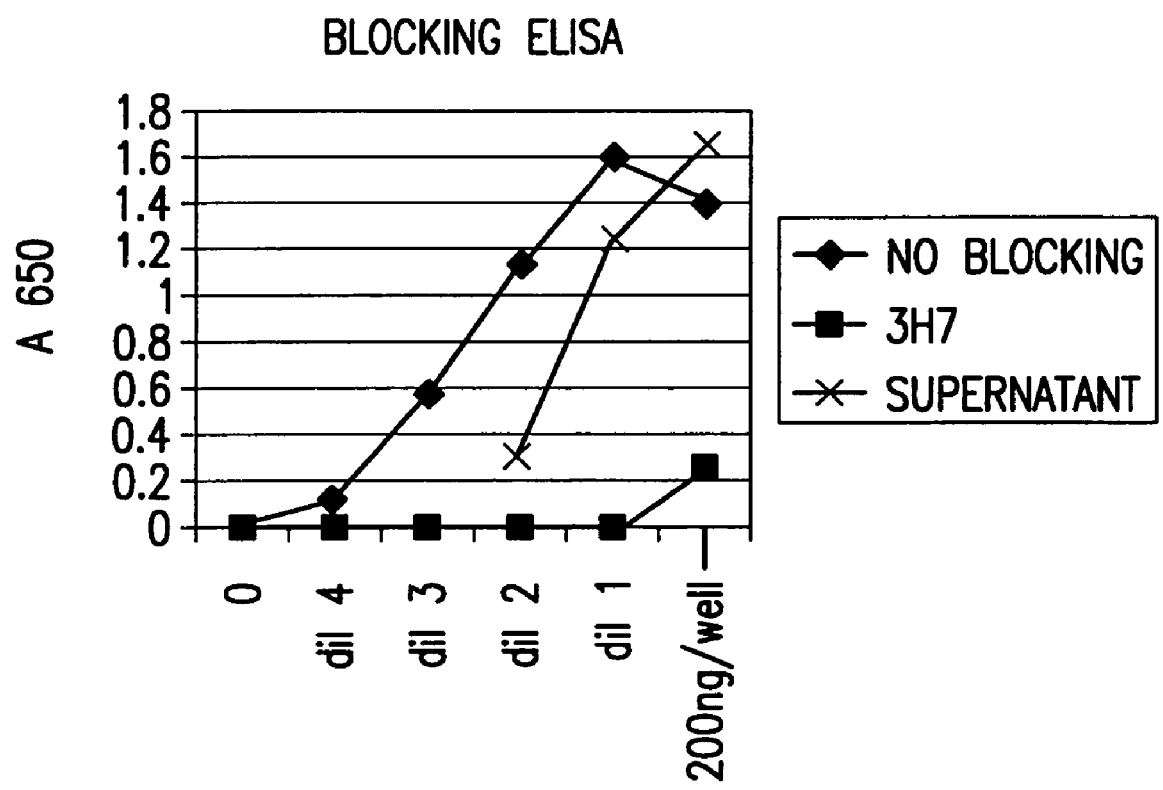

FIG. 2: Competition in binding to FcγRIIB of the antibody produced from the 3H7 hybridoma and aggregated biotinylated human IgG.

The ability of the 3H7 antibody to compete with aggregated biotinylated human IgG for binding to FcγRIIB was measured using a blocking ELISA experiment.

The ELISA plate coated with FcγRIIB was incubated with the supernatant containing the 3H7 antibody and with a supernatant from the same hybridoma cells but not containing antibody (negative control).

Different dilutions (1:3) starting from 200 ng/well, of aggregated biotinylated human IgG were then added to the plate and the bound aggregates were detected with Streptavidin-Horse-Radish Peroxidase conjugated, the reaction was developed with TMB and the absorbance was monitored at 650 nm.

Figure 3:
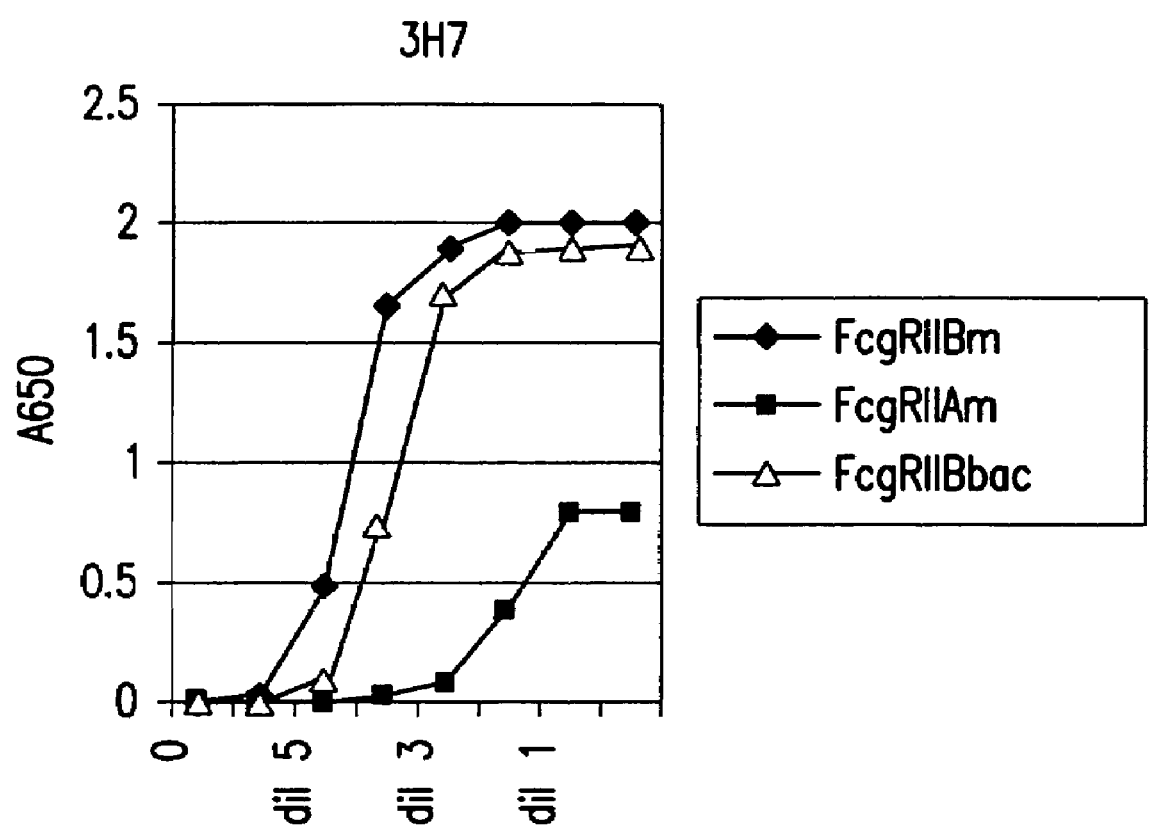

FIG. 3: Comparison of the direct binding of the 3H7 antibody to FcγRIIB produced in a bacterial or in a mammalian system.

Direct binding of the 3H7 antibody to FcγRIIB was measured using an ELISA assay. Binding to the bacterial or mammalian produced FcγRIIB was compared. The antibody titration started from the straight supernatant followed by 1:10 dilutions. The bound antibody was detected with a goat anti-mouse HRP conjugated antibody, the reaction was developed with TMB and the absorbance was monitored at 650 nm.

Figure 4:
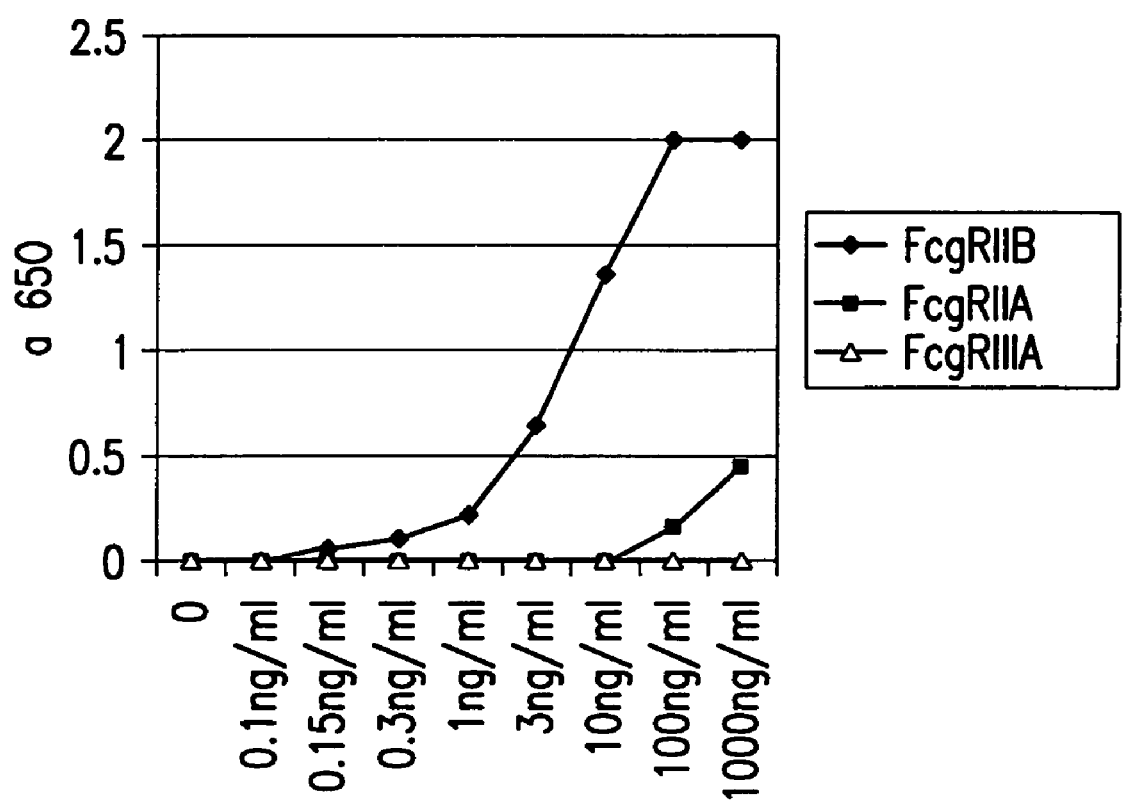

FIG. 4: Direct binding of the 3H7 antibody to FcγRIIA, FcγRIIB and FcγRIIIA.

The direct binding of the purified 3H7 antibody to FcγRIIA, FcγRIIB and FcγRIIIA expressed in a mammalian system were compared using the ELISA assay. ELISA plate was coated with the three receptors (100 ng/well). Different dilutions of the purified 3H7 antibody were incubated on the coated plate. A goat anti-mouse-HRP conjugated antibody was used for detection of the bound specific antibody, the reaction was developed with TMB and the absorbance was monitored at 650 nm.

Figure 5A:
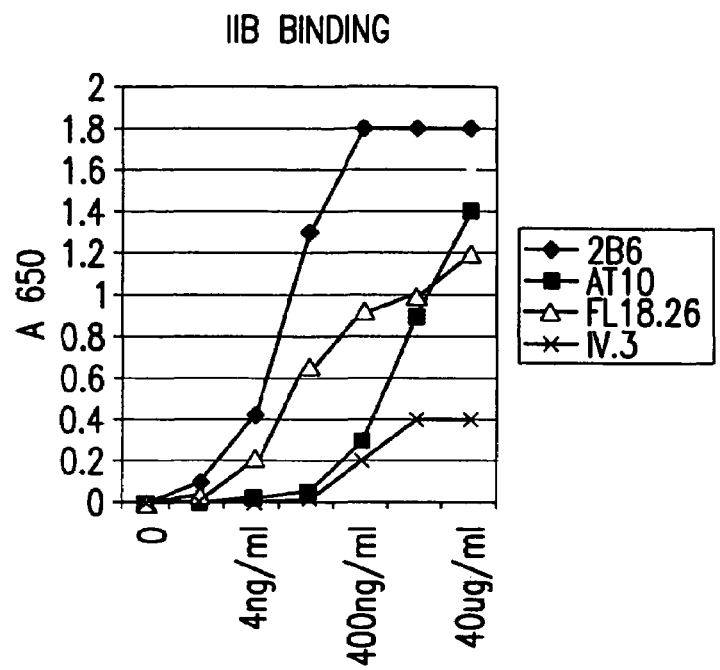
Figure 5B:
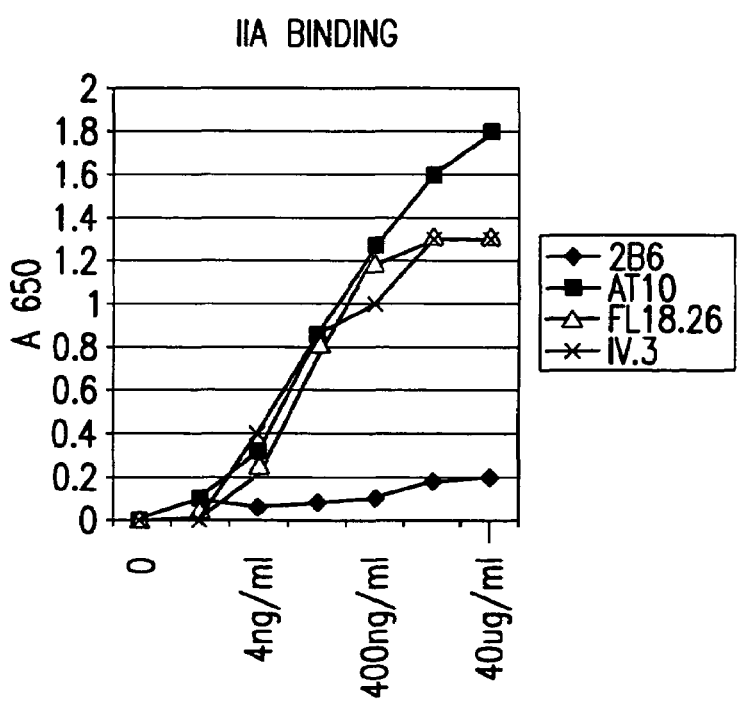
Figure 5C:
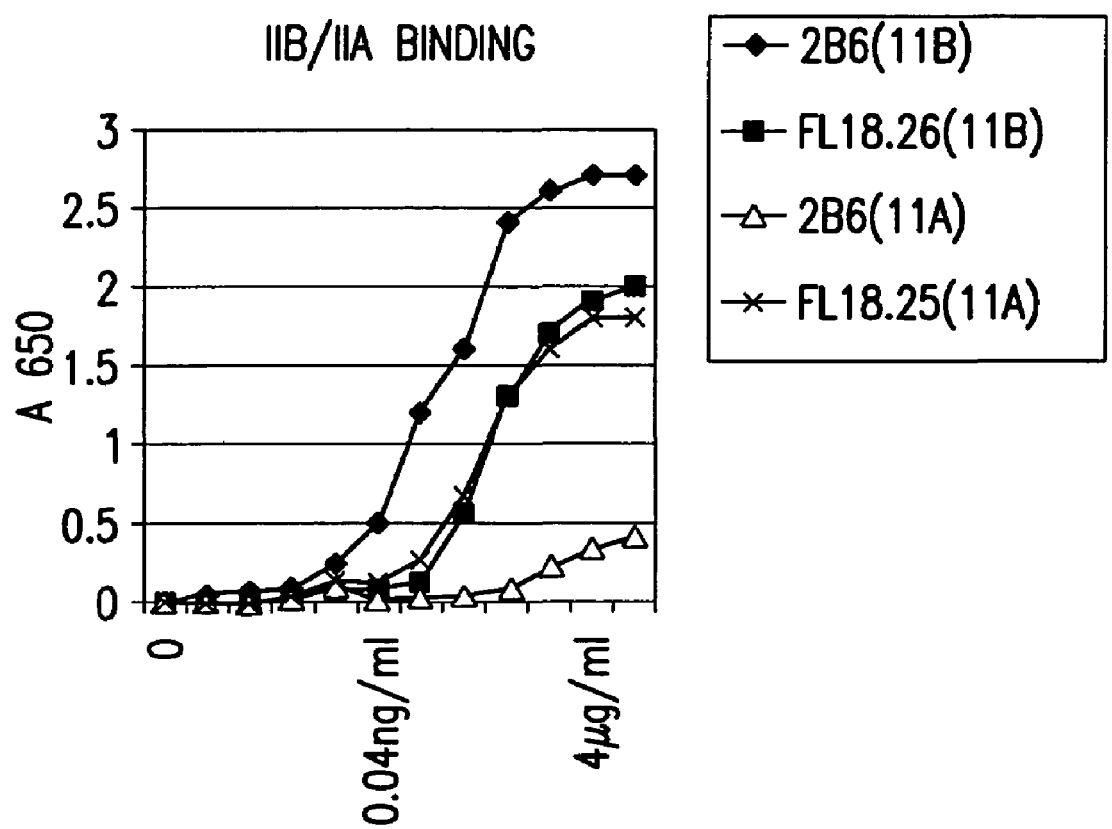

FIGS. 5A-5C: Comparison of the direct binding ability to FcγRIIA and FcγRIIB of the antibody purified from clone 2B6 compared to other three commercially available monoclonal antibodies against FcγRII.

The binding of 2B6 antibody to FcγRIIA (FIG. 5B) and FcγRIIB (FIG. 5A) is compared to that of three other commercially available raised against FcγRII. The ELISA format used is the same described in FIG. 4. FIG. 5C shows IIB/IIA binding of 2B6 and FL18.26.

Figure 6A:
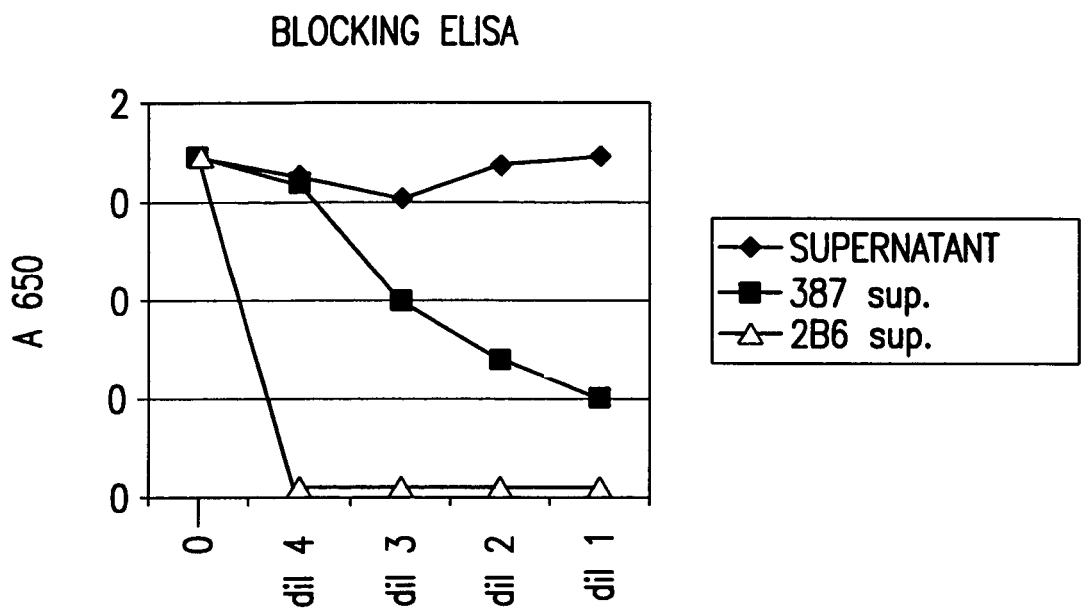
Figure 6B:
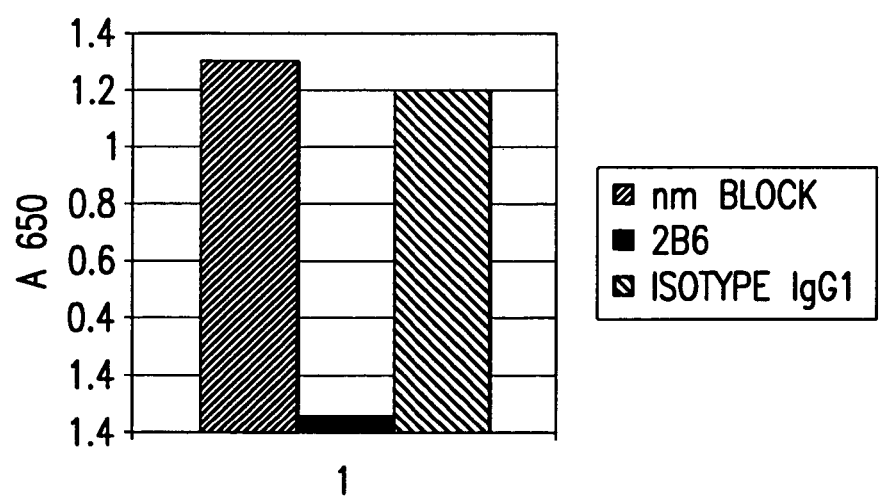

FIGS. 6A and 6B: Competition in binding of the antibody produced from clone 2B6 and aggregated biotinylated human IgG to FcγRIIB.

FIG. 6A: The ability of the antibody present in the supernatant from the clone 2B6 to compete for binding to FcγRIIB with aggregated biotinylated human IgG was measured using a blocking ELISA experiment.

The 2B6 antibody competition ability was compared to that of a negative supernatant from hybridoma and to that of 3H7 antibody.

An ELISA plate coated with FcγRIIB was incubated with different dilutions (1:10) of the supernatants. After washes the plate was incubated with a fixed amount of aggregated biotinylated human IgG (1 mg/well) and the bound aggregates were detected with Stretavidin-HRP conjugated. The reaction was developed with TMB and the absorbance was monitored at 650 nm. FIG. 6B: The same blocking ELISA described in panel A was performed with purified 2B6 antibody and the data from one concentration of blocking antibody used (4 mg/well) were represented in a bar diagram. The 2B6 ability to block aggregated human IgG binding to FcγRIIB was compared to that of a mouse IgG1 isotype control.

Figure 7A:
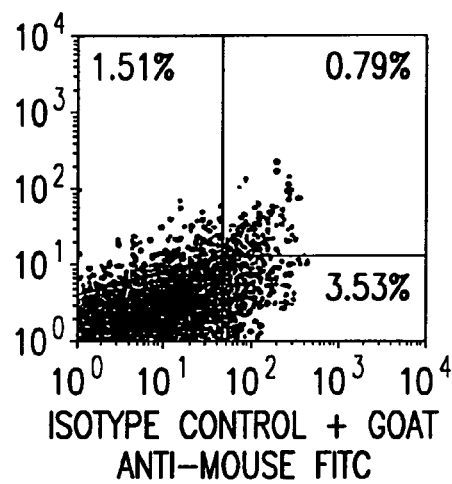
Figure 7B:
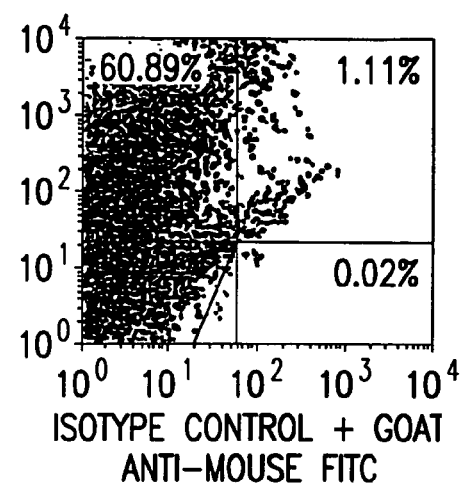
Figure 7C:
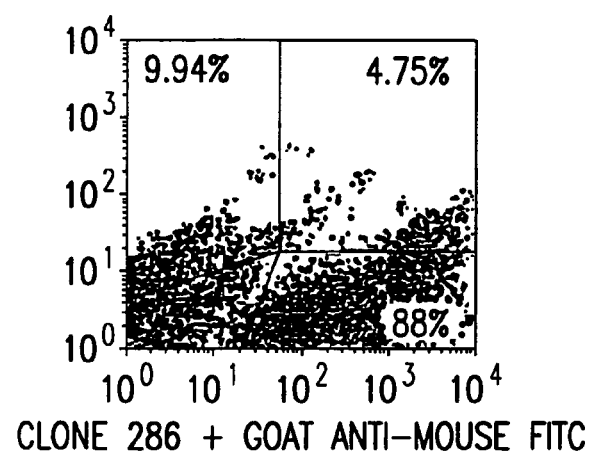

FIGS. 7A-7C: Competition of 2B6 antibody and aggregated biotinylated human IgG in binding to FcγRIIB using a double-staining FACS assay.

A double staining FACS assay was performed to characterize the 2B6 antibody using CHO-K1 cells that had been stably transfected with full-length mammalian FcγRIIB. FIG. 7A: The transfectant cells were stained with mouse IgG1 isotype control followed by a goat anti-mouse-FITC conjugated antibody and Streptavidin-PE. FIG. 7B: The transfectant cells were stained with aggregated biotinylated human IgG after being stained with mouse IgG1 isotype control and labeled with a goat anti-mouse-FITC conjugated antibody to detect the bound monoclonal antibody and with Streptavidin-PE conjugated to detect the bound aggregates. FIG. 7C: The cells were stained with 2B6 antibody, the antibody was removed by washes and the cells were incubated with aggregated biotinylated human IgG. Cells were washed and labeled with goat anti-mouse-FITC conjugated antibody to detect the bound monoclonal antibody and with Steptavidin-PE conjugated to detect the bound aggregates.

Figure 8A:
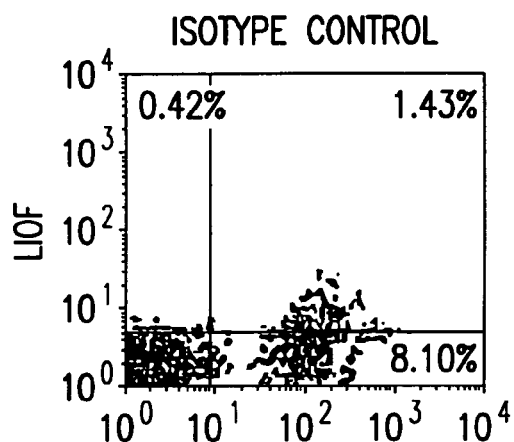
Figure 8B:
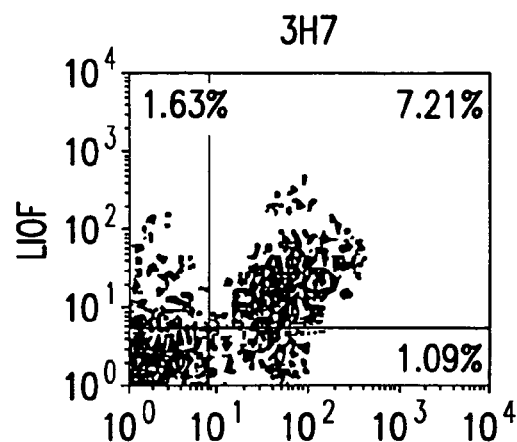
Figure 8C:
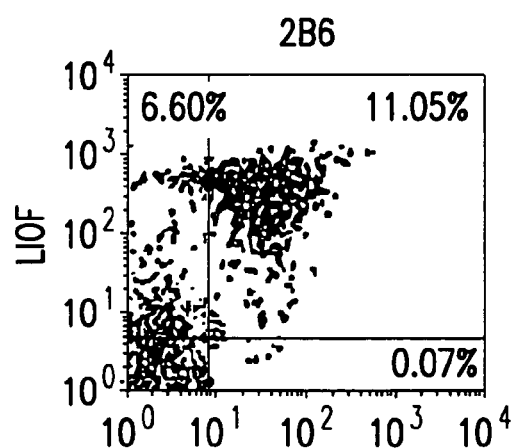

FIGS. 8A-8C: Monoclonal anti FcγRIIB antibodies and CD20 co-stain of human B lymphocytes.

Cells from human blood ("buffy coat") were stained with anti-CD20-FITC conjugated antibody, to select the B lymphocytes population, as well as 3H7 and 2B6. The bound anti-FcγRIIB antibodies were detected with a goat anti-mouse-PE conjugated antibody.

FIG. 8A. Cells were co-stained with anti-CD20-FITC antibody and mouse IgG1 isotype control.

FIG. 8B. Cells were co-stained with anti-CD20-FITC antibody and 3H7 antibody.

FIG. 8C. Cells were co-stained with anti-CD20-FITC antibody and 2B6 antibody.

Figure 9A:
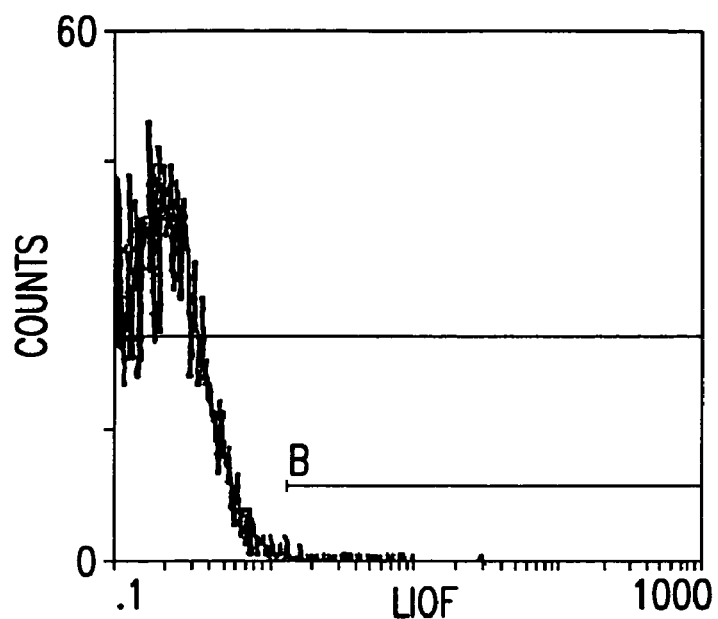
Figure 9B:
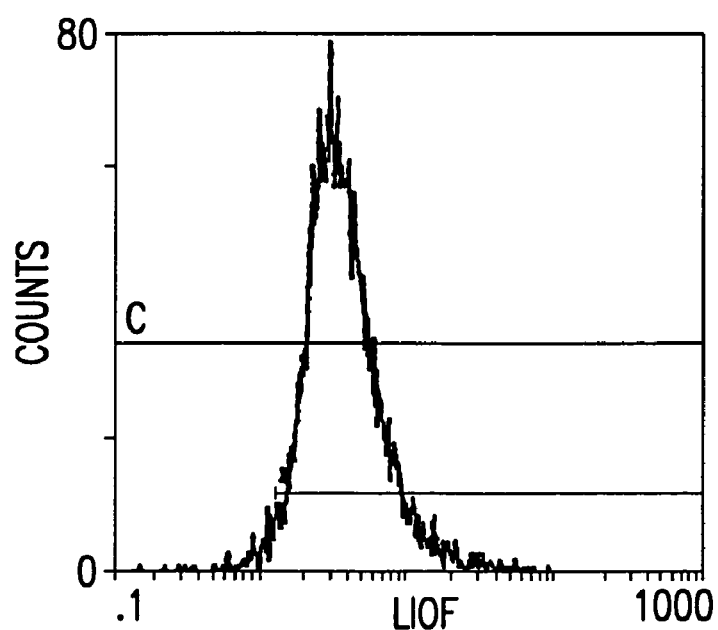
Figure 9C:
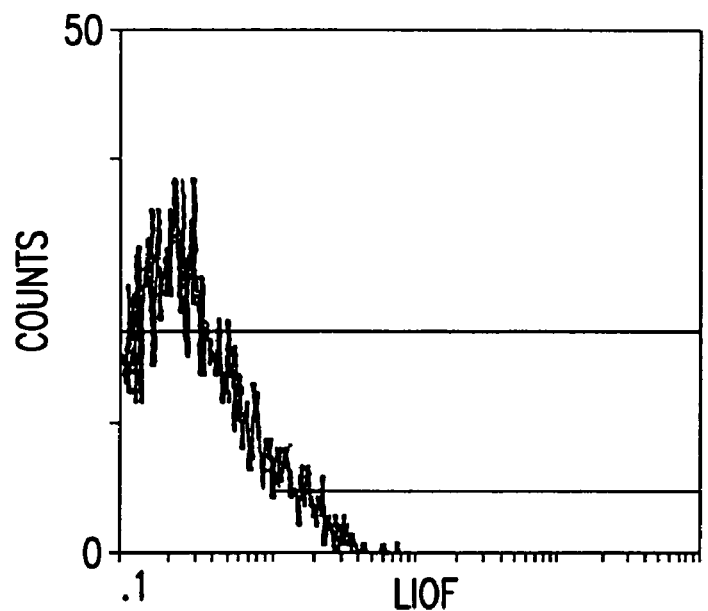

FIGS. 9A-9C: Staining of CHO cells expressing FcγRIIB.

A. (FIGS. 9A-9B) CHO/IIB cells were stained with mouse IgG1 isotype control (FIG. 9A) and 3H7 antibody (FIG. 9B).

Figure 9D:
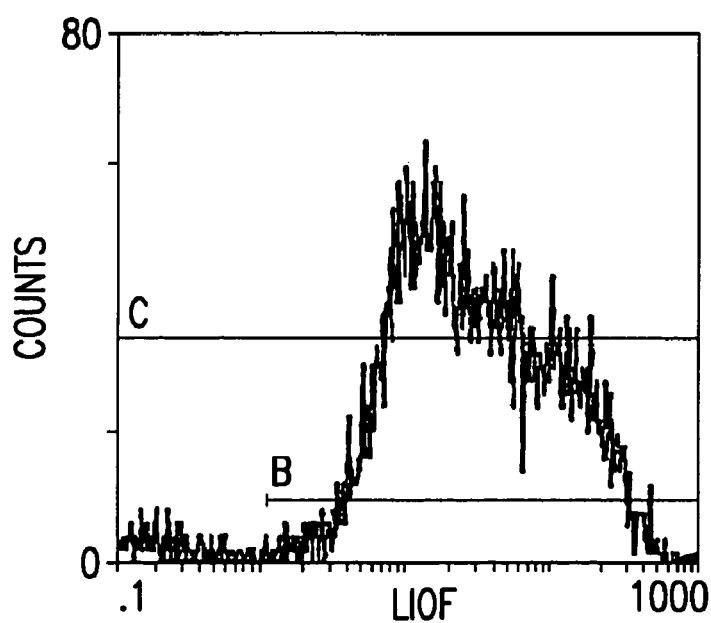

B. (FIG. 9C-9D) CHO/IIB cells were stained with mouse IgG1 isotype control (FIG. 9C) and 2B6 antibody (FIG. 9D).

The cell-bound antibodies were labeled with a goat anti-mouse-PE conjugated antibody.

FIGS. 10A-10G: Binding of humanized antibodies to FcγRIIB-expressing CHO cells.

Figure 10G:
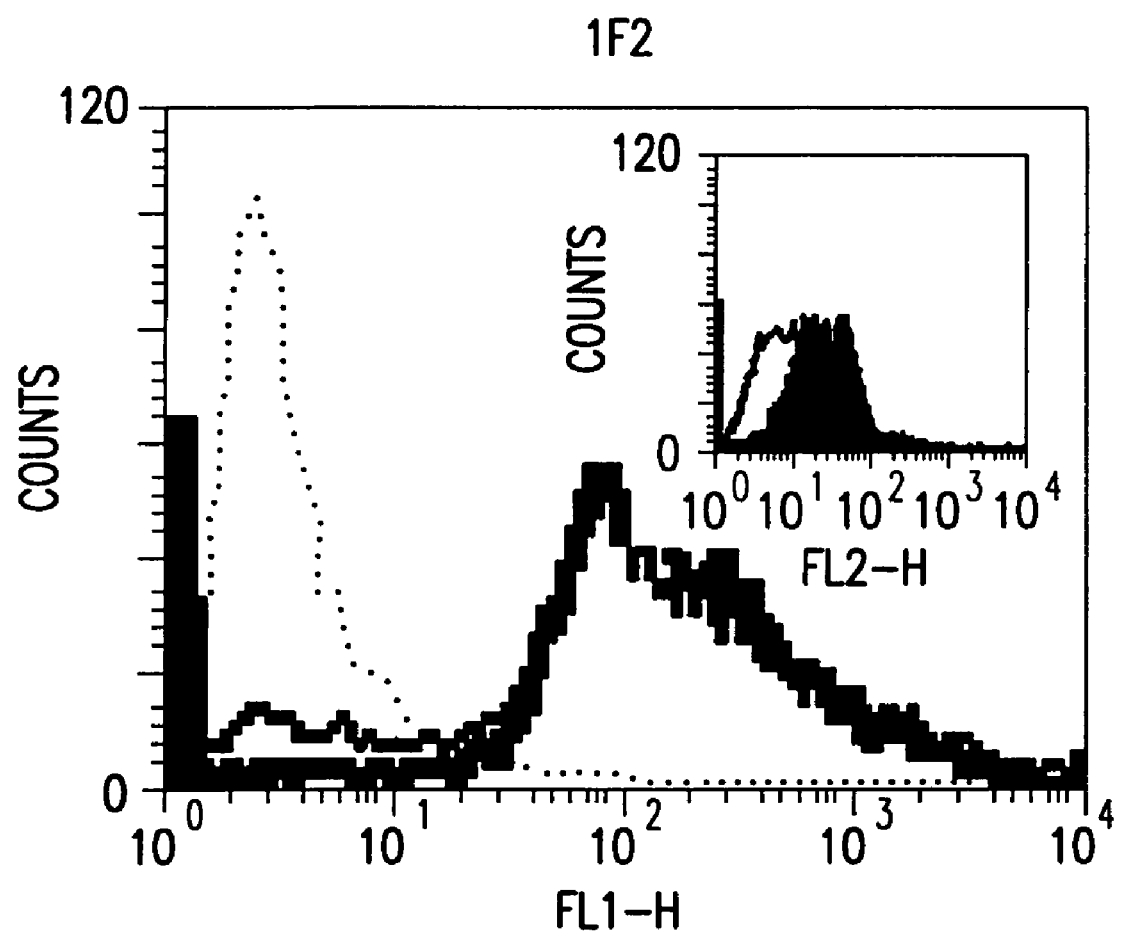

CHO cells expressing huFcγRIIB were incubated with 3H7 antibody (FIG. 10A), 2B6 antibody (FIG. 10B), 2E1 antibody (FIG. 10C), 2H9 antibody (FIG. 10D), 1D5 antibody (FIG. 10E), 2D11 antibody (FIG. 10F) and 1F2 antibody (FIG. 10G). Cells were washed and 9 µg/ml of aggregated human IgG were added to the cells on ice. The human aggregated IgG were detected with goat anti-human-IgG-FITC. Samples were analyzed by FACS. . . . isotype control+goat anti-huIgG-FITC, isotype control+aggregated huIgG+goat anti-huIgG-FITC, anti-FcγRIIB antibody (2B, 3H7, 2H9, 1D5, 2D11 and 1F2)+aggregated huIgG+goat anti-human-IgG-FITC. The amount of each antibody bound to the receptor on the cells was also detected (insert) on a separate set of samples using a goat anti-mouse PE-conjugated antibody.

FIG. 11: Staining of Human PBMCs with 2B6, 3H7 and IV.3 Antibodies.

Figure 11A:
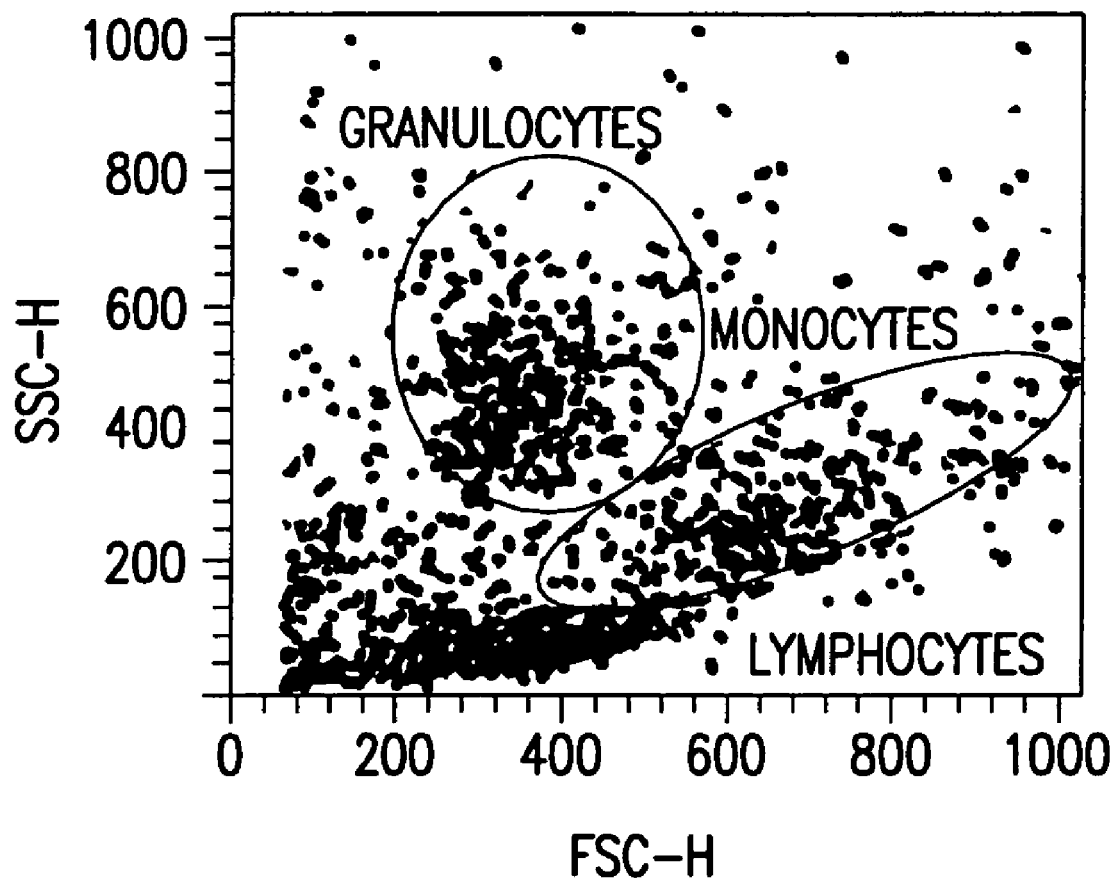

Human PBMCs were stained with 2B6 (FIGS. 11B, 11C, 11H, 11K and 11L), 3H7 (FIGS. 11D, 11E, 11I, 11M and 11N), and 1V.3 (FIGS. 11F, 11G, 11J, 11O and 11P) antibodies, as indicated on the right side of the panel, followed by a goat anti-mouse-Cyanine(Cy5) conjugated antibody (two color staining using anti-CD20-FITC conjugated antibody for B lymphocytes (FIGS. 11B, 11D and 11F), anti-CD14-PE conjugated antibody for monocytes (FIGS. 11K, 11M and 11O), anti-CD56-PE conjugated antibody for NK cells (FIGS. (FIGS. 11C, 11E, 11G, 11L, 11N and 11P). FIG. 11A demonstrates staining results for monocytes, B lymphocytes and granulocytes.

Figure 12A:
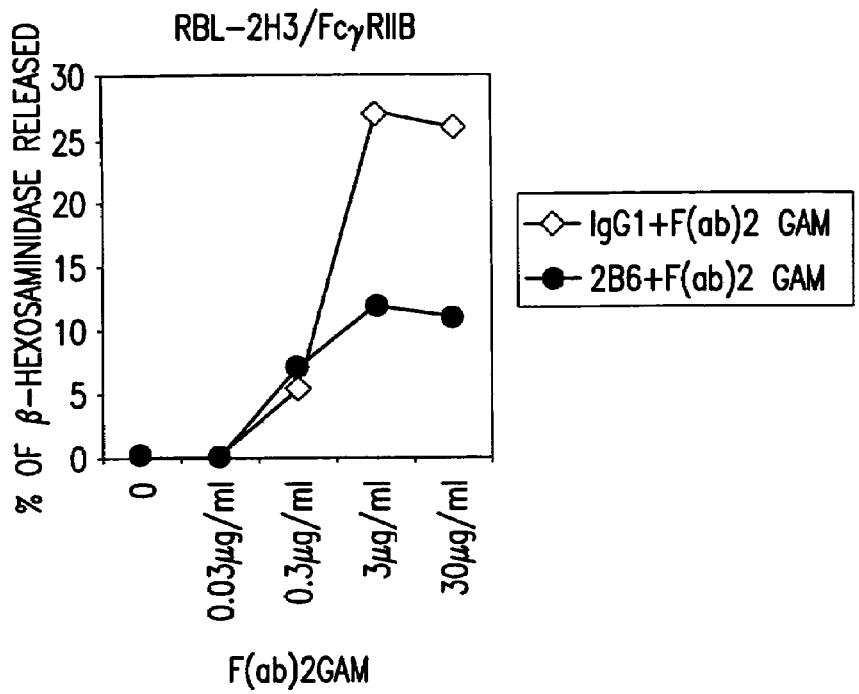
Figure 12B:
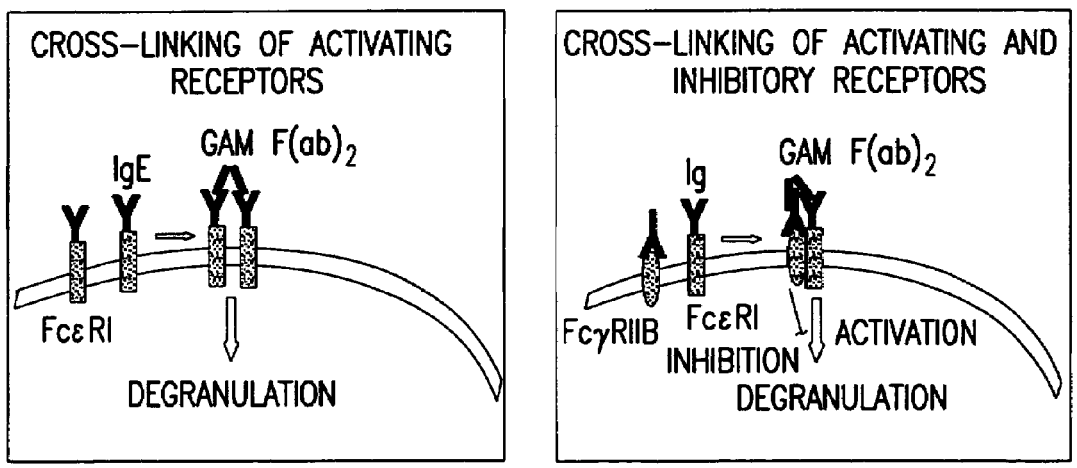

FIGS. 12A and 12B: β-Hexaminidase Release Assay.

A. Schematic representation of α-hexaminidase release assay, (FIG. 12B) Transfectants expressing human FcγRIIB were sensitized with mouse IgE and challenged with F(ab')$_2$ fragments of a polyclonal goat anti-mouse IgG to aggregate FcεRI. Crosslinking occurs because of the ability of the polyclonal antibody to recognize the light chain of the murine IgE antibody bound to FcεRI. Transfectants sensitized with murine IgE and preincubated with 2B6 antibody were also challenged with F(ab')$_2$ fragments of a polyclonal goat anti-mouse IgG to cross link FcεRI to FcγRIIB.

B. β-hexosaminidase release induced by goat anti-mouse F(ab')$_2$ fragment (GAM F(ab)$_2$) in RBL-2H3 cells expressing huFcγRIIB (FIG. 12A). Cells were stimulated with various concentration of GAM F(ab)$_2$ (0.03 µg/ml to 30 µg/ml) after sensitization with mouse IgE (0.01 µg/ml) and IgG1 or with purified 2B6 antibody (3 µg/ml) panel. After 1 hour at 37° C. the supernatant was collected and cells were lysed. β-hexosaminidase activity released in the supernatant and within the cells was determined by a colorimetric assay using p-nitrophenyl N-acteyl-β-D-glucosaminide. The released β-hexosaminidase activity was expressed as a percentage of the released activity relative to the total activity.

Figure 13A:
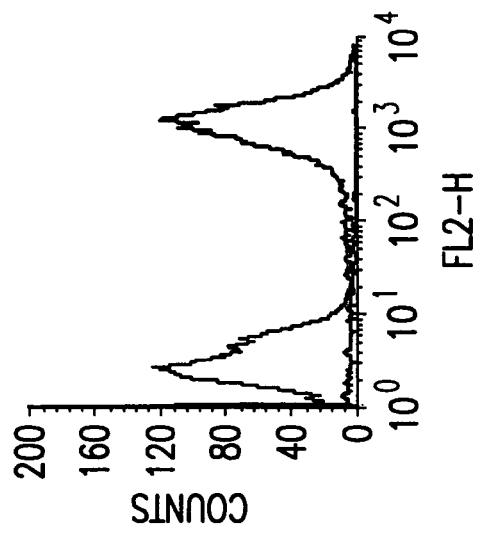
Figure 13B:
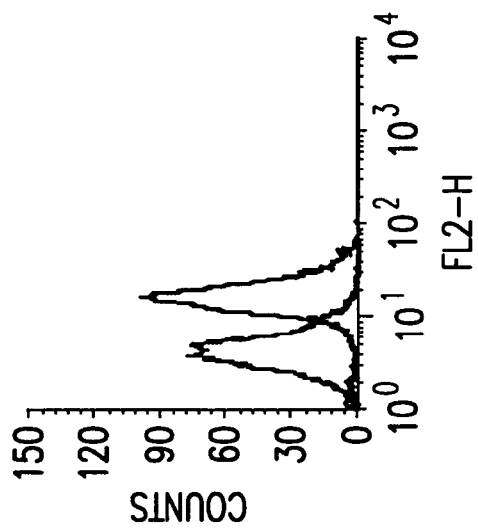
Figure 13C:
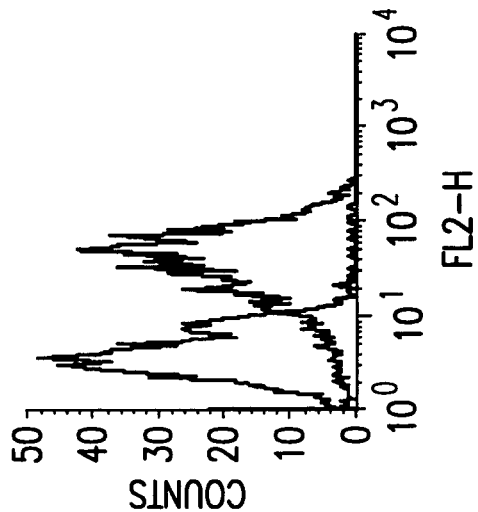

FIGS. 13A-13C: Ovarian and Breast carcinoma cell lines express Her2/neu to varying levels.

Staining of Ovarian IGROV-1 (FIG. 13A) with purified ch4D5, Ovarian OVCAR-8 (FIG. 13B) with purified 4D5 antibody, and Breast cancer SKBR-3 (FIG. 13C) cells with purified ch4D5 followed by goat anti-human-conjugated to phycoerythrin (PE). The relevant isotype control IgG1 is indicated the left of the staining with anti-Her2/neu antibody.

Figure 14A:
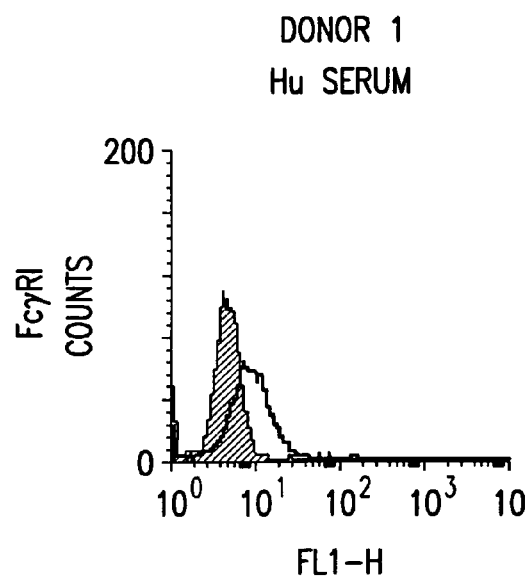
Figure 14B:
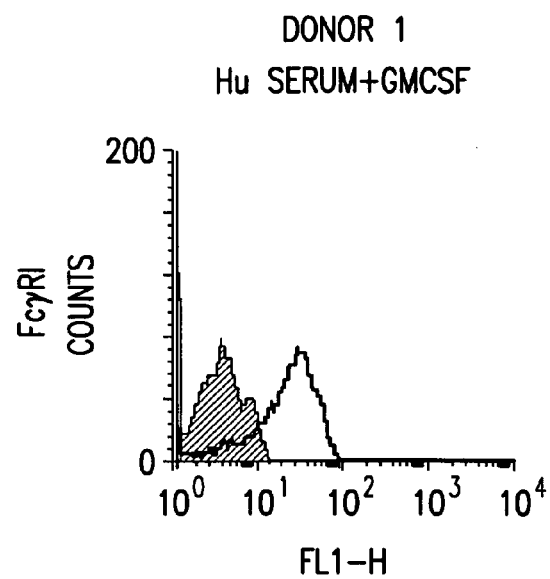
Figure 14C:
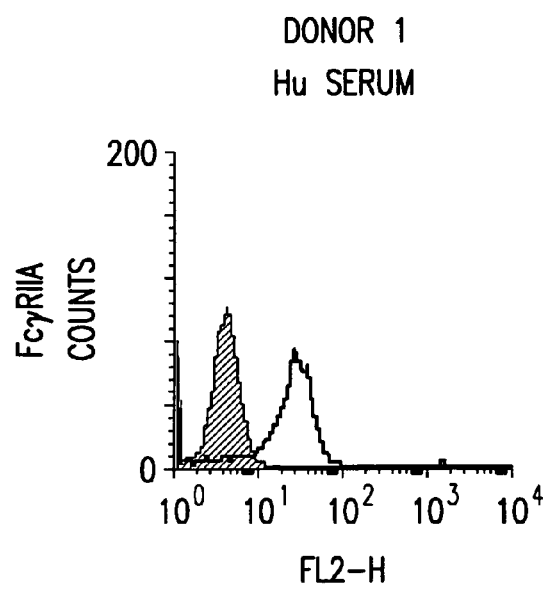
Figure 14D:
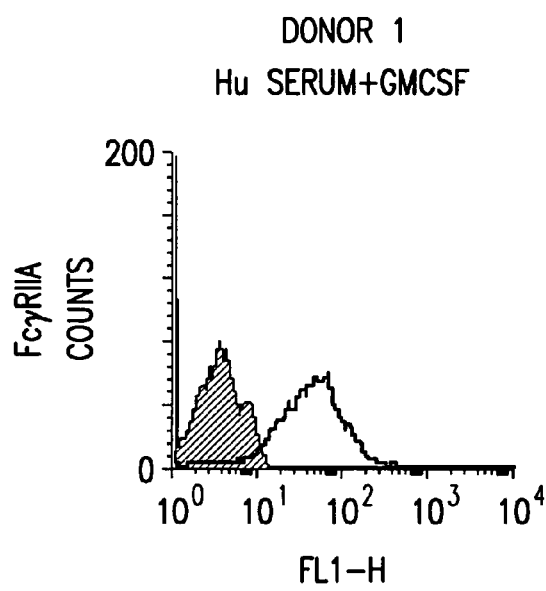
Figure 14E:
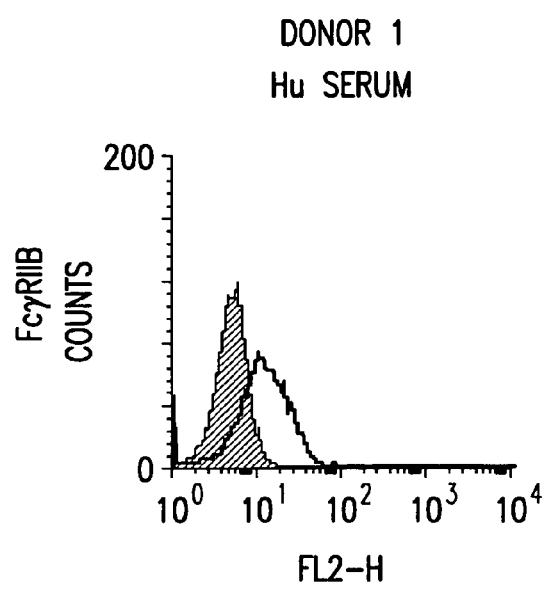
Figure 14F:
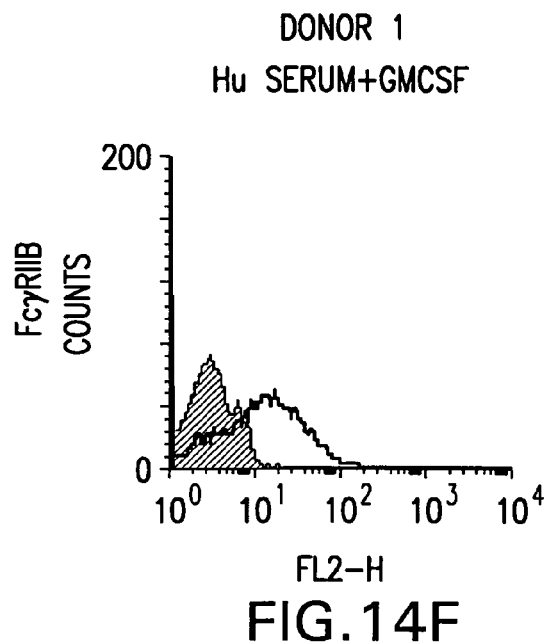
Figure 14G:
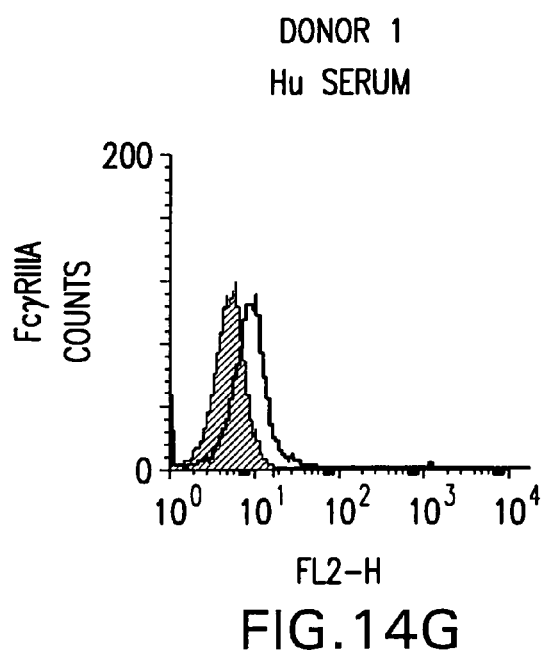
Figure 14H:
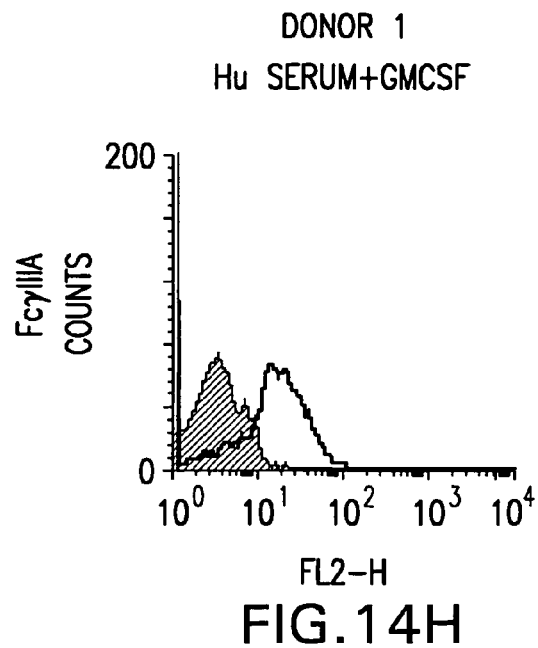
Figure 14I:
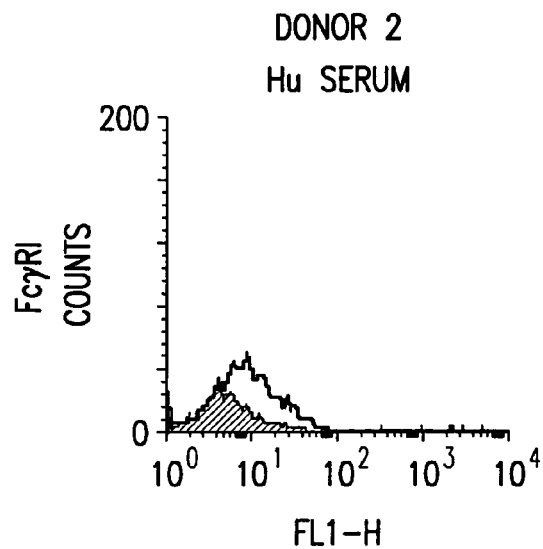
Figure 14J:
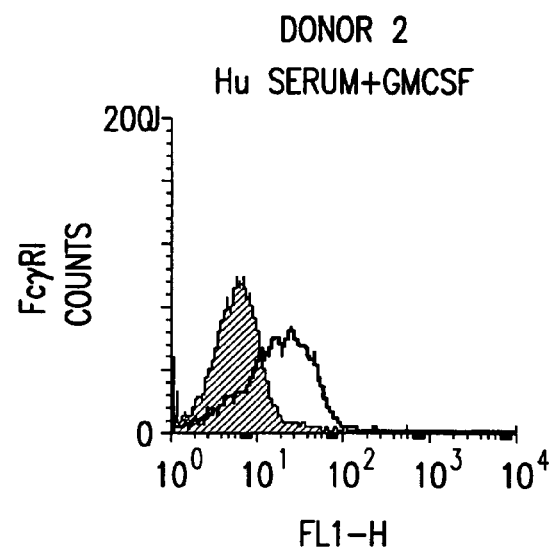
Figure 14K:
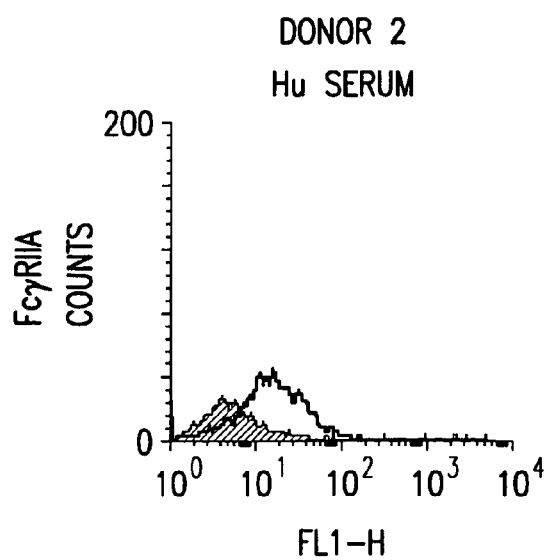
Figure 14L:
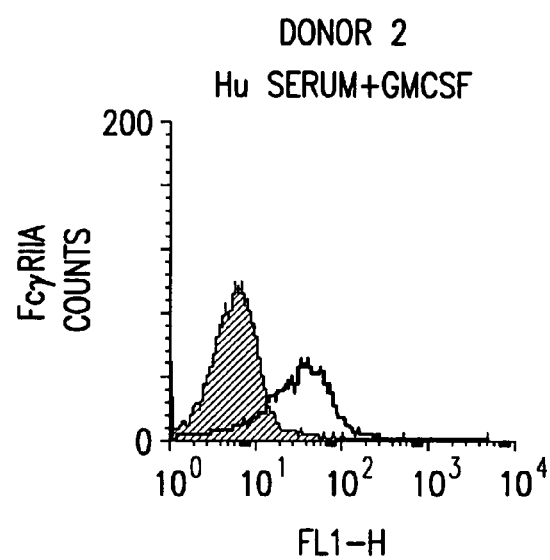
Figure 14M:
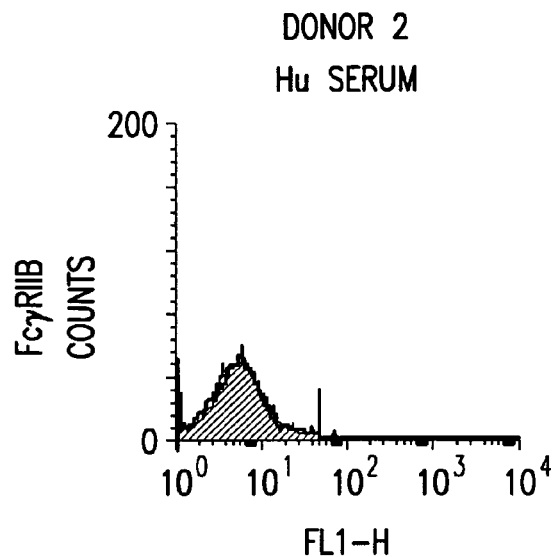
Figure 14N:
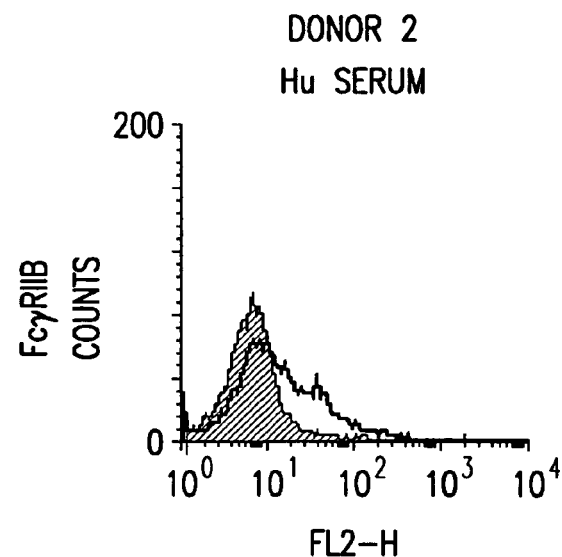
Figure 14O:
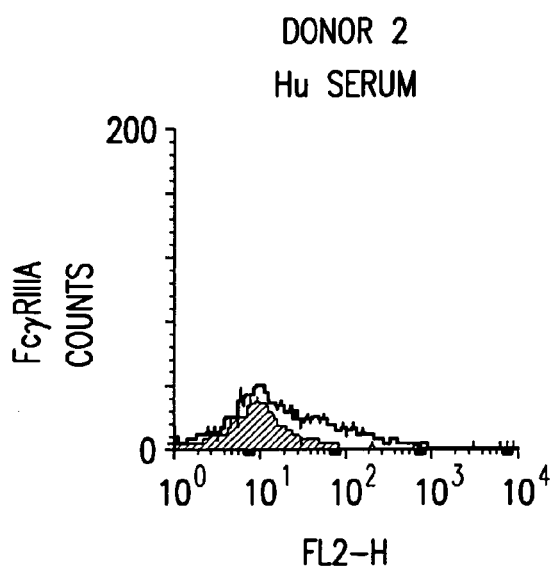
Figure 14P:
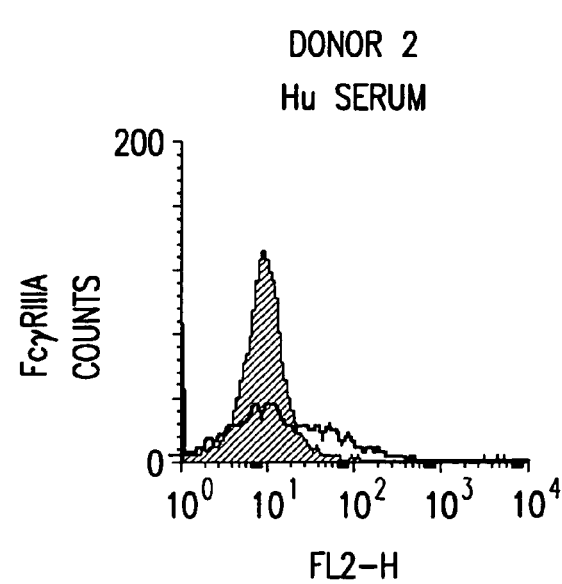

FIGS. 14A-T: Eluriated Monocytes express all FcγRs:
A. MDM obtained from donor 1, propagated in human serum (FIGS. 14A, 14C, 14E and 14G) or human serum and GMCSF (FIGS. 14B, 14D, 14F and 14H);
B. MDM obtained from donor 2, propagated in human serum (FIGS. 14I, 14K, 14M and 14O) or human serum and GMCSF (FIGS. 14J, 14L, 14N and 14P);
C. Monocytes thawed and stained immediately (FIGS. 14Q-14T).

Monocyte-derived macrophages were stained with antibodies specific for human FcγR receptor. The solid histogram in each plot represents the background staining. The clear histogram within each panel represents the staining with specific anti-human FcγR antibodies.

Figure 15A:
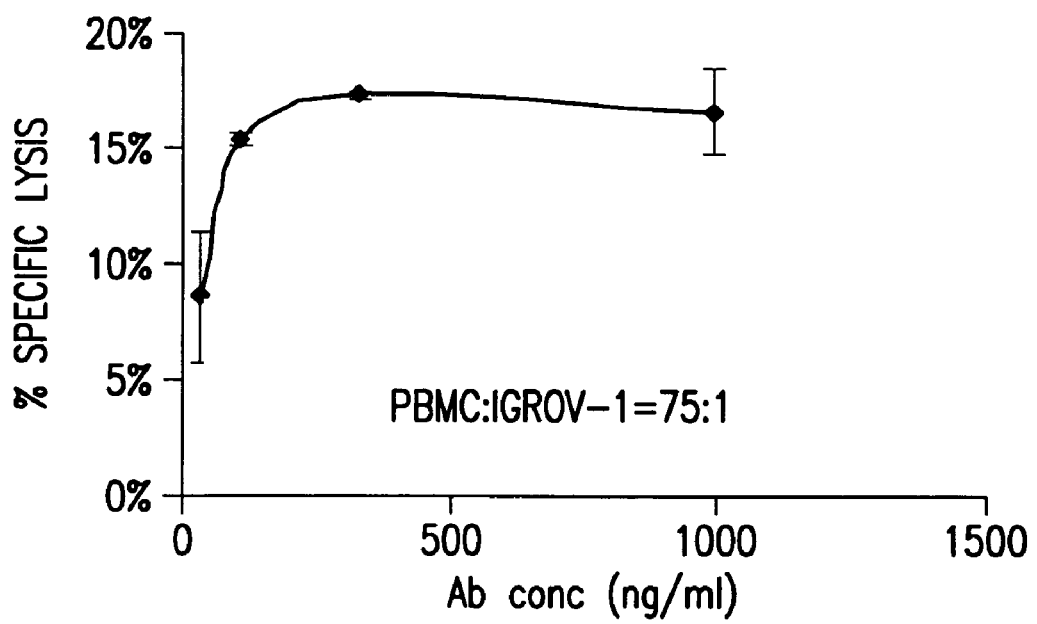
Figure 15B:
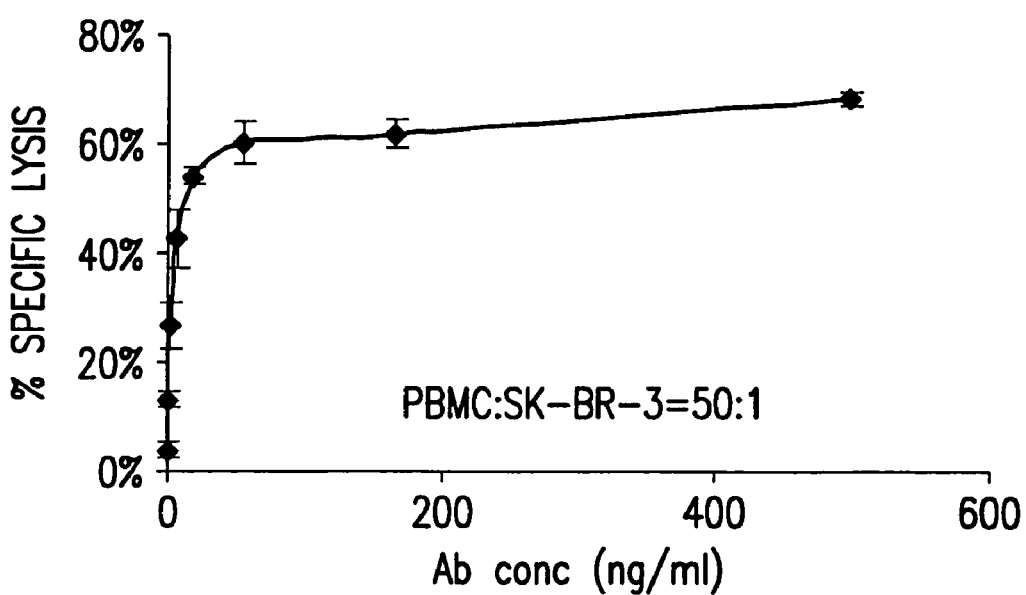

FIGS. 15A-15B: Ch4D5 mediates effective ADCC with ovarian and breast cancer cell lines using PBMC. Specific lysis subtracted from antibody-independent lysis is shown (for FIG. 15A) Ovarian tumor cell line, IGROV-1 at an effector: target ratio of 75:1, and (for FIG. 15B) Breast tumor cell line SKBR-3 at an effector:target ratio of 50:1 with different concentration of ch4D5 as indicated.

Figure 16C:
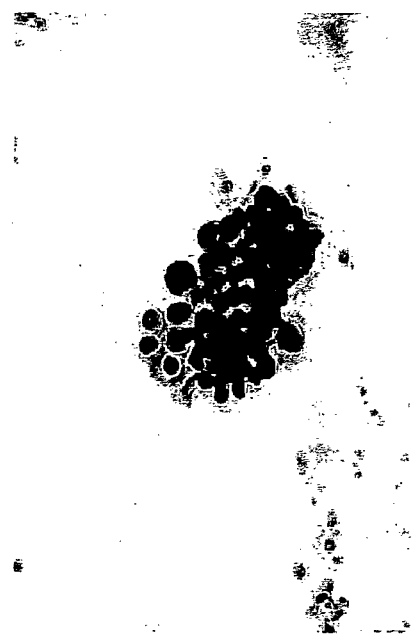
Figure 16B:
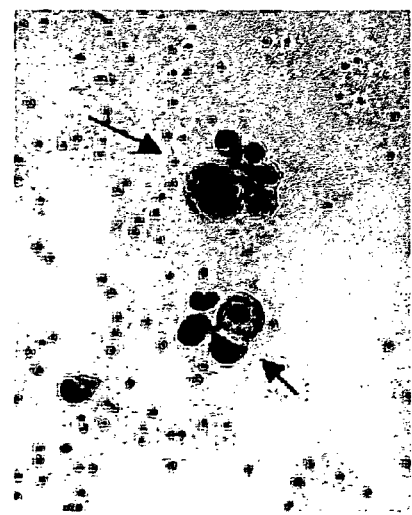
Figure 16A:
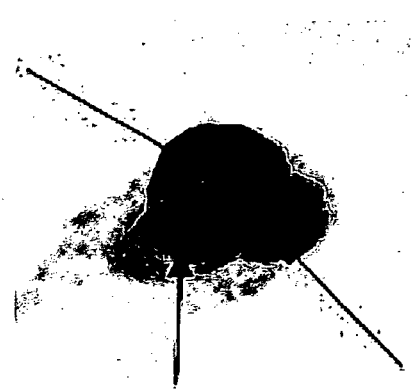

FIGS. 16A-16C: Histochemical staining of human ovarian ascites shows tumors cells and other inflammatory cells. (FIG. 16A). H & E stain on ascites of a patient with ovarian tumor. Three neoplastic cells can be identified by the irregular size and shape, scattered cytoplasm, and irregular dense nuclei. (FIG. 16B). Giemsa stain of unprocessed ascites from a patient with serous tumor of the ovary shows two mesothelial cells placed back to back indicated by short arrows. Also shown is a cluster of five malignant epithelial cells indicated by the long arrow. Erythrocytes are visible in the background. (FIG. 16C). Giemsa stain of another patient with serous tumor of the ovary indicating a cluster of cells composed of mesothelial cells, lymphocytes, and epithelial neoplastic cells (arrow).

5. DESCRIPTION OF THE PREFERRED EMBODIMENTS

5.1 FcγRIIB-Specific Antibodies

The invention encompasses antibodies (preferably monoclonal antibodies) or fragments thereof that specifically bind FcγRIIB, preferably human FcγRIIB, more preferably native human FcγRIIB with a greater affinity than said antibodies or fragments thereof bind FcγRIIA, preferably human FcγRIIA, more preferably native human FcγRIIA. Preferably, the antibodies of the invention bind the extracellular domain of native human FcγRIIB. In certain embodiments, the antibodies or fragments thereof bind to FcγRIIB with an affinity greater than two-fold, four fold, 6 fold, 10 fold, 20 fold, 50 fold, 100 fold, 1000 fold, $10^4$ fold, $10^5$ fold, $10^6$ fold, $10^7$ fold, or $10^8$ fold than said antibodies or fragments thereof bind FcγRIIA. In one particular embodiment, the antibody is a mouse monoclonal antibody produced by clone 2B6 or 3H7, having ATCC accession numbers PTA-4591 and PTA-4592, respectively. Hybridomas producing antibodies of the invention have been deposited with the American Type Culture Collection (10801 University Blvd., Manassas, Va. 20110-2209) on Aug. 13, 2002 under the provisions of the Budapest Treaty on the International Recognition of the Deposit of Microorganisms for the Purposes of Patent Procedures, and assigned accession numbers PTA-4591 (for hybridoma producing 2B6) and PTA-4592 (for hybridoma producing 3H7), respectively and are incorporated herein by reference. In a specific embodiment, the invention encompasses an antibody with the heavy chain having the amino acid sequence of SEQ ID No 2 and the light chain having the amino acid sequence of SEQ ID No. 4. In a preferred embodiment, the antibodies of the invention are human or have been humanized, preferably a humanized version of the antibody produced by clone 3H7 or 2B6. In yet another preferred embodiment, the antibodies of the invention further do not bind Fc activation receptors, e.g., FcγIIIA, FcγIIIB, etc. In one embodiment, the FcγRIIB-specific antibody in accordance with the invention is not the monoclonal antibody designated KB61, as disclosed in Pulford et al., 1986 (*Immunology*, 57: 71-76) or the monoclonal antibody designated MAbII8D2 as disclosed in Weinrich et al., 1996, (*Hybridoma*, 15(2):109-6). In a specific embodiment, the FcγRIIB-specific antibody of the invention does not bind to the same epitope and/or does not compete with binding with the monoclonal antibody KB61 or 118D2. Preferably, the FcγRIIB-specific antibody of the invention does not bind the amino acid sequence SDPNFSI (SEQ ID NO:5) corresponding to positions 135-141 of FcγRIIb2 isoform.

The invention also encompasses other antibodies, preferably monoclonal antibodies or fragments thereof that specifically bind FcγRIIB, preferably human FcγRIIB, more preferably native human FcγRIIB, produced by clones including but not limited to 1D5, 2E1, 2H9, 2D11, and 1F2 having ATCC Accession numbers, PTA-5958, PTA-5961, PTA-5962, PTA-5962, PTA-5960, and PTA-5959, respectively. Hybridomas producing the above-identified clones were deposited with the American Type Culture Collection (10801 University Blvd., Manassas, Va. 20110-2209) on May 7, 2004 and are incorporated herein by reference.

In a particular embodiment, the antibodies of the invention, or fragments thereof agonize at least one activity of FcγRIIIB. In one embodiment of the invention, said activity is inhibition of B cell receptor-mediated signaling. In another embodiment, the agonistic antibodies of the invention inhibit activation of B cells, B cell proliferation, antibody production, intracellular calcium influx of B cells, cell cycle progression, or activity of one or more downstream signaling molecules in the FcγRIIB signal transduction pathway. In yet another embodiment, the agonistic antibodies of the invention enhance phosphorylation of FcγRIIB or SHIP recruitment. In a further embodiment of the invention, the agonistic antibodies inhibit MAP kinase activity or Akt recruitment in the B cell receptor-mediated signaling pathway. In another embodiment, the agonistic antibodies of the invention agonize FcγRIIB-mediated inhibition of FcεRI signaling. In a particular embodiment, said antibodies inhibit FcεRI-induced mast cell activation, calcium mobilization, degranulation, cytokine production, or serotonin release. In another embodiment, the agonistic antibodies of the invention stimulate phosphorylation of FcγRIIB, stimulate recruitment of SHIP, stimulate SHIP phosphorylation and its association with Shc, or inhibit activation of MAP kinase family members (e.g., Erk1, Erk2, JNK, p38, etc.). In yet another embodiment, the agonistic antibodies of the invention enhance tyrosine phosphorylation of p62dok and its association with SHIP and rasGAP. In another embodiment, the agonistic antibodies of the invention inhibit FcγR-mediated phagocytosis in monocytes or macrophages.

In another embodiment, the antibodies of the invention, or fragments thereof antagonize at least one activity of FcγRIIB. In one embodiment, said activity is activation of B cell receptor-mediated signaling. In a particular embodiment, the antagonistic antibodies of the invention enhance B cell activity, B cell proliferation, antibody production, intracellular calcium influx, or activity of one or more downstream signaling molecules in the FcγRIIB signal transduction pathway. In yet another particular embodiment, the antagonistic antibodies of the invention decrease phosphorylation of FcγRIIIB or SHIP recruitment. In a further embodiment of the invention, the antagonistic antibodies enhance MAP kinase activity or Akt recruitment in the B cell receptor mediated signaling pathway. In another embodiment, the antagonistic antibodies of the invention antagonize FcγRIIB-mediated inhibition of FcεRI signaling. In a particular embodiment, the antagonistic antibodies of the invention enhance FcεRI-induced mast cell activation, calcium mobilization, degranulation, cytokine production, or serotonin release. In another embodiment, the antagonistic antibodies of the invention inhibit phosphorylation of FcγRIIB, inhibit recruitment of SHIP, inhibit SHIP phosphorylation and its association with Shc, enhance activation of MAP kinase family members (e.g., Erk1, Erk2, JNK, p38, etc.). In yet another embodiment, the antagonistic antibodies of the invention inhibit tyrosine phosphorylation of p62dok and its association with SHIP and rasGAP. In another embodiment, the antagonistic antibodies of the invention enhance FcγR-mediated phagocytosis in monocytes or macrophages. In another embodiment, the antagonistic antibodies of the invention prevent phagocytosis, clearance of opsonized particles by splenic macrophages.

Antibodies of the invention include, but are not limited to, monoclonal antibodies, synthetic antibodies, recombinantly produced antibodies, multispecific antibodies, human antibodies, humanized antibodies, chimeric antibodies, camelized antibodies, single-chain Fvs (scFv), single chain antibodies, Fab fragments, F(ab') fragments, disulfide-linked Fvs (sdFv), intrabodies, and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to FcγRIIB with greater affinity than said immunoglobulin molecule binds FcγRIIA.

The antibodies used in the methods of the invention may be from any animal origin including birds and mammals (e.g., human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The antibodies used in the methods of the present invention may be monospecific, bispecific, trispecific or of greater multispecificity. Multispecific antibodies may immunospecifically bind to different epitopes of FcγRII or immunospecifically bind to both an epitope of FcγRIIB as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553; Todorovska et al, 2001 Journal of Immunological Methods, 248:47-66.

In particular embodiments, the antibodies of the invention are multi-specific with specificities for FcγRIIB and for a cancer antigen or any other cell surface marker specific for a cell designed to be killed, e.g., in treating or preventing a particular disease or disorder, or for other Fc receptors, e.g., FcγRIIIA, FcγRIIIB, etc.

In a specific embodiment, an antibody used in the methods of the present invention is an antibody or an antigen-binding fragment thereof (e.g., comprising one or more complementarily determining regions (CDRs), preferably all 6 CDRs) of the antibody produced by clone 2B6 or 3H7 with ATCC accession numbers PTA-4591 and PTA-4592, respectively (e.g., the heavy chain CDR3). In another embodiment, an antibody used in the methods of the present invention binds to the same epitope as the mouse monoclonal antibody produced from clone 2B6 or 3H7 with ATCC accession numbers PTA-4591 and PTA-4592, respectively and/or competes with the mouse monoclonal antibody produced from clone 2B6 or 3H7 with ATCC accession numbers PTA-4591 and PTA-4592, respectively as determined, e.g., in an ELISA assay or other appropriate competitive immunoassay, and also binds FcγRIIB with a greater affinity than said antibody or a fragment thereof binds FcγRIIA.

The antibodies used in the methods of the invention include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

For some uses, including in vivo use of antibodies in humans and in vitro detection assays, it may be preferable to use human, chimeric or humanized antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al, 1989, *J. Immunol. Methods* 125:191-202; and U.S. Pat. Nos. 6,311,415, 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, *Molecular Immunology* 28(4/5):489-498; Studnicka et al, 1994, *Protein Engineering* 7:805; and Roguska et al., 1994, *PNAS* 91:969), and chain shuffling (U.S. Pat. No. 5,565,332). Each of the above-identified references is incorporated herein by reference in its entirety.

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, *Nature* 332:323, which are incorporated herein by reference in their entireties.)

A humanized antibody is an antibody, a variant or a fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *PNAS* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, *Nature* 332:323, which are incorporated herein by reference in their entireties.)

Further, the antibodies of the invention can, in turn, be utilized to generate anti-idiotype antibodies using techniques well known to those skilled in the art. (See, e.g., Greenspan & Bona, 1989, *FASEB J.* 7:437-444; and Nissinoff, 1991, *J. Immunol.* 147:2429-2438). The invention provides methods employing the use of polynucleotides comprising a nucleotide sequence encoding an antibody of the invention or a fragment thereof.

The present invention encompasses single domain antibodies, including camelized single domain antibodies (See e.g., Muyldermans et al., 2001, *Trends Biochem. Sci.* 26:230; Nuttall et al, 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079; which are incorporated herein by reference in their entireties). In one embodiment, the present invention provides single domain antibodies comprising two VH domains with modifications such that single domain antibodies are formed.

The methods of the present invention also encompass the use of antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The antibodies of the invention may be engineered by methods described in Ward et al. to increase biological half-lives (See U.S. Pat. No. 6,277,375 B1). For example, antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies of the invention may also be modified by the methods and coupling agents described by Davis et al. (See U.S. Pat. No. 4,179,337) in order to provide compositions that can be injected into the mammalian circulatory system with substantially no immunogenic response.

The present invention also encompasses the use of antibodies or antibody fragments comprising the amino acid sequence of any of the antibodies of the invention with mutations (e.g., one or more amino acid substitutions) in the framework or variable regions. Preferably, mutations in these antibodies maintain or enhance the avidity and/or affinity of the antibodies for the particular antigen(s) to which they immunospecifically bind. Standard techniques known to those skilled in the art (e.g., immunoassays) can be used to assay the affinity of an antibody for a particular antigen.

The present invention encompasses antibodies comprising modifications preferably, in the Fc region that modify the binding affinity of the antibody to one or more FcγR. Methods for modifying antibodies with modified binding to one or more FcγR are known in the art, see, e.g., PCT Publication Nos. WO 99/58572, WO 99/51642, WO 98/23289, WO 89/07142, WO 88/07089, and U.S. Pat. Nos. 5,843,597 and 5,642,821, each of which is incorporated herein by reference in their entirety. The invention encompasses any of the mutations disclosed in U.S. Application Nos. 60/439,498 and 60/456,041, filed Jan. 9, 2003 and Mar. 19, 2003, respectively each of which is incorporated herein by reference in their entirety. In some embodiments, the invention encompasses antibodies that have altered affinity for an activating FcγR, e.g., FcγRIIIA. Preferably such modifications also have an altered Fc-mediated effector function. Modifications that affect Fc-mediated effector function are well known in the art (See U.S. Pat. No. 6,194,551, which is incorporated herein by reference in its entirety). The amino acids that can be modified in accordance with the method of the invention include but are not limited to Proline 329, Proline 331, and Lysine 322. Proline 329, 331 and Lysine 322 are preferably replaced with alanine, however, substitution with any other amino acid is contemplated. See International Publication No.: WO 00/42072 and U.S. Pat. No. 6,194,551 which are incorporated herein by reference in their entirety.

In one particular embodiment, the modification of the Fc region comprises one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof.

The invention also provides antibodies with altered oligosaccharide content. Oligosaccharides as used herein refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al., 1981 *Ann. Rev. Biochem.*, 50: 555-583, which is incorporated herein by reference in its entirety. This nomenclature includes for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetyl-neuraminic acid, and NeuNGc for 5-glycolneuraminic.

In general, antibodies contain carbohydrate moeities at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, *Immunol. Rev.* 163: 59-76; Wright et al., 1997, *Trends Biotech* 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al., 2001 *Bichem. Biophys. Res. Commun.* 288: 243-9; Groenink et al., 1996 *J. Immunol.* 26: 1404-7; Boyd et al., 1995 *Mol. Immunol.* 32: 1311-8; Kumpel et al., 1994, *Human Antibody Hybridomas,* 5: 143-51. The invention encompasses antibodies comprising a variation in the carbohydrate moiety that is attached to Asn 297. In one embodiment, the carbohydrate moiety has a galactose and/or galactose-sialic acid at one or both of the terminal GlcNAc and/or a third GlcNac arm (bisecting GlcNAc).

In some embodiments, the antibodies of the invention are substantially free of one or more selected sugar groups, e.g., one or more sialic acid residues, one or more galactose residues, one or more fucose residues. An antibody that is substantially free of one or more selected sugar groups may be prepared using common methods known to one skilled in the art, including for example recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such antibodies include for example, culturing cells under conditions which prevent or reduce the addition of one or more selected sugar groups, or post-translational removal of one or more selected sugar groups.

In a specific embodiment, the invention encompasses a method of producing a substantially homogenous antibody preparation, wherein about 80-100% of the antibody in the composition lacks a fucose on its carbohydrate moiety, e.g., the carbohydrate attachment on Asn 297. The antibody may be prepared for example by (a) use of an engineered host cell that is deficient in fucose metabolism such that it has a reduced ability to fucosylate proteins expressed therein; (b) culturing cells under conditions which prevent or reduce fusocylation; (c) post-translational removal of fucose, e.g., with a fucosidase enzyme; or (d) purification of the antibody so as to select for the product which is not fucosylated. Most preferably, nucleic acid encoding the desired antibody is expressed in a host cell that has a reduced ability to fucosylate the antibody expressed therein. Preferably the host cell is a dihydrofolate reductase deficient chinese hamster ovary cell (CHO), e.g., a Lee 13 CHO cell (lectin resistant CHO mutant cell line; Ribka & Stanley, 1986, *Somatic Cell & Molec. Gen.* 12(1): 51-62; Ripka et alt, 1986 *Arch. Biochem. Biophys.* 249(2): 533-45), CHO-K1, DUX-B11, CHO-DP12 or CHO-DG44, which has been modified so that the antibody is not substantially fucosylated. Thus, the cell may display altered expression and/or activity for the fucoysltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al., 2002, *J. Biol. Chem.* 277(30): 26733-40; both of which are incorporated herein by reference in their entirety.

In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for e.g., see Shields R. L. et al., 2001, *J. Biol. Chem.* 277(30): 26733-40; Davies J. et al., 2001, *Biotechnology & Bioengineering*, 74(4): 288-294). In another specific embodiment, the altered carbohydrate modifications enhance the binding of antibodies of the invention to FcγRIIB receptor. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, *Journal of Exp. Med.* 168(3): 1099-1109; Tao et al., 1989 *Journal of Immunology*, 143(8): 2595-2601; Routledge et al., 1995 Transplantation, 60(8): 847-53; Elliott et al. 2003; *Nature Biotechnology*, 21: 414-21; Shields et al. 2002 *Journal of Biological Chemistry*, 277(30): 26733-40; all of which are incorporated herein by reference in their entirety.

In some embodiments, the invention encompasses antibodies comprising one or more glycosylation sites, so that one or more carbohydrate moieties are covalently attached to the antibody. In other embodiments, the invention encompasses antibodies comprising one or more glycosylation sites and one or more modifications in the Fc region, such as those disclosed supra and those known to one skilled in the art. In preferred embodiments, the one or more modifications in the Fc region enhance the affinity of the antibody for an activating FcγR, e.g., FcγRIIIA, relative to the antibody comprising the wild type Fc regions. Antibodies of the invention with one or more glycosylation sites and/or one or more modifications in the Fc region have an enhanced antibody mediated effector function, e.g., enhanced ADCC activity. In some embodiments, the invention further comprises antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

The invention encompasses antibodies that have been modified by introducing one or more glycosylation sites into one or more sites of the antibodies, preferably without altering the functionality of the antibody, e.g., binding activity to FcγRIIB. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "*In Vitro Mutagenesis*," *Recombinant DNA: A Short Course*, J. D. Watson, et al. W.H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody.

The invention further encompasses methods of modifying an effector function of an antibody of the invention, wherein the method comprises modifying the carbohydrate content of the antibody using the methods disclosed herein or known in the art.

Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted non-essential amino acid residues.

The present invention also encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone 2B6 or 3H7 having ATCC accession numbers PTA-4591 and PTA-4592, respectively. The present invention further encompasses antibodies or fragments thereof that specifically bind FcγRIIB with greater affinity than said antibody or fragment thereof binds FcγRIIA, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6 or 3H7 having ATCC accession numbers PTA-4591 and PTA-4592, respectively. The determination of percent identity of two amino acid sequences can be determined by any method known to one skilled in the art, including BLAST protein searches.

The present invention also encompasses the use of antibodies or antibody fragments that specifically bind FcγRIIB with greater affinity than said antibodies or fragments thereof binds FcγRIIA, wherein said antibodies or antibody fragments are encoded by a nucleotide sequence that hybridizes to the nucleotide sequence of the mouse monoclonal antibody produced by clone 2B6 or 3H7 having ATCC accession numbers PTA-4591 and PTA-4592, respectively, under stringent conditions. In a preferred embodiment, the invention provides antibodies or fragments thereof that specifically bind FcγRIIB with greater affinity than said antibodies or fragments thereof bind FcγRIIA, said antibodies or antibody fragments comprising a variable light and/or variable heavy chain encoded by a nucleotide sequence that hybridizes under stringent conditions to the nucleotide sequence of the variable light and/or variable heavy chain of the mouse monoclonal antibody produced by clone 2B6 or 3H7 having ATCC accession numbers PTA-4591 and PTA-4592, respectively, under stringent conditions. In another preferred embodiment, the invention provides antibodies or fragments thereof that specifically bind FcγRIIB with greater affinity than said antibodies or fragments thereof bind FcγRIIA, said antibodies or antibody fragments comprising one or more CDRs encoded by a nucleotide sequence that hybridizes under stringent conditions to the nucleotide sequence of one or more CDRs of the mouse monoclonal antibody produced by clone 2B6 or 3H7 with ATCC accession numbers PTA-4591 and PTA-4592, respectively. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 *Current Protocols in Molecular Biology*, vol. 1, Green Publishing Associates, Inc. and John Wiley and Sons, Inc., NY at pages 6.3.1 to 6.3.6 and 2.10.3), incorporated herein by reference.

5.1.1 Antibody Conjugates

The present invention encompasses antibodies recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Antibodies may be used for example to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT publication Number WO 93/2 1232; EP 439,095; Naramura et al., *Immunol. Lett.*, 39:91-99, 1994; U.S. Pat. No. 5,474,981; Gillies et al., *PNAS*, 89:1428-1432, 1992; and Fell et al., *J. Immunol.*, 146:2446-2452, 1991, which are incorporated herein by reference in their entireties.

Further, an antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.*, 6:1567-1574, 1994), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH"); proteases, or ribonucleases.

Antibodies can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA*, 86:821-824, 1989, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell*, 37:767 1984) and the "flag" tag (Knappik et al., *Biotechniques*, 17(4):754-761, 1994).

The present invention further includes compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al., 1991, *PNAS* 88: 10535-10539; Zheng et al., 1995, *J. Immunol.* 154:5590-5600; and Vil et al., 1992, *PNAS* 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to FcγRIIB may be recombined with one or more components, motifs, sections, parts, domains, fragments, etc. of one or more heterologous molecules.

The present invention also encompasses antibodies conjugated to a diagnostic or therapeutic agent or any other molecule for which serum half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidinbiotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{116}$Ho), indium ($^{115}$In, $^{112}$In, $^{111}$In), iodine ($^{131}$I, $^{125}$I, $^{123}$I, $^{121}$I) lanthanium ($^{14}$La), lutetium ($^{77}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^3$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

An antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol* 26:943-50 each incorporated by reference in their entireties.

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol Rev.*, 62:119-58, 1982.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2 Immunizing, Screening, Identification of Antibodies and Characterization of Monoclonal Antibodies of the Invention Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas*, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

In one particular embodiment, the invention provides a method for producing monoclonal antibodies that specifically bind FcγRIIB with greater affinity than said monoclonal antibodies-bind FcγRIIA comprising: immunizing one or more FcγRIIA transgenic mice (See U.S. Pat. No. 5,877,396 and U.S. Pat. No. 5,824,487) with the purified extracellular domain of human FcγRIIB, amino acids 1-180; producing hybridoma cell lines from spleen cells of said mice, screening said hybridoma cells lines for one or more hybridoma cell lines that produce antibodies that specifically bind FcγRIIB with greater affinity than said antibodies bind FcγRIIA. In another specific embodiment, the invention provides a method for producing FcγRIIB monoclonal antibodies that specifically bind FcγRIIB, particularly human FcγRIIB, with a greater affinity than said monoclonal antibodies bind FcγRIIA, said method further comprising: immunizing one or more FcγRIIA transgenic mice with purified FcγRIIB or an immunogenic fragment thereof, booster immunizing said mice sufficient number of times to elicit an immune response, producing hybridoma cells lines from spleen cells of said one or more mice, screening said hybridoma cell lines for one or more hybridoma cell lines that produce antibodies that specifically bind FcγRIIB with a greater affinity than said antibodies bind FcγRIIA. In one embodiment of the invention, said mice are immunized with purified FcγRIIB which has been mixed with any adjuvant known in the art to enhance immune response. Adjuvants that can be used in the methods of the invention include, but are not limited to, protein adjuvants; bacterial adjuvants, e.g., whole bacteria (BCG, *Corynebacterium parvum, Salmonella* minnesota) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al., 1999, *Autoimmunity*, 31(1):15-24, which is incorporated herein by reference), MPL® (Corixa Corporation; See also Lodmell D. I. et al., 2000 *Vaccine*, 18: 1059-1066; Ulrich et al., 2000, *Methods in Molecular Medicine*, 273-282; Johnson et al., 1999, *Journal of Medicinal Chemistry*, 42: 4640-4649; Baldridge et al., 1999 *Methods*, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al., 1998, *Clin. Cancer Res*, 4(3):619-27; and Gubta R. et al, 1995, *Vaccine*, 13(14):1263-76 both of which are incorporated herein by reference.)

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., *J. Immunol. Methods,* 182:41-50, 1995; Ames et al., *J. Immunol. Methods,* 184:177-186, 1995; Kettleborough et al., *Eur. J. Immunol.,* 24:952-958, 1994; Persic et al., *Gene,* 187:9-18, 1997; Burton et al., *Advances in Immunology,* 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques,* 12(6):864-869, 1992; and Sawai et at, *AJRI,* 34:26-34, 1995; and Better et al., *Science,* 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., *Methods in Enzymology,* 203:46-88, 1991; Shu et al., *PNAS,* 90:7995-7999, 1993; and Skerra et al., *Science,* 240:1038-1040, 1988.

Phage display technology can be used to increase the affinity of an antibody of the invention for FcγRIIB. This technique would be useful in obtaining high affinity antibodies that could be used in the combinatorial methods of the invention. The technology, referred to as affinity maturation, employs mutagenesis or CDR walking and re-selection using FcγRIIB or an antigenic fragment thereof to identify antibodies that bind with higher affinity to the antigen when compared with the initial or parental antibody (See, e.g., Glaser et al., 1992, *J. Immunology* 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al., 1998, *Proc Natl. Acad. Sci. USA* 95:6037; Yelton et al., 1995, *J. Immunology* 155:1994). CDR walking which randomizes the light chain is also possible (See Schier et al., 1996, *J. Mol. Bio.* 263:551).

Antibodies of the invention may be further characterized by epitope mapping, so that antibodies may be selected that have the greatest specificity for FcγRIIB compared to FcγRIIA. Epitope mapping methods of antibodies are well known in the art and encompassed within the methods of the invention. In certain embodiments fusion proteins comprising one or more regions of FcγRIIB may be used in mapping the epitope of an antibody of the invention. In a specific embodiment, the fusion protein contains the amino acid sequence of a region of an FcγRIIB fused to the Fc portion of human IgG2. Each fusion protein may further comprise amino acid substitutions and/or replacements of certain regions of the receptor with the corresponding region from a homolog receptor, e.g., FcγRIIA, as shown in Table 2 below. pMGX125 and pMGX132 contain the IgG binding site of the FcγRIIB receptor, the former with the C-terminus of FcγIIB and the latter with the C-terminus of FcγRIIA and can be used to differentiate C-terminus binding. The others have FcγRIIA substitutions in the IgG binding site and either the FcγIIA or FcγIIB N-terminus. These molecules can help determine the part of the receptor molecule where the antibodies bind.

TABLE 2

List of the fusion proteins that may be used to investigate the epitope of the monoclonal anti-FcγRIIB antibodies. Residues 172 to 180 belong to the IgG binding site of FcγRIIA and B. The specific amino acids from FcγRIIA sequence are in bold.

| Plasmid | Receptor | N-terminus | 172-180 | C-terminus |
|---|---|---|---|---|
| pMGX125 | RIIb | IIb | KKFSRSDPN (SEQ ID NO:6) | APS---SS (IIb) (SEQ ID NO:12) |
| pMGX126 | RIIa/b | IIa | QKFSRLDPN (SEQ ID NO:7) | APS---SS (IIb) (SEQ ID NO:12) |
| pMGX127 | | IIa | QKFSRLDPT (SEQ ID NO:8) | APS---SS (IIb) (SEQ ID NO:12) |
| pMGX128 | | IIb | KKFSRLDPT (SEQ ID NO:9) | APS---SS (IIb) (SEQ ID NO:12) |
| pMGX129 | | IIa | QKFSHLDPT (SEQ ID NO:10) | APS---SS (IIb) (SEQ ID NO:12) |
| pMGX130 | | IIb | KKFSHLDPT (SEQ ID NO:11) | APS---SS (IIb) (SEQ ID NO:12) |
| pMGX131 | | IIa | QKFSRLDPN (SEQ ID NO:7) | VPSMGSSS(IIa) (SEQ ID NO:13) |
| pMGX132 | | IIb | KKFSRSDPN (SEQ ID NO:6) | VPSMGSSS(IIa) SEQ ID NO:13) |
| pMGX133 | RIIa-131R | IIa | QKFSRLDPT (SEQ ID NO:8) | VPSMGSSS(IIa) SEQ ID NO:13) |
| pMGX134 | RIIa-131H | IIa | QKFSHLDPT (SEQ ID NO:10) | VPSMGSSS(IIa) SEQ ID NO:13) |
| pMGX135 | | IIb | KKFSRLDPT (SEQ ID NO:9) | VPSMGSSS(IIa) SEQ ID NO:13) |
| pMGX136 | | IIb | KKFSHLDPT (SEQ ID NO:11) | VPSMGSSS(IIa) SEQ ID NO:13) |

The fusion proteins may be used in any biochemical assay for determination of binding to an anti-FcγIIB antibody of the invention, e.g., an ELISA. In other embodiments, further confirmation of the epitope specificity may be done by using peptides with specific residues replaced with those from the FcγRIIA sequence.

The antibodies of the invention may be characterized for specific binding to FcγRIIB using any immunological or biochemical based method known in the art for characterizing including quantitating, the interaction of the antibody to FcεRIIB. Specific binding of an antibody of the invention to FcγRIIB may be determined for example using immunological or biochemical based methods including, but not limited to, an ELISA assay, surface plasmon resonance assays, immunoprecipitation assay, affinity chromatography, and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

Antibodies of the invention may also be assayed using any surface plasmon resonance based assays known in the art for characterizing the kinetic parameters of the interaction of the antibody with FcγRIIB. Any SPR instrument commercially available including, but not limited to, BLAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occur is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g. Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

The invention encompasses characterization of the antibodies produced by the methods of the invention using certain characterization assays for identifying the function of the antibodies of the invention, particularly the activity to modulate FcγRIIB signaling. For example, characterization assays of the invention can measure phosphorylation of tyrosine residues in the ITIM motif of FcγRIIB, or measure the inhibition of B cell receptor-generated calcium mobilization. The characterization assays of the invention can be cell-based or cell-free assays.

It has been well established in the art that in mast cells coaggregation of FcγRIIB with the high affinity IgE receptor, FcεRI, leads to inhibition of antigen-induced degranulation, calcium mobilization, and cytokine production (Metcalfe D. D. et al. 1997, *Physiol. Rev.* 77:1033; Long E. O. 1999 *Annu Rev. Immunol* 17: 875). The molecular details of this signaling pathway have been recently elucidated (Ott V. L., 2002, *J. Immunol.* 162(9):4430-9). Once coaggregated with FcγRI, FcγRIIB is rapidly phosphorylated on tyrosine in its ITIM motif, and then recruits Src Homology-2 containing inositol-5-phosphatase (SHIP), an SH2 domain-containing inosital polyphosphate 5-phosphatase, which is in turn phosphorylated and associates with Shc and $p62^{dok}$ ($p62^{dok}$ is the prototype of a family of adaptor molecules, which includes signaling domains such as an aminoterminal pleckstrin homology domain (PH domain), a PTB domain, and a carboxy terminal region containing PXXP motifs and numerous phosphorylation sites (Carpino et al., 1997 *Cell,* 88: 197; Yamanshi et al., 1997, *Cell,* 88:205).

The invention encompasses characterizing the anti-FcγRIIB antibodies of the invention in modulating one or more IgE mediated responses. Preferably, cells lines co-expressing the high affinity receptor for IgE and the low affinity receptor for FcγRIIB will be used in characterizing the anti-FcγRIIB antibodies of the invention in modulating IgE mediated responses. In a specific embodiment, cells from a rat basophilic leukemia cell line (RBL-H23; Barsumian E. L. et al. 1981 *Eur. J. Immunol.* 11:317, which is incorporated herein by reference in its entirety) transfected with full length human FcγRIIB will be used in the methods of the invention. RBL-2H3 is a well characterized rat cell line that has been used extensively to study the signaling mechanisms following IgE-mediated cell activation. When expressed in RBL-2H3 cells and coaggregated with FcεRI, FcγRIIB inhibits FcεRI-induced calcium mobilization, degranulation, and cytokine production (Malbec et al., 1998, *J. Immunol.* 160:1647; Daeron et al., 1995 *J. Clin. Invest* 95:577; Ott et al., 2002 *J. of Immunol.* 168:4430-4439).

In some embodiments, the invention encompasses characterizing the anti-FcγRIIB antibodies of the invention for inhibition of FcεRI induced mast cell activation. For example, cells from a rat basophilic leukemia cell line (RBL-H23; Barsumian E. L. et al. 1981 *Eur. J. Immunol.* 11:317) that have been transfected with FcγRIIB are sensitized with IgE and stimulated either with F(ab')$_2$ fragments of rabbit anti-mouse IgG, to aggregate FcεRI alone, or with whole rabbit anti-mouse IgG to coaggregate FcγRIIB and FcεRI. In this system, indirect modulation of down stream signaling molecules can be assayed upon addition of antibodies of the invention to the sensitized and stimulated cells. For example, tyrosine phosphorylation of FcγRIIB and recruitment and phosphorylation of SHIP, activation of MAP kinase family members, including but not limited to Erk1, Erk2, JNK, or p38; and tyrosine phosphorylation of $p62^{dok}$ and its association with SHIP and RasGAP can be assayed.

One exemplary assay for determining the inhibition of FcεRI induced mast cell activation by the antibodies of the invention can comprise of the following: transfecting RBL-H23 cells with human FcγRIIB; sensitizing the RBL-H23 cells with IgE; stimulating RBL-H23 cells with either F(ab')$_2$ of rabbit anti-mouse IgG (to aggregate FcεRI alone and elicit FcεRI-mediated signaling, as a control), or stimulating RBL-H23 cells with whole rabbit anti-mouse IgG to (to coaggregate FcγRIIB and FcεRI, resulting in inhibition of FcεRI-mediated signaling). Cells that have been stimulated with whole rabbit anti-mouse IgG antibodies can be further pre-incubated with the antibodies of the invention. Measuring FcεRI-dependent activity of cells that have been pre-incubated with the antibodies of the invention and cells that have not been pre-incubated with the antibodies of the invention, and comparing levels of FcεRI-dependent activity in these cells, would indicate a modulation of FcεRI-dependent activity by the antibodies of the invention.

The exemplary assay described above can be for example, used to identify antibodies that block ligand (IgG) binding to FcγRIIB receptor and antagonize FcγRIIB-mediated inhibition of FcεRI signaling by preventing coaggregating of FcγRIIB and FcεRI. This assay likewise identifies antibodies that enhance coaggregation of FcγRIIB and FcεRI and agonize FcγRIIB-mediated inhibition of FcεRI signaling by promoting coaggregating of FcγRIIB and FcεRI.

In a preferred embodiment, FcεRI-dependent activity is at least one or more of the following: modulation of downstream signaling molecules (e.g., modulation of phosphorylation state of FcγRIIB, modulation of SHIP recruitment, modulation of MAP Kinase activity, modulation of phosphorylation state of SHIP, modulation of SHIP and Shc association SHIP and Shc, modulation of the phosphorylation state of p62$^{dok}$, modulation of p62$^{dok}$ and SHIP association, modulation of p62$^{dok}$ and RasGAP association, modulation of calcium mobilization, modulation of degranulation, and modulation of cytokine production. In yet another preferred embodiment, FcεRI-dependent activity is serotonin release and/or extracellular Ca$^{++}$ influx and/or IgE dependent mast cell activation. It is known to one skilled in the art that coaggregation of FcγRIIB and FcεRI stimulates FcγRIIB tyrosine phosphorylation, stimulates recruitment of SHIP, stimulates SHIP tyrosine phosphorylation and association with Shc, and inhibits activation of MAP kinase family members including, but not limited to, Erk1, Erk2, JNK, p38. It is also known to those skilled in the art that coaggregation of FcγRIIB and FcεRI stimulates enhanced tyrosine phosphorylation of p62$^{dok}$ and its association with SHIP and RasGAP.

In some embodiments, the anti-FcγRIIB antibodies of the invention are characterized for their ability to modulate an IgE mediated response by monitoring and/or measuring degranulation of mast cells or basophils, preferably in a cell-based assay. Preferably, mast cells or basophils for use in such assays have been engineered to contain human FcγRIIB using standard recombinant methods known to one skilled in the art. In a specific embodiment the anti-FcγRIIB antibodies of the invention are characterized for their ability to modulate an IgE mediated response in a cell-based β-hexosaminidase (enzyme contained in the granules) release assay. β-hexosaminidase release from mast cells and basophils is a primary event in acute allergic and inflammatory condition (Aketani et al., 2001 *Immunol. Lett.* 75: 185-9; Aketani et al., 2000 *Anal. Chem.* 72: 2653-8). Release of other inflammatory mediators including but not limited to serotonin and histamine may be assayed to measure an IgE mediated response in accordance with the methods of the invention. Although not intending to be bound by a particular mechanism of action, release of granules such as those containing β-hexosaminidase from mast cells and basophils is an intracellular calcium concentration dependent process that is initiated by the cross-linking of FcεRIs with multivalent antigen.

One exemplary assay for characterizing the anti-FcγRIIB antibodies of the invention in mediating an IgE mediated response is a β-hexosaminidase release assay comprising the following: transfecting RBL-H23 cells with human FcγRIIB; sensitizing the cells with mouse IgE alone or with mouse IgE and an anti-FcεRIIB antibody of the invention; stimulating the cells with various concentrations of goat anti-mouse F(ab)$_2$, preferably in a range from 0.03 µg/mL to 30 µg/mL for about 1 hour; collecting the supernatant; lysing the cells; and measuring the β-hexosaminidase activity released in the supernatant by a colorometric assay, e.g., using p-nitrophenyl N-acetyl-β-D-glucosaminide. The released β-hexosaminidase activity is expressed as a percentage of the released activity to the total activity. The released β-hexosaminidase activity will be measured and compared in cells treated with antigen alone; IgE alone; IgE and an anti-FcγRIIB antibody of the invention. Although not intending to be bound by a particular mechanism of action, once cells are sensitized with mouse IgE alone and challenged with F(ab)$_2$ fragments of a polyclonal goat anti-mouse IgG, aggregation and cross linking of FcγRI occurs since the polyclonal antibody recognizes the light chain of the murine IgE bound to the FcεRI; which in turn leads to mast cell activation and degranulation. On the other hand, when cells are sensitized with mouse IgE and an anti-FcγRIIB antibody of the invention and challenged with F(ab)$_2$ fragments of a polyclonal goat anti-mouse IgG; cross linking of FcεRI and FcγRIIB occurs, resulting in inhibition of FcεRI induced degranulation. In either case, goat anti mouse F(ab)$_2$ induces a dose-dependent β-hexoaminidase release. In some embodiments, the anti-FcγRIIB antibodies bound to the FcγRIIB receptor and cross linked to FcεRI do not affect the activation of the inhibitory pathway, i.e., there is no alteration in the level of degranulation in the presence of an anti-FcγRIIB antibody. In other embodiments, the anti-FcγRIIB antibodies mediate a stronger activation of the inhibitory receptor, FcγRIIB, when bound by the anti-FcγRIIB antibody, allowing effective cross linking to FcεRI and activation of the inhibitory pathway of homo-aggregated FcγRIIB.

The invention also encompasses characterizing the effect of the anti-FcγRIIB antibodies of the invention on IgE mediated cell response using calcium mobilization assays using methodologies known to one skilled in the art. An exemplary calcium mobilization assay may comprise the following: priming basophils or mast cells with IgE; incubating the cells with a calcium indicator, e.g., Fura 2; stimulating cells as described supra; and monitoring and/or quantitating intracellular calcium concentration for example by using flow cytometry. The invention encompasses monitoring and/or quantitating intracellular calcium concentration by any method known to one skilled in the art see, e.g., *Immunology Letters*, 2001, 75:185-9; *British J. of Pharm*, 2002, 136:837-45; *J. of Immunology*, 168:4430-9 and *J. of Cell Biol.*, 153(2):339-49; all of which are incorporated herein by reference.

In preferred embodiments, anti-FcγRIIB antibodies of the invention inhibit IgE mediated cell activation. In other embodiments, the anti-FcγRIIB antibodies of the invention block the inhibitory pathways regulated by FcγRIIB or block the ligand binding site on FcγRIIB and thus enhance immune response.

The ability to study human mast cells has been limited by the absence of suitable long term human mast cell cultures. Recently two novel stem cell factor dependent human mast cell lines, designated LAD 1 and LAD2, were established from bone marrow aspirates from a patient with mast cell sarcoma/leukemia (Kirshenbaum et al., 2003, *Leukemia research*, 27:677-82, which is incorporated herein by reference in its entirety.). Both cell lines have been described to express FcεRI and several human mast cell markers. The invention encompasses using LAD 1 and 2 cells in the methods of the invention for assessing the effect of the antibodies of the invention on IgE mediated responses. In a specific embodiment, cell-based β-hexosaminidase release assays such as those described supra may be used in LAD cells to determine any modulation of the IgE-mediated response by the anti-FcγRIIB antibodies of the invention. In an exemplary assay, human mast cells, e.g., LAD 1, are primed with chimaeric human IgE anti-nitrophenol (NP) and challenged with BSA-NP, the polyvalent antigen, and cell degranulation is monitored by measuring the β-hexosaminidase released in the supernatant (Kirshenbaum et al., 2003, *Leukemia research*, 27:677-682, which is incorporated herein by reference in its entirety).

In some embodiments, if human mast cells have a low expression of endogenous FcγRIIB, as determined using standard methods known in the art, e.g., FACS staining, it may be difficult to monitor and/or detect differences in the activation of the inhibitory pathway mediated by the anti-FcγRIIB antibodies of the invention. The invention thus encompasses alternative methods, whereby the FcγRIIB expression may be upregulated using cytokines and particular growth conditions. FcγRIIB has been described to be highly up-regulated in human monocyte cell lines, e.g., THP1 and U937, (Tridandapani et al., 2002, *J. Biol. Chem.*, 277(7): 5082-5089) and in primary human monocytes (Pricop et al., 2001, *J. of Immunol.*, 166: 531-537) by IL4. Differentiation of U937 cells with dibutyryl cyclic AMP has been described to increase expression of FcγRII (Cameron et al., 2002 *Immunology Letters* 83, 171-179). Thus the endogenous FcγRIIB expression in human mast cells for use in the methods of the invention may be up-regulated using cytokines, e.g., IL-4, IL-13, in order to enhance sensitivity of detection.

The invention also encompasses characterizing the anti-FcγRIIB antibodies of the invention for inhibition of B-cell receptor (BCR)-mediated signaling. BCR-mediated signaling can include at least one or more down stream biological responses, such as activation and proliferation of B cells, antibody production, etc. Coaggregation of FcγRIIB and BCR leads to inhibition of cell cycle progression and cellular survival. Further, coaggregation of FcγRIIB and BCR leads to inhibition of BCR-mediated signaling.

Specifically, BCR-mediated signaling comprises at least one or more of the following: modulation of down stream signaling molecules (e.g., phosphorylation state of FcγRIIB, SHIP recruitment, localization of Btk and/or PLCγ, MAP kinase activity, recruitment of Akt (anti-apoptotic signal), calcium mobilization, cell cycle progression, and cell proliferation.

Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, Ins(1,4,5)$P_3$ production, and Erk and Akt phosphorylation (Brauweiler A. et al., 2001, *Journal of Immunology*, 167(1): 204-211). Accordingly, ex vivo B cells from SHIP deficient mice can be used to characterize the antibodies of the invention. One exemplary assay for determining FcγRIIB-mediated inhibition of BCR signaling by the antibodies of the invention can comprise the following: isolating splenic B cells from SHIP deficient mice, activating said cells with lipopolysachharide, and stimulating said cells with either F(ab')2 anti-IgM to aggregate BCR or with anti-IgM to coaagregate BCR with FcγRIIB. Cells that have been stimulated with intact anti-IgM to coaggregate BCR with FcγRIIB can be further pre-incubated with the antibodies of the invention. FcγRIIB-dependent activity of cells can be measured by standard techniques known in the art. Comparing the level of FcγRIIB-dependent activity in cells that have been pre-incubated with the antibodies of the invention and cells that have not been pre-incubated, and comparing the levels would indicate a modulation of FcγRIIB-dependent activity by the antibodies of the invention.

Measuring FcγRIIB-dependent activity can include, for example, measuring intracellular calcium mobilization by flow cytometry, measuring phosphorylation of Akt and/or Erk, measuring BCR-mediated accumulation of PI(3,4,5)$P_3$, or measuring FcγRIIB-mediated proliferation B cells.

The assays can be used, for example, to identify antibodies that modulate FcγRIIB-mediated inhibition of BCR signaling by blocking the ligand (IgG) binding site to FcγRIIB receptor and antagonizing FcγRIIB-mediated inhibition of BCR signaling by preventing coaggregation of FcγRIIB and BCR. The assays can also be used to identify antibodies that enhance coaggregation of FcγRIIB and BCR and agonize FcγRIIB-mediated inhibition of BCR signaling.

The invention relates to characterizing the anti-FcγRIIB antibodies of the invention for FcγRII-mediated signaling in human monocytes/macrophages. Coaggregation of FcγRIIB with a receptor bearing the immunoreceptor tyrosine-based activation motif (ITAM) acts to down-regulate FcγR-mediated phagocytosis using SHIP as its effector (Tridandapani et al. 2002, *J. Biol. Chem.* 277(7):5082-9). Coaggregation of FcγRIIA with FcγRIIB results in rapid phosphorylation of the tyrosine residue on FcγRIIB's ITIM motif, leading to an enhancement in phosphorylation of SHIP, association of SHIP with Shc, and phosphorylation of proteins having the molecular weight of 120 and 60-65 kDa. In addition, coaggregation of FcγRIIA with FcγRIIB results in down-regulation of phosphorylation of Akt, which is a serine-threonine kinase that is involved in cellular regulation and serves to suppress apoptosis.

The invention further encompasses characterizing the anti-FcγRIIB antibodies of the invention for their inhibition of FcγR-mediated phagocytosis in human monocytes/macrophages. For example, cells from a human monocytic cell line, THP-1 can be stimulated either with Fab fragments of mouse monoclonal antibody IV.3 against FcγRII and goat anti-mouse antibody (to aggregate FcγRIIA alone), or with whole TV.3 mouse monoclonal antibody and goat anti-mouse antibody (to coaggregate FcγRIIA and FcγRIIB). In this system, modulation of down stream signaling molecules, such as tyrosine phosphorylation of FcγRIIB, phosphorylation of SHIP, association of SHIP with Shc, phosphorylation of Akt, and phosphorylation of proteins having the molecular weight of 120 and 60-65 kDa can be assayed upon addition of antibodies of the invention to the stimulated cells. In addition, FcγRIIB-dependent phagocytic efficiency of the monocyte cell line can be directly measured in the presence and absence of the antibodies of the invention.

Another exemplary assay for determining inhibition of FcγR-mediated phagocytosis in human monocytes/macrophages by the antibodies of the invention can comprise the following: stimulating THP-1 cells with either Fab of IV.3 mouse anti-FcγRII antibody and goat anti-mouse antibody (to aggregate FcγRIIA alone and elicit FcγRIIA-mediated signaling); or with mouse anti-FcγRII antibody and goat anti-mouse antibody (to coaggregate FcγRIIA and FcγRIIB and inhibiting FcγRIIA-mediated signaling. Cells that have been stimulated with mouse anti-FcγRII antibody and goat anti-mouse antibody can be further pre-incubated with the antibodies of the invention. Measuring FcγRIIA-dependent activity of stimulated cells that have been pre-incubated with antibodies of the invention and cells that have not been pre-incubated with the antibodies of the invention and comparing levels of FcγRIIA-dependent activity in these cells would indicate a modulation of FcγRIIA-dependent activity by the antibodies of the invention.

The exemplary assay described can be used for example, to identify antibodies that block ligand binding of FcγRIIB receptor and antagonize FcγRIIB-mediated inhibition of FcγRIIA signaling by preventing coaggregation of FcγRIIB and FcγRIIA. This assay likewise identifies antibodies that enhance coaggregation of FcγRIIB and FcγRIIA and agonize FcγRIIB-mediated inhibition of FcγRIIA signaling.

In another embodiment of the invention, the invention relates to characterizing the function of the antibodies of the invention by measuring the ability of THP-1 cells to phagocytose fluoresceinated IgG-opsonized sheep red blood cells (SRBC) by methods previously described (Tridandapani et al., 2000, *J. Biol. Chem.* 275: 20480-7). For example, an exemplary assay for measuring phagocytosis comprises of: treating THP-1 cells with the antibodies of the invention or with a control antibody that does not bind to FCγRII, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate a modulation of FcγRIIA-dependent activity by the antibodies of the invention. This assay can be used to identify, for example, antibodies that block ligand binding of FcγRIIB receptor and antagonize FcγRIIB-mediated inhibition of phagocytosis. This assay can also identify antibodies that enhance FcγRIIB-mediated inhibition of FcγRIIA signaling.

In a preferred embodiment, the antibodies of the invention modulate FcγRIIB-dependent activity in human monocytes/macrophages in at least one or more of the following ways: modulation of downstream signaling molecules (e.g., modulation of phosphorylation state of FcγRIIB, modulation of SHIP phosphorylation, modulation of SHIP and Shc association, modulation of phosphorylation of Akt, modulation of phosphorylation of additional proteins around 120 and 60-65 kDa) and modulation of phagocytosis.

The invention encompasses characterization of the antibodies of the invention using assays known to those skilled in the art for identifying the effect of the antibodies on effector cell function of therapeutic antibodies, e.g., their ability to enhance tumor-specific ADCC activity of therapeutic antibodies. Therapeutic antibodies that may be used in accordance with the methods of the invention include but are not limited to anti-tumor antibodies, anti-viral antibodies, anti-microbial antibodies (e.g., bacterial and unicellular parasites), examples of which are disclosed herein (Section 5.4.6). In particular, the invention encompasses characterizing the antibodies of the invention for their effect on FcγR-mediated effector cell function of therapeutic antibodies, e.g., tumor-specific monoclonal antibodies. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al., 2000, *Methods Mol. Biol.* 121: 179-92; Baggiolini et al., 1998 *Experientia*, 44(10): 841-8; Lehmann et al., 2000 *J. Immunol. Methods*, 243(1-2): 229-42; Brown E J. 1994, *Methods Cell Biol.*, 45: 147-64; Munn et al., 1990 *J. Exp. Med.*, 172: 231-237, Abdul-Majid et al., 2002 *Scand. J. Immunol.* 55: 70-81; Ding et al., 1998, *Immunity* 8:403-411, each of which is incorporated by reference herein in its entirety).

Antibodies of the invention can be assayed for their effect on FcγR-mediated ADCC activity of therapeutic antibodies in effector cells, e.g., natural killer cells, using any of the standard methods known to those skilled in the art (See e.g., Perussia et al., 2000, *Methods Mol. Biol.* 121: 179-92). "Antibody-dependent cell-mediated cytotoxicity" and "ADCC" as used herein carry their ordinary and customary meaning in the art and refer to an in vitro cell-mediated reaction in which nonspecific cytotoxic cells that express FcγRs (e.g., monocytic cells such as Natural Killer (NK) cells and macrophages) recognize bound antibody on a target cell and subsequently cause lysis of the target cell. In principle, any effector cell with an activating FcγR can be triggered to mediate ADCC. The primary cells for mediating ADCC are NK cells which express only FcγRIII, whereas monocytes, depending on their state of activation, localization, or differentiation, can express FcγRI, FcγRII, and FcγRIII. For a review of FcγR expression on hematopoietic cells see, e.g., Ravetch et al., 1991, *Annu. Rev. Immunol.*, 9:457-92, which is incorporated herein by reference in its entirety.

Effector cells are leukocytes which express one or more FcγRs and perform effector functions. Preferably, the cells express at least FcγRIII and perform ADCC effector function. Effector cells that may be used in the methods of the invention include but are not limited to peripheral blood mononuclear cells (PBMC), natural killer (NK) cells, monocytes, and neutrophils; with PBMCs and NK cells being preferred. The effector cells may be isolated from a native source thereof, e.g., from blood or PBMCs as described herein. Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. For example, PBMCs may be isolated by layering whole blood onto Ficoll-Hypaque and spinning the cells at 500 g, at room temperature for 30 minutes. The leukocyte layer can be harvested as effector cells. Other effector cells that may be used in the ADCC assays of the invention include but are not limited to monocyte-derived macrophages (MDMs). MDMs that are used as effector cells in the methods of the invention, are preferably obtained as frozen stocks or used fresh, (e.g., from Advanced Biotechnologies, MD). In most preferred embodiments, elutriated human monocytes are used as effector cells in the methods of the invention. Elutriated human monocytes express activating receptors, FcγRIIIA and FcγRIIA and the inhibitory receptor, FcγRIIB. Human monocytes are commercially available and may be obtained as frozen stocks, thawed in basal medium containing 10% human AB serum or in basal medium with human serum containing cytokines. Levels of expression of FcγRs in the cells may be directly determined; e.g. using FACS analysis. Alternatively, cells may also be allowed to mature to macrophages in culture. The level of FcγRIIB expression may be increased in macrophages. Antibodies that may be used in determining the expression level of FcγRs include but are not limited to anti-human FcγRIIA antibodies, e.g., IV.3-FITC; anti-FcγRI antibodies, e.g., 32.2 FITC; and anti-FcγRIIIA antibodies, e.g., 3G8-PE.

Target cells used in the ADCC assays of the invention include, but are not limited to, breast cancer cell lines, e.g., SK-BR-3 with ATCC accession number HTB-30 (see, e.g., Tremp et al., 1976, *Cancer Res.* 33-41); B-lymphocytes; cells derived from Burkitts lymphoma, e.g., Raji cells with ATCC accession number CCL-86 (see, e.g., Epstein et al., 1965, *J. Natl. Cancer Inst.* 34: 231-240), Daudi cells with ATCC accession number CCL-213 (see, e.g., Klein et al., 1968, *Cancer Res.* 28: 1300-10); ovarian carcinoma cell lines, e.g., OVCAR-3 with ATCC accession number HTB-161 (see, e.g., Hamilton, Young et al., 1983), SK-OV-3, PA-1, CAOV3, OV-90, and IGROV-1 (available from the NCI repository Benard et al., 1985, *Cancer Research,* 45:4970-9; which is incorporated herein by reference in its entirety. The target cells must be recognized by the antigen binding site of the antibody to be assayed. The target cells for use in the methods of the invention may have low, medium, or high expression level of a cancer antigen. The expression levels of the cancer antigen may be determined using common methods known to one skilled in the art, e.g., FACS analysis. For example, the invention encompasses the use of ovarian cancer cells such as IGROV-1, wherein Her2/neu is expressed at different levels, or OV-CAR-3 (ATCC Assession Number HTB-161; characterized by a lower expression of Her2/neu than SK-BR-3, the breast carcinoma cell line). Other ovarian carcinoma cell lines that may be used as target cells in the methods of the invention include OVCAR-8 (Hamilton et al., 1983, *Cancer Res.* 43:5379-89, which is incorporated herein by reference in its entirety); SK-OV-3 (ATCC Accession Number HTB-77); Caov-3 (ATCC Accession Number HTB-75); PA-1 (ATCC Accession Number CRL-1572); OV-90 (ATCC Accession Number CRL-11732); and OVCAR-4. Other breast cancer cell lines that may be used in the methods of the invention include BT-549 (ATCC Accession Number HTB-122), MCF$_7$ (ATCC Accession Number HTB-22), and Hs578T (ATCC Accession Number HTB-126), all of which are available from the NCl repository and ATCC and incorporated herein by reference. Other cell lines that may be used in the methods of the invention include but are not limited to CCRF-CEM (leukemia); HL-60 (TB, leukemia); MOLT-4 (leukemia); RPMI-8226 (leukemia); SR (leukemia); A549 (Non-small cell lung); EKVX (Non-small cell lung); HOP-62 (Non-small cell lung); HOP-92 (Non-small cell lung); NCl-H226 (Non-small cell lung); NCl-H23 (Non-small cell lung); NCl-H322M (Non-small cell lung); NCl-H460 (Non-small cell lung); NCl-H522 (Non-small cell lung); COLO 205 (Colon); HCC-2998 (Colon); HCT-116 (Colon); HCT-15 (Colon); HT29 (Colon); KM12 (Colon); SW-620 (Colon); SF-268 (CNS); SF-295 (CNS); SF-539 (CNS); SNB-19 (CNS); SNB-75 (CNS); U251 (CNS); LOX 1MV1 (Melanoma); MALME-3M (Melanoma); M14 (Melanoma); SK-MEL-2 (Melanoma); SK-MEL-28 (Melanoma); SK-MEL-5 (Melanoma); UACC-257 (Melanoma); UACC-62 (Melanoma); IGR-OVI (Ovarian); OVCAR-3,4,5,8 (Ovarian); SK-OV-3 (Ovarian); 786-0 (Renal); A498 (Renal); ACHN (Renal); CAKl-1 (Renal); SN12C(Renal); TK-10 (Renal); UO-31 (Renal); PC-3C (Prostate); DU-145 (Prostate); NCl/ADR-RES (Breast); MDA-MB-231/ATCC (Breast); MA-MB-435 (Breast); DMS114 (Small-cell lung); and SHP-77 (Small-cell lung); all of which are available from the NCl and incorporated herein by reference.

An exemplary assay for determining the effect of the antibodies of the invention on the ADCC activity of therapeutic antibodies is based on a $^{51}$Cr release assay comprising of: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell lysis); preferably, the target cells express one or more tumor antigens, osponizing the target cells with one or more antibodies that immunospecifically bind the tumor antigens expressed on the cell surface of the target cells, in the presence and absence of an antibody of the invention, e.g., 2B6, 3H7, combining the opsonized radiolabeled target cells with effector cells in a microtitre plate at an appropriate ratio of target cells to effector cells; incubating the mixture of cells preferably for 16-18 hours, preferably at 37° C.; collecting supernatants; and analyzing the radioactivity in the supernatant samples. The cytotoxicity of the therapeutic antibodies in the presence and absence of the antibodies of the invention can then be determined, for example using the following formula: Percent specific lysis=(Experimental lysis-antibody-independent lysis/maximal lysis−antibody independent lysis)×100%. A graph can be generated by varying either the target: effector cell ratio or antibody concentration.

In yet another embodiment, the antibodies of the invention are characterized for antibody dependent cellular cytotoxicity (ADCC) in accordance with the method described earlier, see, e.g., Ding et al., *Immunity,* 1998, 8:403-11; which is incorporated herein by reference in its entirety.

In some embodiments, the invention encompasses characterizing the function of the antibodies of the invention in enhancing ADCC activity of therapeutic antibodies in an in vitro based assay and/or in an animal model.

In a specific embodiment, the invention encompasses determining the function of the antibodies of the invention in enhancing tumor specific ADCC using an ovarian cancer model and/or breast cancer model.

Preferably, the ADCC assays of the invention are done using more than one cancer cell line, characterized by the expression of at least one cancer antigen, wherein the expression level of the cancer antigen is varied among the cancer cell lines used. Although not intending to be bound by a particular mechanism of action, performing ADCC assays in more than one cell line wherein the expression level of the cancer antigen is varied, will allow determination of stringency of tumor clearance of the antibodies of the invention. In one embodiment, the ADCC assays of the invention are done using cancer cell lines with different levels of expression of a cancer antigen.

In an exemplary assay, OVCAR3, an ovarian carcinoma cell line can serve as the tumor target expressing the tumor antigens, Her2/neu and TAG-72; human monocytes, that express the activating FcγRIIIA and FcγRIIA and inhibitory FcγRIIB, can be used as effectors; and tumor specific murine antibodies, ch4D5 and chCC49, can be used as the tumor specific antibodies. OVCAR-3 cells are available from ATCC (Accession Number HTB-161). Preferably, OVCAR-3 cells are propagated in medium supplemented with 0.01 mg/ml bovine insulin. 5×10$^6$ viable OVCAR-3 cells may be injected subcutaneously (s.c) into age and weight matched nude athymic mice with Matrigel (Becton Dickinson). The estimated weight of the tumor can be calculated by the formula: length-(width)$^2$/2, and preferably does not exceed 3 grams. Anchorage-dependent tumor can be isolated after 6-8 weeks, and the cells can be dissociated by adding 1 μg of Collagenase (Sigma) per gram of tumor and a 5 mg/mL RNase, passed through a cell strainer and nylon mesh to isolate cells. Cells can then be frozen for long-term storage for s.c. injection for establishment of the xenograft model.

Hybridomas secreting CC49 and 4D5 antibodies are available with ATCC Accession Numbers HB-9459 and CRL-3D463 and the heavy chain and light chain nucleotide sequences are in the public domain Murray et al., 1994 *Cancer* 73 (35):1057-66, Yamamoto et al., 1986 *Nature,* 319:230-

4; both of which are incorporated herein by reference in their entirety. Preferably, the 4D5 and CC49 antibodies are chimerized using standard methods known to one skilled in the art so that the human Fc sequence, e.g., human constant region of IgG1, is grafted onto the variable region of the murine antibodies in order to provide the effector function. The chimeric 4D5 and CC49 antibodies bind via their variable region to the target cell lines and via their Fc region to FcγRs expressed on human effector cells. CC49 is directed to TAG-72; a high molecular weight mucin that is highly expressed on many adenocarcinoma cells and ovarian carcinoma (Lottich et al., 1985 *Breast Cancer Res. Treat.* 6(1):49-56; Mansi et al., 1989 *Int. J. Rad. Appl. Instrum B.* 16(2):127-35; Colcher et al., 1991 *Int. J. Rad. Appl. Instrum B.* 18:395-41; all of which are incorporated herein by reference in their entirety). 4D5 is directed to human epidermal growth factor receptor 2 (Carter et al., 1992, *Proc. Nat. Acad. Sci. USA,* 89: 4285-9 which is incorporated herein by reference). Antibodies of the invention can then be utilized to investigate the enhancement of ADCC activity of the tumor specific antibodies, by blocking the inhibitory FcγRIIB. Although not intending to be bound by a particular mechanism of action, upon activation of effector cells that express at least one activating FcγR, e.g., FcγRIIA, the expression of the inhibitory receptor (FcγRIIB) is enhanced and this limits the clearance of tumors as the ADCC activity of FcγRIIA is suppressed. However, antibodies of the invention can serve as a blocking antibody, i.e., an antibody that will prevent the inhibitory signal from being activated and thus the activation signal, e.g., ADCC activity, will be sustained for a longer period and may result in potent tumor clearance.

Preferably, the antibodies of the invention for use in enhancement of ADCC activity have been modified to comprise at least one amino acid modification, so that their binding to FcγR has been diminished, most preferably abolished. In some embodiments, the antibodies of the invention have been modified to comprise at least one amino acid modification which reduces the binding of the constant domain to an activating FcγR, e.g., FcγRIIIA, FcγRIIA, as compared to a wild type antibody of the invention while retaining maximal FcγRIIB blocking activity. Antibodies of the invention may be modified in accordance with any method known to one skilled in the art or disclosed herein. Any amino acid modification which is known to disrupt effector function may be used in accordance with the methods of the invention such as those disclosed in U.S. Application Ser. Nos. 60/439,498 (filed Jan. 9, 2003); and 60/456,041 (filed Mar. 19, 2003); both of which are incorporated herein by reference in their entireties. In some embodiments, antibodies of the invention are modified so that position 265 is modified, e.g., position 265 is substituted with alanine. In preferred embodiments, the murine constant region of an antibody of the invention is swapped with the corresponding human constant region comprising a substitution of the amino acid at position 265 with alanine, so that the effector function is abolished while FcγRIIB blocking activity is maintained. A single amino acid change at position 265 of IgG1 heavy chain has been shown to significantly reduce binding to FcγR based on ELISA assays, Sheilds et al., 2001, *J. Biol. Chem.,* 276(9):6591-604; which is incorporated herein by reference in its entirety and has resulted in tumor mass reduction. In other embodiments, antibodies of the invention are modified so that position 297 is modified, e.g., position 297 is substituted with glutamine, so that the N-linked glycosylation site is eliminated (see, e.g., Jefferies et al., 1995, *Immunol. lett* 44:111-7; Lund et al., 1996, *J. Immunol,* 157:4963-69; Wright et al., 1994, *J. Exp. Med.* 180:1087-96; White et al., 1997; *J. Immunol.* 158:426-35; all of which are incorporated herein by reference in their entireties. Modification at this site has been reported to abolish all interaction with FcγRs. In preferred embodiments, the murine constant region of an antibody of the invention is swapped with the corresponding human constant region comprising a substitution of the amino acid at position 265 and/or 297, so that the effector function is abolished while FcγRIIB blocking activity is maintained.

An exemplary assay for determining the ADCC activity of the tumor specific antibodies in the presence and absence of the antibodies of the invention is a non-radioactive europium based fluorescent assay (BATDA, Perkin Elmer) and may comprise the following: labeling the targets cells with an acteoxylmethyl ester of fluorescence-enhancing ester that forms a hydrophilic ligand (TDA) with the membrane of cells by hydrolysis of the esters; this complex is unable to leave the cell and is released only upon lysis of the cell by the effectors; adding the labeled targets to the effector cells in presence of anti-tumor antibodies and an antibody of the invention; incubating the mixture of the target and effector cells a for 6 to 16 hours, preferably at 37° C. The extent of ADCC activity can be assayed by measuring the amount of ligand that is released and interacts with europium (DELFIA reagent; PerkinElmer). The ligand and the europium form a very stable and highly fluorescent chelate (EuTDA) and the measured fluorescence is directly proportional to the number of cells lysed. Percent specific lysis can be calculated using the formula: (Experimental lysis-antibody-independent lysis/maximal lysis antibody-independent lysis×100%).

In some embodiments, if the sensitivity of the fluorescence-based ADCC assay is too low to detect ADCC activity of the therapeutic antibodies, the invention encompasses radioactive-based ADCC assays, such as $^{51}$Cr release assay. Radioactive-based assays may be done instead of or in combination with fluorescent-based ADCC assays.

An exemplary $^{51}$Cr release assay for characterizing the antibodies of the invention can comprise the following: labeling 1–2×10$^6$ target cells such as OVCAR-3 cells with $^{51}$Cr; opsonizing the target cells with antibodies 4D5 and CC49 in the presence and absence of an antibody of the invention and adding 5×10$^3$ cells to 96 well plate. Preferably 4D5 and CC49 are at a concentration varying from 1-15 μg/mL; adding the opsonized target cells to monocyte-derived macrophages (MDM) (effector cells); preferably at a ratio varying from 10:1 to 100:1; incubating the mixture of cells for 16-18 hours at 37° C.; collecting supernatants; and analyzing the radioactivity in the supernatant. The cytotoxicity of 4D5 and CC49 in the presence and absence of an antibody of the invention can then be determined, for example using the following formula percent specific lysis=(experimental lysis−antibody independent lysis/maximal lysis−antibody independent lysis)×100%.

In some embodiments, the in vivo activity of the FcγRIIB antibodies of the invention is determined in xenograft human tumor models. Tumors may be established using any of the cancer cell lines described supra. In some embodiments, the tumors will be established with two cancer cell lines, wherein the first cancer cell line is characterized by a low expression of a cancer antigen and a second cancer cell line, wherein the second cancer cell line is characterized by a high expression of the same cancer antigen. Tumor clearance may then be determined using methods known to one skilled in the art, using an anti-tumor antibody which immunospecifically binds the cancer antigen on the first and second cancer cell line, and an appropriate mouse model, e.g., a Balb/c nude mouse model (e.g., Jackson Laboratories, Taconic), with adoptively transferred human monocytes and MDMs as effector cells. Any of the antibodies described supra may then be tested in this animal model to evaluate the role of anti-FcγRIIB antibody of the invention in tumor clearance. Mice that may be used in the invention include for example FcγRIII −/− (where FcγRIIIA is knocked out); Fcγ−/− nude mice (where FcγRI and FcγRIITA are knocked out); or human FcγRIIB knock in mice or a transgenic knock-in mice, where mouse fcgr2 and fcgr3 loci on chromosome 1 are inactivated and the mice express human FcγRIIA, human FcγRIIA human FcγRIIB, human FcγRIIC, human FcγRIIIA, and human FcγRIIIB.

An exemplary method for testing the in vivo activity of an antibody of the invention may comprise the following: establishing a xenograft murine model using a cancer cell line characterized by the expression of a cancer antigen and determining the effect of an antibody of the invention on an antibody specific for the cancer antigen expressed in the cancer cell line in mediating tumor clearance. Preferably, the in vivo activity is tested parallel using two cancer cell lines, wherein the first cancer cell line is characterized by a first cancer antigen expressed at low levels and a second cancer cell line, characterized by the same cancer antigen expressed at a higher level relative to the first cancer cell line. These experiments will thus increase the stringency of the evaluation of the role of an antibody of the invention in tumor clearance. For example, tumors may be established with the IGROV-1 cell line and the effect of an anti-FcγRIIB antibody of the invention in tumor clearance of a Her2/neu specific antibody may be assessed. In order to establish the xenograft tumor models, $5 \times 10^6$ viable cells, e.g., IGROV-1, SKBR3, may be injected, e.g., s.c. into mice, e.g., 8 age and weight matched femal nude athymic mice using for example Matrigel (Becton Dickinson). The estimated weight of the tumor may be determined by the formula: length×(width)$^2$/2; and preferably does not exceed 3 grams. Injection of IGROV-1 cells s.c. gives rise to fast growing tumors while the i.p. route induces a peritoneal carcinomatosis which kills mice in 2 months (Benard et al., 1985, *Cancer Res.* 45:4970-9). Since the IGROV-1 cells form tumors within 5 weeks, at day 1 after tumor cell injection, monocytes as effectors are co-injected i.p. along with a therapeutic antibody specific for Her2/neu, e.g., Ch4D5, and an antibody of the invention; e.g. chimeric 2B6 or 3H7 as described supra. Preferably, the antibodies are injected at 4 μg each per gram of mouse body weight (mbw). The initial injection will be followed by weekly injections of antibodies for 4-6 weeks thereafter at 2 μg/wk. Human effector cells will be replenished once in 2 weeks. A group of mice will receive no therapeutic antibody but will be injected with a chimeric 4D5 comprising a N297A mutation and human IgG1 as isotype control antibodies for the anti-tumor and anti-FcγRIIB antibodies, respectively. Mice may be placed in groups of 4 and monitored three times weekly.

Table 3 below is an exemplary setup for tumor clearance studies in accordance with the invention. As shown in Table 3, six groups of 8 mice each will be needed for testing the role of an antibody of the invention in tumor clearance, wherein one target and effector cell combination is used and wherein two different combinations of the antibody concentration are used. In group A, only tumor cells are injected; in group B tumor cells and monocytes are injected; in group C, tumor cells, monocytes, an anti-tumor antibody (ch4D5) are injected; in group D, tumor cells, monocytes, anti-tumor antibody, and an anti-FcγRIIB antibody are injected; in group E, tumor cells, monocytes and an anti-FcγRIIB antibody are injected; in group F, tumor cells, monocytes, Ch4D5 (N297Q), and human IgG1 are injected. It will be appreciated by one skilled in the art that various antibody concentrations of various antibody combinations may be tested in the tumor models described. Preferably, studies using a breast cancer cell line, e.g., SKBR3, is carried out in parallel to the above-described experiment.

TABLE 3

EXEMPLARY EXPERIMENTAL SET UP IN MICE

| 8 mice/ group | Tumor cell s.c day 0 | Monocytes i.p at day 1 | ch4D5 at 4 μg/gm of mbw day 1 i.p | ch4D5 N297Q at 4 μg/gm of mbw day 1 i.p | ch2B6 N297Q at 4 μg/gm of mbw day 1 i.p | Human IgG1 4 μg/gm of mbw day 1 i.p |
|---|---|---|---|---|---|---|
| A | + | − | − | − | − | − |
| B | + | + | − | − | − | − |
| C | + | + | + | − | − | − |
| D | + | + | + | − | + | − |
| E | + | + | − | − | + | − |
| F | + | + | − | + | − | + |

The endpoint of the xenograft tumor models is determined based on the size of the tumors, weight of mice, survival time and histochemical and histopathological examination of the cancer, using methods known to one skilled in the art. Each of the groups of mice in Table 3 will be evaluated. Mice are preferably monitored three times a week. Criteria for tumor growth may be abdominal distention, presence of palpable mass in the peritoneal cavity. Preferably estimates of tumor weight versus days after inoculation will be calculated. A comparison of the aforementioned criteria of mice in Group D compared to those in other groups will define the role of an antibody of the invention in enhancement of tumor clearance. Preferably, antibody-treated animals will be under observation for an additional 2 months after the control group.

In alternative embodiments, human FcγRIIB "knock in" mice expressing human FcγRIIB on murine effector cells may be used in establishing the in vivo activity of the antibodies of the invention, rather than adoptively transferring effector cells. Founder mice expressing the human FcγRIIB may be generated by "knocking in" the human FcγRIIB onto the mouse FcγRIIB locus. The founders can then be back-crossed onto the nude background and will express the human FcγRIIB receptor. The resulting murine effector cells will express endogenous activating FcγRI and FcγRIIIA and inhibitory human FcγRIIB receptors.

The in vivo activity of the antibodies of the invention may be further tested in a xenograft murine model with human primary tumor derived cells, such as human primary ovarian and breast carcinoma derived cells. Ascites and pleural effusion samples from cancer patients may be tested for expression of Her2/neu, using methods known to one skilled in the art. Samples from ovarian carcinoma patients may be processed by spinning down the ascites at 6370 g for 20 minutes at 4° C., lysing the red blood cells, and washing the cells with PBS. Once the expression of Her2/neu in tumor cells is determined, two samples, a median and a high expresser may be selected for s.c. inoculation to establish the xenograft tumor model. The isolated tumor cells will then be injected i.p. into mice to expand the cells. Approximately 10 mice may be injected i.p. and each mouse ascites further passaged into two mice to obtain ascites from a total of 20 mice which can be used to inject a group of 80 mice. Pleural effusion samples may be processed using a similar method as ascites. The Her2/neu+ tumor cells from pleural effusion samples may be injected into the upper right & left mammary pads of the mice.

In some embodiments, if the percentage of neoplastic cells in the ascites or pleural effusion samples is low compared to other cellular subsets, the neoplastic cells may be expanded in vitro. In other embodiments, tumor cells may be purified using CC49 antibody (anti-TAG-72)-coated magnetic beads as described previously, see, e.g., Barker et al., 2001, *Gynecol. Oncol.* 82:57, 63, which is incorporated herein by reference in its entirety. Briefly, magnetic beads coated with CC49 antibody can be used to separate the ovarian tumor cells that will be detached from the beads by an overnight incubation at 37° C. In some embodiments, if the tumor cells lack the TAG-72 antigen, negative depletion using a cocktail of antibodies, such as those provided by Stem Cell Technologies, Inc., Canada, may be used to enrich the tumor cells.

In other embodiments, other tumors markers besides Her2/neu may be used to separate tumor cells obtained from the ascites and pleural effusion samples from non-tumor cells. In the case of pleural effusion or breast tissue, it has been recently reported that CD44 (an adhesion molecule), B38.1(a breast/ovarian cancer-specific marker), CD24 (an adhesion molecule) may be used as markers, see, e.g., Al Hajj, et al., 2003, *Proc. Natl. Acad. Sci. USA* 100:3983, 8; which is incorporated herein by reference in its entirety. Once tumor cells are purified they may be injected s.c. into mice for expansion.

Preferably, immunohistochemistry and histochemistry is performed on ascites and pleural effusion of patients to analyze structural characteristics of the neoplasia. Such methods are known to one skilled in the art and encompassed within the invention. The markers that may be monitored include for example cytokeratin (to identify ovarian neoplastic and mesothelial cells from inflammatory and mesenchymal cells); calretinin (to separate mesothelial from Her2neu positive neoplastic cells); and CD45 (to separate inflammatory cells from the rest of the cell population in the samples). Additional markers that may be followed include CD3 (T cells), CD20 (B cells), CD56 (NK cells), and CD14 (monocytes). It will be appreciated by one skilled in the art that the immunohistochemistry and histochemistry methods described supra, are analogously applied to any tumor cell for use in the methods of the invention. After s.c. inoculation of tumor cells, mice are followed for clinical and anatomical changes. As needed, mice may be necropsied to correlate total tumor burden with specific organ localization.

In a specific embodiment, tumors are established using carcinoma cell lines such as IGROV-1, OVCAR-8, SK-B, and OVCAR-3 cells and human ovarian carcinoma ascites and pleural effusion from breast cancer patients. The ascites preferably contain both the effectors and the tumor targets for the antibodies being tested. Human monocytes will be transferred as effectors.

5.2.1 Polynucleotides Encoding an Antibody

The present invention also includes polynucleotides that encode the antibodies of the invention (e.g., mouse monoclonal antibody produced from clone 2B6 or 3H7, with ATCC accession numbers PTA-4591 and PTA-4592, respectively), or other monoclonal antibodies produced by immunization methods of the invention, and humanized versions thereof, and methods for producing same.

The present invention encompass the polynucleotide encoding the heavy chain of the 2B6 antibody, with ATCC accession number PTA-4591, as disclosed in SEQ ID No. 1. The present invention also encompasses the polynucleotide encoding the light chain of the 2B6 antibody with ATCC accession number PTA-4591, as disclosed in SEQ ID No. 3.

The methods of the invention also encompass polynucleotides that hybridize under various stringency, e.g., high stringency, intermediate or lower stringency conditions, to polynucleotides that encode an antibody of the invention. The hybridization can be performed under various conditions of stringency. By way of example and not limitation, procedures using conditions of low stringency are as follows (see also Shilo and Weinberg, 1981, *Proc. Natl. Acad. Sci. U.S.A.* 78, 6789-6792). Filters containing DNA are pretreated for 6 h at 40° C. in a solution containing 35% formamide, 5×SSC, 50 mM Tris-HCl (pH 7.5), 5 mM EDTA, 0.11% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×$10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987-1997, Current Protocols, © 1994-1997 John Wiley and Sons, Inc.; see especially, Dyson, 1991, "Immobilization of nucleic acids and hybridization analysis," In: Essential Molecular Biology: A Practical Approach, Vol. 2, T. A. Brown, ed., pp. 111-156, IRL Press at Oxford University Press, Oxford, UK).

The polynucleotides may be obtained, and the nucleotide sequence of the polynucleotides determined, by any method known in the art.

A polynucleotide encoding an antibody may be generated from nucleic acid from a suitable source (e.g., a cDNA library generated from, or nucleic acid, preferably poly A+ RNA, isolated from, any tissue or cells expressing the antibody, such as hybridoma cells selected to express an antibody of the invention, e.g., 2B6 or 3H7) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions). Preferably, the polynucleotide generated by the combination of the framework regions and CDRs encodes an antibody that specifically binds to FcγRIIB with greater affinity than said antibody binds FcγRIIA. Preferably, as discussed supra, one or more amino acid substitutions may be made within the framework regions, and, preferably, the amino acid substitutions improve binding of the antibodies of the invention to FcγRIIB.

In another embodiment, human libraries or any other libraries available in the art, can be screened by standard techniques known in the art, to clone the nucleic acids encoding the antibodies of the invention.

5.2.2 Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al., 1990, *Molecular Cloning, A Laboratory Manual*, 2d Ed., Cold Spring Harbor Laboratory, Cold Spring Harbor, N.Y. and Ausubel et al. eds., 1998, *Current Protocols in Molecular Biology*, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibodies of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45: 101; Cockett et al., 1990, *Bio/Technology* 8:2).

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphatic cells (see U.S. Pat. No. 5,807,715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Bio. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:817) genes can be employed in tk-, hgprt- or aprt- cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 *Clinical Pharmacy* 12:488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1; and hygro, which confers resistance to hygromycin (Santerre et al., 1984, *Gene* 30:147).

The expression levels of an antibody of the invention can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

5.3 Prophylactic and Therapeutic Methods

The present invention encompasses antibody-based therapies which involve administering one or more of the antibodies of the invention to an animal, preferably a mammal, and most preferably a human, for preventing, treating, or ameliorating symptoms associated with a disease, disorder, or infection, associated with aberrant levels or activity of FcγRIIB and/or treatable by altering immune function associated with FcγRIIB activity or enhancing cytotoxic activity of a second therapeutic antibody or enhancing efficacy of a vaccine composition. In some embodiments, therapy by administration of one or more antibodies of the invention is combine with administration of one or more therapies such as, but not limited to, chemotherapies, radiation therapies, hormonal therapies, and/or biological therapies/immunotherapies.

Prophylactic and therapeutic compounds of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

Antibodies may be provided in pharmaceutically acceptable compositions as known in the art or as described herein. As detailed below, the antibodies of the invention can be used in methods of treating cancer (particularly to enhance passive immunotherapy or efficacy of a cancer vaccine), autoimmune disease, inflammatory disorders or allergies (e.g., to enhance efficacy of a vaccine for treatment of allergy).

Antibodies of the present invention that function as a prophylactic and or therapeutic agent of a disease, disorder, or infection can be administered to an animal, preferably a mammal and most preferably a human, to treat, prevent or ameliorate one or more symptoms associated with the disease, disorder, or infection. Antibodies of the invention can be administered in combination with one or more other prophylactic and/or therapeutic agents useful in the treatment, prevention or management of a disease, disorder, or infection associated with aberrant levels or activity of FcγRIIB and/or treatable by altering immune function associated with FcγRIIB activity. In certain embodiments, one or more antibodies of the invention are administered to a mammal, preferably a human, concurrently with one or more other therapeutic agents useful for the treatment of cancer. The term "concurrently" is not limited to the administration of prophylactic or therapeutic agents at exactly the same time, but rather it is meant that antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56th ed., 2002).

The antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies and, increase immune response. The antibodies of this invention may also be advantageously utilized in combination with one or more drugs used to treat a disease, disorder, or infection such as, for example anti-cancer agents, anti-inflammatory agents or anti-viral agents, e.g., as detailed in sections 5.4.6 and 5.4.5 below.

5.3.1 Cancers

Antibodies of the invention can be used alone or in combination with other therapeutic antibodies known in the art to prevent, inhibit or reduce the growth of primary tumores or metastasis of cancerous cells. In one embodiment, antibodies of the invention can be used in combination with antibodies used in cancer immunotherapy. The invention encompasses the use of the antibodies of the invention in combination with another therapeutic antibody to enhance the efficacy of such immunotherapy by increasing the potency of the therapeutic antibody's effector function, e.g., ADCC, CDC, phagocytosis, opsonization, etc. Although not intending to be bound by a particular mechanism of action antibodies of the invention block FcγRIIB, preferably on monocytes and macrophages and thus enhance the therapeutic benefits a clinical efficacy of tumor specific antibodies by, for example, enhancing clearance of the tumors mediated by activating fcγRs. Accordingly, the invention provides methods of preventing or treating cancer characterized by a cancer antigen, when administered in combination with another antibody that specifically binds a cancer antigen and is cytotoxic. The antibodies of the invention are useful for prevention or treatment of cancer, particularly in potentiating the cytotoxic activity of cancer antigen-specific therapeutic antibodies with cytotoxic activity to enhance tumor cell killing by the antibodies of the invention and/or enhancing for example, ADCC activity or CDC activity of the therapeutic antibodies. In a specific embodiment, an antibody of the invention, when administered alone or in combination with a cytotoxic therapeutic antibody, inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in absence of said antibody of the invention. In a preferred embodiment, antibodies of the invention in combination with a cytotoxic therapeutic antibody inhibit or reduce the growth of primary tumor or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibodies.

The transition from a normal to a malignant state is a multistep process involving genetic and epigenetic changes. In fact, numerous alterations occur in the cellular regulatory circuits that facilitate this progression which enables tumor cells to evade the commitment to terminal differentiation and quiescence that normally regulate tissue homeostasis. Certain genes have been implicated in invasiveness and metastatic potential of cancer cells such as CSF-1 (colony stimulating factor 1 or macrophage colony stimulating factor). Although not intending to be bound by a particular mechanism of action, CSF-1 may mediate tumor progression and metastasis by recruiting macrophages to the tumor site where they promote progression of tumor. It is believed that macrophages have a trophic role in mediating tumor progression and metastasis perhaps by the secretion of angiogenic factors, e.g., thymidine phosphorylase, vascular endothelial-derived growth factor; secretion of growth factors such as epidermal growth factor that could act as a paracrine factor on tumor cells, and thus promoting tumor cell migration and invasion into blood vessels. (See, e.g., Lin et al., 2001, *J. Exp. Med.* 193(6): 727-739; Lin et al., 2002, *Journal of Mammary Gland*

*Biology and Neoplasam* 7(2): 147-162; Scholl et al., 1993, *Molecular Carcinogenesis,* 7: 207-11; Clynes et al., 2000, *Nature Medicine,* 6(4): 443-446; Fidler et al., 1985, *Cancer Research,* 45: 4714-26).

The invention encompasses using the antibodies of the invention to block macrophage mediated tumor cell progression and metastasis. The antibodies of the invention are particularly useful in the treatment of solid tumors, where macrophage infiltration occurs. The antagonistic antibodies of the invention are particularly useful for controlling, e.g., reducing or eliminating, tumor cell metastasis, by reducing or eliminating the population of macrophages that are localized at the tumor site. In some embodiments, the antibodies of the invention are used alone to control tumor cell metastasis. Although not intending to be bound by a particular mechanism of action the antagonistic antibodies of the invention, when administered alone bind the inhibitory FcγRIIB on macrophages and effectively reduce the population of macrophages and thus restrict tumor cell progression. The antagonistic antibodies of the invention reduce, or preferably eliminate macrophages that are localized at the tumor site, since FcγRIIB is preferentially expressed on activated monocytes and macrophages including tumor-infiltrating macrophages. In some embodiments, the antibodies of the invention are used in the treatment of cancers that are characterized by the overexpression of CSF-1, including but not limited to breast, uterine, and ovarian cancers.

The invention further encompasses antibodies that effectively deplete or eliminate immune cells other than macrophages that express FcγRIIB, e.g., dendritic cells and B-cells. Effective depletion or elimination of immune cells using the antibodies of the invention may range from a reduction in population of the immune cells by 50%, 60%, 70%, 80%, preferably 90%, and most preferably 99%. Thus, the antibodies of the invention have enhanced therapeutic efficacy either alone or in combination with a second antibody, e.g., a therapeutic antibody such as anti-tumor antibodies, anti-viral antibodies, and anti-microbial antibodies. In some embodiments, the therapeutic antibodies have specificity for a cancer cell or an inflammatory cell. In other embodiments, the second antibody binds a normal cell. Although not intending to be bound by a particular mechanism of action, when the antibodies of the invention are used alone to deplete FcγRIIB-expressing immune cells, the population of cells is redistributed so that effectively the cells that are remaining have the activating Fc receptors and thus the suppression by FcγRIIB is alleviated. When used in combination with a second antibody, e.g., a therapeutic antibody the efficacy of the second antibody is enhanced by increasing the Fc-mediated effector function of the antibody.

Cancers and related disorders that can be treated or prevented by methods and compositions of the present invention include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma, gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, classic (typical, spermatocytic, nonseminoma, embryonal carcinoma, teratoma carcinoma, choriocarcinoma (yolk-sac tumor), prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, superficial spreading melanoma, nodular melanoma, lentigo malignant melanoma, acral lentiginous melanoma; kidney cancers including but not limited to, renal cell cancer, adenocarcinoma, hypemephroma, fibrosarcoma, transitional cell cancer (renal pelvis and/or uterer); Wilms' tumor; bladder cancers including but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocareinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

Cancers associated with the cancer antigens may be treated or prevented by administration of the antibodies of the invention in combination with an antibody that binds the cancer antigen and is cytotoxic. In one particular embodiment, the antibodies of the invention enhance the antibody mediated cytotoxic effect of the antibody directed at the particular cancer antigen. For example, but not by way of limitation, cancers associated with the following cancer antigen may be treated or prevented by the methods and compositions of the invention. KS1/4 pan-carcinoma antigen (Perez and Walker, 1990, *J. Immunol.* 142:32-37; Bumal, 1988, *Hybridoma* 7(4): 407-415), ovarian carcinoma antigen (CA125) (Yu et al., 1991, *Cancer Res.* 51(2):48-475), prostatic acid phosphate (Tailor et al., 1990, *Nucl. Acids Res.* 18(1):4928), prostate specific antigen (Henttu and Vihko, 1989, *Biochem. Biophys. Res. Comm.* 10(2):903-910; Israeli et al., 1993, Cancer Res. 53:227-230), melanoma-associated antigen p97 (Estin et al., 1989, *J. Natl. Cancer Instit.* 81(6):445-44), melanoma antigen gp75 (Vijayasardahl et al., 1990, *J. Exp. Med.* 171(4): 1375-1380), high molecular weight melanoma antigen (HMW-MAA) (Natali et al., 1987, *Cancer* 59:55-3; Mittelman et al., 1990, *J. Clin. Invest.* 86:2136-2144)), prostate specific membrane antigen, carcinoembryonic antigen (CEA) (Foon et al., 1994, *Proc. Am. Soc. Clin. Oncol.* 13:294), polymorphic epithelial mucin antigen, human milk fat globule antigen, Colorectal tumor-associated antigens such as: CEA, TAG-72 (Yokata et al., 1992, *Cancer Res.* 52:3402-3408), CO17-1A (Ragnhammar et al., 1993, *Int. J. Cancer* 53:751-758); GICA 19-9 (Herlyn et al., 1982, *J. Clin. Immunol.* 2:135), CTA-1 and LEA, Burkitt's lymphoma antigen-38.13, CD19 (Ghetie et al., 1994, *Blood* 83:1329-1336), human B-lymphoma antigen-$CD_2O$ (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46:3917-3923), antigens of fibrosarcoma, human leukemia T cell antigen-Gp37 (Bhattacharya-Chatterjee et al., 1988, *J. of Immun.* 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245:301-304), differentiation antigen (Feizi, 1985, *Nature* 314:53-57) such as I antigen found in fetal erthrocytes and primary endoderm, I(Ma) found in gastric adencarcinomas, M18 and M39 found in breast epithelium, SSEA-1 found in myeloid cells, VEP8, VEP9, Myl, VIM-D5, and $D_1$ 56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma, CO-514 (blood group $Le^a$) found in adenocarcinoma, NS-10 found in adenocarcinomas, CO-43 (blood group $Le^b$), G49, EGF receptor, (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, *The Cancer Journal* 4:62).

The antibodies of the invention can be used in combination with any therapeutic cancer antibodies known in the art to enhance the efficacy of treatment. For example, the antibodies of the invention can be used with any of the antibodies in Table 3, that have demonstrated therapeutic utility in cancer treatment. The antibodies of the invention enhance the efficacy of treatment of the therapeutic cancer antibodies by enhancing at least one antibody-mediated effector function of said therapeutic cancer antibodies. In one particular embodiment, the antibodies enhance the efficacy of treatment by enhancing the complement dependent cascade of said therapeutic cancer antibodies. In another embodiment of the invention, the antibodies of the invention enhance the efficacy of treatment by enhancing the phagocytosis and opsonization of the targeted tumor cells. In another embodiment of the invention, the antibodies of the invention enhance the efficacy of treatment by enhancing antibody-dependent cell-mediated cytotoxicity ("ADCC") in destruction of the targeted tumor cells.

Antibodies of the invention can also be used in combination with cytosine-guanine dinucteotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of cancer (See also Warren et al., 2002, Semin Oncol., 29(1 Suppl 2):93-7; Warren et al., 2000, Clin Lymphoma, 1(1):57-61, which are incorporated herein by reference).

Antibodies of the invention can be used in combination with a therapeutic antibody that does not mediate its therapeutic effect through cell killing to potentiate the antibody's therapeutic activity. In a specific embodiment, the invention encompasses use of the antibodies of the invention in combination with a therapeutic apoptosis inducing antibody with agonisitc activity, e.g., an anti-Fas antibody. Anti-Fas antibodies are known in the art and include for example, Jo2 (Ogasawara et al., 1993, Nature 364: 806) and HFE7 (Ichikawa et al., 2000, Int. Immunol. 12: 555). Although not intending to be bound by a particular mechanisms of action, FcγRIIB has been implicated in promoting anti-Fas mediated apoptosis, see, e.g., Xu et al., 2003, Journal of Immunology, 171: 562-568. In fact the extracellular domain of FcγRIIB may serve as a cross-linking agent for Fas receptors, leading to a functional complex and promoting Fas dependent apoptosis. In some embodiments, the antibodies of the invention block the interaction of anti-Fas antibodies and FcγRIIB, leading to a reduction in Fas-mediated apoptotic activity. Antibodies of the invention that result in a reduction in Fas-mediated apoptotic activity are particularly useful in combination with anti-Fas antibodies that have undesirable side effects, e.g., hepatotoxicity. In other embodiments, the antibodies of the invention enhance the interaction of anti-Fas antibodies and FcγRIIB, leading to an enhancement of Fas-mediated apoptotic activity. Combination of the antibodies of the invention with therapeutic apoptosis inducing antibodies with agonisitc activity have an enhanced therapeutic efficacy.

Therapeutic apoptosis inducing antibodies used in the methods of the invention may be specific for any death receptor known in the art for the modulation of apoptotic pathway, e.g., TNFR receptor family.

The invention provides a method of treating diseases with impaired apoptotic mediated signaling, e.g., cancer, autoimmune disease. In a specific embodiment, the invention encompasses a method of treating a disease with deficient Fas-mediated apoptosis, said method comprising administering an antibody of the invention in combination with an anti-Fas antibody.

In some embodiments, the agonistic antibodies of the invention are particularly useful for the treatment of tumors of non-hematopoietic origin, including tumors of melanoma cells. Although not intending to be bound by a particular mechanism of action, the efficacy of the agonistic antibodies of the invention is due, in part, to activation of FcγRIIB inhibitory pathway, as tumors of non-hematopoietic origin, including tumors of melanoma cells express FcγRIIB. Recent experiments have in fact shown that expression of FcγRIIB in melanoma cells modulates tumor growth by direct interaction with anti-tumor antibodies (e.g., by binding the Fc region of the anti-tumor antibodies) in an intracytoplasmic-dependent manner (Cassard et al., 2002, Journal of Clinical Investigation, 110(10): 1549-1557).

In some embodiments, the invention encompasses use of the antibodies of the invention in combination with therapeutic antibodies that immunospecifically bind to tumor antigens that are not expressed on the tumor cells themselves, but rather on the surrounding reactive and tumor supporting, non-malignant cells comprising the tumor stroma. The tumor stroma comprises endothelial cells forming new blood vessels and stromal fibroblasts surrounding the tumor vasculature. In a specific embodiment, an antibody of the invention is used in combination with an antibody that immunospecifically binds a tumor antigen on an endothelial cell. In a preferred embodiment, an antibody of the invention is used in combination with an antibody that immunospecifically binds a tumor antigen on a fibroblast cell, e.g., fibroblast activation protein (FAP). FAP is a 95 KDa homodimeric type II glycoprotein which is highly expressed in stromal fibroblasts of many solid tumors, including, but not limited to lung, breast, and colorectal carcinomas. (See, e.g., Scanlan et al., 1994; Proc. Natl. Acad. USA, 91: 5657-61; Park et al., 1999, J. Biol. Chem., 274: 36505-12; Rettig et al., 1988, Proc. Natl. Acad. Sci. USA 85: 3110-3114; Garin-Chesea et al., 1990, Proc. Natl. Acad. Sci. USA 87: 7235-7239). Antibodies that immunospecifically bind FAP are known in the art and encompassed within the invention, see, e.g., Wuest et al., 2001, Journal of Biolechnology, 159-168; Mersmann et al., 2001, Int. J. Cancer, 92: 240-248; U.S. Pat. No. 6,455,677; all of which are incorporated herein in by reference in their entireties.

Recently IgE's have been implicated as mediators of tumor growth and in fact IgE-targeted immediate hypersensitivity and allergic inflammation reactions have been proposed as possible natural mechanisms involved in anti-tumor responses (For a review see, e.g., Mills et al., 1992, Am. Journal of Epidemiol. 122: 66-74; Eriksson et al., 1995, Allergy 50: 718-722). In fact a recent study has shown loading tumor cells with IgEs reduces tumor growth, leading in some instances to tumor rejection. According to the study, IgE loaded tumor cells not only possess a therapeutic potential but also confer long term antitumor immunity, including activation of innate immunity effector mechanism and T-cell mediated adaptive immune response, see Reali et al., 2001, Cancer Res. 61: 5516-22; which is incorporated herein by reference in its entirety. The antagonistic antibodies of the invention may be used in the treatment and/or prevention of cancer in combination with administration of IgEs in order to enhance the efficacy of IgE-mediated cancer therapy. Although not intending to be bound by a particular mechanism of action the antibodies of the invention enhance the therapeutic efficacy of IgE treatment of tumors, by blocking the inhibitory pathway. The antagonistic antibodies of the invention may enhance the therapeutic efficacy of IgE mediated cancer therapy by (i) enhancing the delay in tumor growth; (ii) enhancing the decrease in the rate of tumor progression; (iii) enhancing tumor rejection; or (iv) enhancing protective immune relative to treatment of cancer with IgE alone.

Cancer therapies and their dosages, routes of administration and recommended usage are known in the art and have

5.3.2 B Cell Malignancies

The agonistic antibodies of the invention are useful for treating or preventing any B cell malignancies, particularly non-Hodgkin's lymphoma and chronic lymphocytic leukemia. FcγRIIB, is a target for deregulation by chromosomal translocation in malignant lymphoma, particularly in B-cell non-Hodgkin's lymphoma (See Callanan M. B. et al., 2000 Proc. Natl. Acad. Sci. U.S.A., 97(1):309-314). Thus, the antibodies of the invention are useful for treating or preventing any chronic lymphocytic leukemia of the B cell lineage. Chronic lymphocytic leukemia of the B cell lineage are reviewed by Freedman (See review by Freedman, 1990, Hemtaol. Oncol. Clin. North Am. 4:405). Although not intending to be bound by any mechanism of action, the agonistic antibodies of the invention inhibit or prevent B cell malignancies inhibiting B cell proliferation and/or activation. The invention also encompasses the use of the agonistic antibodies of the invention in combination with other therapies known (e.g., chemotherapy and radiotherapy) in the art for the prevention and/or treatment of B cell malignancies. The invention also encompasses the use of the agonistic antibodies of the invention in combination with other antibodies known in the art for the treatment and or prevention of B-cell malignancies. For example, the agonistic antibodies of the invention can be used in combination with the anti-C22 or anti-CD 19 antibodies disclosed by Goldenberg et al. (U.S. Pat. No. 6,306,393).

Antibodies of the invention can also be used in combination with for example but not by way of limitation, ONCOSCINT® ($^{111}$In-satumomab pantedide) (target: CEA), VERLUMA® ($^{99}$Tc-nofetumomab merpentan) (target: GP40), PROSTASCINT® (caromab pentedide) (target: PSMA), CEA-SCAN® (arcitumomab) (target: CEA), RITUXAN® (rituximab) (target: CD20), HERCEPTIN® (trastuzumab) (target: HER-2), CAMPATH® (alemtuzumab (target: CD52), MYLOTARG® (gemtuzumab ozogamicin) (target: CD33), and ZEVALIN® (ibritumomab tiuxetan) (target: CD20).

5.3.3 Autoimmune Disease and Inflammatory Diseases

The agonistic antibodies of the invention may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically effective amount of the antibodies or fragments thereof of the invention. The invention also provides methods for preventing, treating, or managing one or more symptoms associated with an inflammatory disorder in a subject further comprising, administering to said subject a therapeutically effective amount of one or more anti-inflammatory agents. The invention also provides methods for preventing, treating, or managing one or more symptoms associated with an autoimmune disease further comprising, administering to said subject a therapeutically effective amount of one or more immunomodulatory agents. Section 5.4.5 provides non-limiting examples of anti-inflammatory agents and immunomodulatory agents.

The antibodies of the invention can also be used in combination with any of the antibodies known in the art for the treatment and/or prevention of autoimmune disease or inflammatory disease. A non-limiting example of the antibodies that are used for the treatment or prevention of inflammatory disorders is presented in Table 4A, and a non-limiting example of the antibodies that are used for the treatment or prevention of autoimmune disorder is presented in Table 4B. The antibodies of the invention can for example, enhance the efficacy of treatment of the therapeutic antibodies presented in Tables 2A and 2B. For example, but not by way of limitation, the antibodies of the invention can enhance the immune response in the subject being treated with any of the antibodies in Tables 2A or 2B.

Antibodies of the invention can also be used in combination with for example but not by way of limitation, ORTHOCLONE OKT3® (muromonab), REOPRO® (abeiximab), ZENAPEX® (declizumab), SIMULEC® (basiliximab), SYNAGIS® (palivizumab), and REMICADE® (infliximab).

Antibodies of the invention can also be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of autoimmune or inflammatory disorders (Weeratna et al., 2001, FEMS Immunol Med Microbiol., 32(1):65-71, which is incorporated herein by reference).

Examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus crythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein in Section 3.1, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

Antibodies of the invention can also be used to reduce the inflammation experienced by animals, particularly mammals, with inflammatory disorders. In a specific embodiment, an antibody reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in the not administered said antibody. In another embodiment, a combination of antibodies reduce the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said antibodies.

Antibodies of the invention can also be used to prevent the rejection of transplants.

TABLE 4A

Antibodies for Inflammatory Diseases and Autoimmune Diseases that can be used in combination with the antibodies of the invention.

| Antibody Name | Target Antigen | Product Type | Isotype | Sponsors | Indication |
|---|---|---|---|---|---|
| 5G1.1 | Complement (C5) | Humanised | IgG | Alexion Pharm Inc | Rheumatoid Arthritis |
| 5G1.1 | Complement (C5) | Humanised | IgG | Alexion Pharm Inc | SLE |
| 5G1.1 | Complement (C5) | Humanised | IgG | Alexion Pharm Inc | Nephritis |
| 5G1.1-SC | Complement (C5) | Humanised | ScFv | Alexion Pharm Inc | Cardiopulmano Bypass |
| 5G1.1-SC | Complement (C5) | Humanised | ScFv | Alexion Pharm Inc | Myocardial Infarction |
| 5G1.1-SC | Complement (C5) | Humanised | ScFv | Alexion Pharm Inc | Angioplasty |
| ABX-CBL | CBL | Human | | Abgenix Inc | GvHD |
| ABX-CBL | CD147 | Murine | IgG | Abgenix Inc | Allograft rejection |
| ABX-IL8 | IL-8 | Human | IgG2 | Abgenix Inc | Psoriasis |
| ANTEGREN® | VLA-4 | Humanised | IgG | Athena/Elan | Multiple Sclerosis |
| Anti-CD11a | CD11a | Humanised | IgG1 | Genentech Inc/Xoma | Psoriasis |
| Anti-CD18 | CD18 | Humanised | Fab'2 | Genentech Inc | Myocardial infarction |
| Anti-LFA1 | CD18 | Murine | Fab'2 | Pasteur-Merieux/Immunotech | Allograft rejection |
| ANTOVA® (ruplizumab) | CD40L | Humanised | IgG | Biogen | Allograft rejection |
| ANTOVA® (ruplizumab) | CD40L | Humanised | IgG | Biogen | SLE |
| BTI-322 | CD2 | Rat | IgG | Medimmune Inc | GvHD, Psoriasis |
| CDP571 | TNF-alpha | Humanised | IgG4 | Celltech | Crohn's |
| CDP571 | TNF-alpha | Humanised | IgG4 | Celltech | Rheumatoid Arthritis |
| CDP850 | E-selectin | Humanised | | Celltech | Psoriasis |
| CORSEVIN M™ | Fact VII | Chimeric | | Centocor | Anticoagulant |
| D2E7 | TNF-alpha | Human | | CAT/BASF | Rheumatoid Arthritis |
| Hu23F2G | CD11/18 | Humanised | | ICOS Pharm Inc | Multiple Sclerosis |
| Hu23F2G | CD11/18 | Humanised | IgG | ICOS Pharm Inc | Stroke |
| IC14 | CD14 | | | ICOS Pharm Inc | Toxic shock |
| ICM3 | ICAM-3 | Humanised | | ICOS Pharm Inc | Psoriasis |
| IDEC-114 | CD80 | Primatised | | IDEC Pharm/Mitsubishi | Psoriasis |
| IDEC-131 | CD40L | Humanised | | IDEC Pharm/Eisai | SLE |
| IDEC-131 | CD40L | Humanised | | IDEC Pharm/Eisai | Multiple Sclerosis |
| IDEC-151 | CD4 | Primatised | IgG1 | IDEC Pharm/Glaxo SmithKline | Rheumatoid Arthritis |

TABLE 4A-continued

Antibodies for Inflammatory Diseases and Autoimmune Diseases that can be used in combination with the antibodies of the invention.

| Antibody Name | Target Antigen | Product Type | Isotype | Sponsors | Indication |
|---|---|---|---|---|---|
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanised | IgG | Millennium Inc (LeukoSite Inc.) | Stroke |
| LDP-01 | beta2-integrin | Humanised | IgG | Millennium Inc (LeukoSite Inc.) | Allograft rejection |
| LDP-02 | alpha4beta7 | Humanised | | Millennium Inc (LeukoSite Inc.) | Ulcerative Colitis |
| MAK-195F | TNF alpha | Murine | Fab'2 | Knoll Pharm, BASF | Toxic shock |
| MDX-33 | CD64 (FcR) | Human | | Medarex/Centeon | Autoimmune haematogical disorders |
| MDX-CD4 | CD4 | Human | IgG | Medarex/Eisai/Genmab | Rheumatoid Arthritis |
| MEDI-507 | CD2 | Humanised | | Medimmune Inc | Psoriasis |
| MEDI-507 | CD2 | Humanised | | Medimmune Inc | GvHD |
| OKT4A | CD4 | Humanised | IgG | Ortho Biotech | Allograft rejection |
| OrthoClone OKT4A | CD4 | Humanised | IgG | Ortho Biotech | Autoimmune disease |
| ORTHOCLONE OKT3 ® (muromonab) | CD3 | Murine | mIgG2a | Ortho Biotech | Allograft rejection |
| REOPRO ® (Abciximab) | gpIIbIIIa | Chimeric | Fab | Centocor/Lilly | Complications of coronary angioplasty |
| rhuMab-E25 | IgE | Humanised | IgG1 | Genentech/Novartis/Tanox Biosystems | Asthma/Allergy |
| SB-240563 | IL5 | Humanised | | GlaxoSmithKline | Asthma/Allergy |
| SB-240683 | IL-4 | Humanised | | GlaxoSmithKline | Asthma/Allergy |
| SCH55700 | IL-5 | Humanised | | Celltech/Schering | Asthma/Allergy |
| SIMULECT ® (basiliximab) | CD25 | Chimeric | IgG1 | Novartis Pharm | Allograft rejection |
| SMART a-CD3 | CD3 | Humanised | | Protein Design Lab | Autoimmune disease |
| SMART a-CD3 | CD3 | Humanised | | Protein Design Lab | Allograft rejection |
| SMART a-CD3 | CD3 | Humanised | IgG | Protein Design Lab | Psoriasis |
| ZENAPAX ® (delizumab) | CD25 | Humanised | IgG1 | Protein Design Lab/Hoffman-La Roche | Allograft rejection |

TABLE 4B

Antibodies for Autoimmune Disorders

| Antibody | Indication | Target Antigen |
|---|---|---|
| ABX-RB2 | | antibody to CBL antigen on T cells, B cells and NK cells fully human antibody from the Xenomouse |

TABLE 4B-continued

| Antibodies for Autoimmune Disorders | | |
|---|---|---|
| IL1-ra | rheumatoid arthritis | recombinant anti-inflammatory protein |
| sTNF-RI | chronic inflammatory disease rheumatoid arthritis | soluble tumor necrosis factor a - receptor type I blocks TNF action |
| 5c8 (Anti CD-40 ligand antibody) | Phase II trials were halted in Oct. 99 examine "adverse events" | CD-40 |
| IDEC 131 | systemic lupus erythyematous (SLE) | anti CD40 humanized |
| IDEC 151 | rheumatoid arthritis | primatized; anti-CD4 |
| IDEC 152 | asthma | primatized; anti-CD23 |
| IDEC 114 | psoriasis | primatized; anti-CD80 |
| MEDI-507 | rheumatoid arthritis; multiple sclerosis Crohn's disease psoriasis | anti-CD2 |
| LDP-02 (anti-b7 mAb) | inflammatory bowel disease Chron's disease ulcerative colitis | a4b7 integrin receptor on white blood cells (leukocytes) |
| SMART Anti-Gamma Interferon antibody | autoimmune disorders | Anti-Gamma Interferon |
| Verteporfin | rheumatoid arthritis | |
| THALOMID ® (thalidomide) | leprosy —approved for market Chron's disease rheumatoid arthritis | inhibitor of tumor necrosis factor alpha (TNF alpha) |
| SelCIDs (selective cytokine inhibitory drugs) | | highly specific inhibitors of phosphodiesterase type 4 enzyme (PDE-4) increases levels of cAMP (cyclic adenosine monophosphate) activates protein kinase A (PKA) blocks transcription factor NK-kB prevents transcription of TNF-a gene decreases production of TNF-a |
| IMiDs (immunomodulatory drugs) | general autoimmune disorders | structural analogues of thalidomideinhibit TNF-a |
| MDX-33 | blood disorders caused by autoimmune reactions Idiopathic Thrombocytopenia Purpurea (ITP) autoimmune hemolytic anemia | monoclonal antibody against FcRI receptors |
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response regulates cytokines) |
| VX-745 | specific to inflammation involved in chemical signaling of immune response onset and progression of inflammation | inhibitor of P38MAP kinase mitogen activated protein kinase |
| ENBREL ® (etanercept) | | targets TNF (tumor necrosis factor) |
| IL-8 | | fully human MAB against IL-8 (interleukin 8) (blocks IL-8 blocks inflammatory response) |
| 5G1.1 | rheumatoid arthritis pemphigoid (dangerous skin rash) psoriasis lupus | a C5 complement inhibitor |
| Apogen MP4 | | recombinant antigen selectively destroys disease associated T-cells |

TABLE 4B-continued

Antibodies for Autoimmune Disorders induces apoptosis
T-cells eliminated by programmed cell death
no longer attack body's own cells
specific apogens target specific T-cells

| Company Rankings | Product | Development Stage |
|---|---|---|
| Immunex | ENBREL ® (etanercept) | on market |
| Amgen | IL1-ra, sTNF-RI | Phase II/III |
| Abgenix | AGX-RB2, IL-8 | preclinical, Phase I |
| Alexion | 5G1.1, Apogen MP4 | Phase II, preclinical |
| Biogen | 5c8 | Phase II (halted) |
| IDEC | 131, 151, 152, 114 | Phase I and II |
| MedImmune | MEDI 507 | Phase I/II |
| Millennium | LDP-02, | Phase II |
| Protein Design Labs | Anti-Gamma Interferon | preclinical |
| Medarex | MDX-33, MDX-CD4 | Phase II, Phase I |
| QLT Photo Therapeutics | Vertiporfin | Phase I |
| Celegene | THALOMID ®, (thalidomide), SelCIDs, IMiDs | on market, preclinical |
| Vertex | VX-497, VX-740, VX-745 | Phase II, Phase II, Phase II |

5.3.4 Allergy

The invention provides methods for treating or preventing an IgE-mediated and or FcεRI mediated allergic disorder in a subject in need thereof, comprising administering to said subject a therapeutically effective amount of the agonistic antibodies or fragments thereof of the invention. Although not intending to be bound by a particular mechanism of action, antibodies of the invention are useful in inhibiting FcεRI-induced mast cell activation, which contributes to acute and late phase allergic responses (Metcalfe D. et al. 1997, *Physiol. Rev.* 77:1033). Preferably, the agonistic antibodies of the invention have enhanced therapeutic efficacy and/or reduced side effects in comparison with the conventional methods used in the art for the treatment and/or prevention of IgE mediated allergic disorders. Conventional methods for the treatment and/or prevention of IgE mediated allergic disorders include, but are not limited to, anti-inflammatory drugs (e.g., oral and inhaled corticosteroids for asthma), antihistamines (e.g., for allergic rhinitis and atopic dermatitis), cysteinyl leukotrienes (e.g., for the treatment of asthma); anti-IgE antibodies; and specific immunotherapy or desensitization.

Examples of IgE-mediated allergic responses include, but are not limited to, asthma, allergic rhinitis, gastrointestinal allergies, eosinophilia, conjunctivitis, atopic dermatitis, urticaria, anaphylaxis, or golmerular nephritis.

The invention encompasses molecules, e.g., immunoglobulins, engineered to form complexes with FcεRI and human FcγRIIB, i.e., specifically bind FcεRI and human FcγRIIB. Preferably, such molecules have therapeutic efficacy in IgE and FcεRI-mediated disorders. Although not intending to be bound by a particular mechanism of action, the therapeutic efficacy of these engineered molecules is, in part, due to their ability to inhibit mast cell and basophil function.

In a specific embodiment, molecules that specifically bind FcεRI and human FcγRIIB are chimeric fusion proteins comprising a binding site for FcεRI and a binding site for FcγRIIB. Such molecules may be engineered in accordance with standard recombinant DNA methodologies known to one skilled in the art. In a preferred specific embodiment, a chimeric fusion protein for use in the methods of the invention comprises an F(ab') single chain of an anti-FcγRIIB monoclonal antibody of the invention fused to a region used as a bridge to link the huFcε to the C-terminal region of the F(ab') single chain of the anti-FcγRIIB monoclonal antibody. One exemplary chimeric fusion protein for use in the methods of the invention comprises the following: $V_L/C_H$ (FcγRIIB)-hinge-$V_H/C_H$ (FcγRIIB)-LINKER-$C_H\varepsilon 2$-$C_H\varepsilon 3$-$C_H\varepsilon 4$. The linker for the chimeric molecules may be five, ten, preferably fifteen amino acids in length. The length of the linker may vary to provide optimal binding of the molecule to both FcγRIIB and FcεRI. In a specific embodiment, the linker is a 15 amino acid linker, consisting of the sequence: $(Gly_4Ser)_3$. Although not intending to be bound by a particular mechanism of action, the flexible peptide linker facilitates chain pairing and minimizes possible refolding and it will also allow the chimeric molecule to reach the two receptors, i.e., FcγRIIB and FcεRI on the cells and cross-link them. Preferably, the chimeric molecule is cloned into a mammalian expression vector, e.g., pCI-neo, with a compatible promoter, e.g., cytomegalovirus promoter. The fusion protein prepared in accordance with the methods of the invention will contain the binding site for FcεRI ($CH\varepsilon 2CH\varepsilon 3$) and for FcγRIIB (VL/CL,-hinge-VH/CH). The nucleic acid encoding the fusion protein prepared in accordance with the methods of the invention is preferably transfected into 293 cells and the secreted protein is purified using common methods known in the art.

Binding of the chimeric molecules to both human FcεRI and FcγRIIB may be assessed using common methods known to one skilled in the art for determining binding to an FcγR. Preferably, the chimeric molecules of the invention have therapeutic efficacy in treating IgE mediated disorders, for example, by inhibiting antigen-driven degranulation and inhibition of cell activation. The efficacy of the chimeric molecules of the invention in blocking IgE driven FcεRI-mediated mast cell degranulation may be determined in transgenic mice, which have been engineered to express the human FcεRα and human FcγRIIB, prior to their use in humans.

The invention provides the use of bispecific antibodies for the treatment and/or prevention of IgE-mediated and/or FcεRI-mediated allergic disorders. A bispecific antibody (BsAb) binds to two different epitopes usually on distinct antigens. BsAbs have potential clinical utility and they have been used to target viruses, virally infected cells and bacterial pathogens as well as to deliver thrombolitic agents to blood clots (Cao Y., 1998 *Bioconj. Chem* 9: 635-644; Koelemij et al., 1999, *J. Immunother.*, 22, 514-524; Segal et al., *Curr. Opin. Immunol.*, 11, 558-562). The technology for the production of BsIgG and other related bispecific molecules is available (see, e.g., Carter et al., 2001 *J. of Immunol. Methods*, 248, 7-15; Segal et al., 2001, *J. of Immunol. Methods*, 248, 7-15, which are incorporated herein by reference in their entirety). The instant invention provides bispecific antibodies containing one F(ab') of the anti-FcγRIIB antibody and one F(ab') of an available monoclonal anti-huIgE antibody which aggregates two receptors, FcγRIIB and FcεRI, on the surface of the same cell. Any methodology known in the art and disclosed herein may be employed to generate bispecific antibodies for use in the methods of the invention. In a specific embodiment, the BsAbs will be produced by chemically cross-linking F(ab') fragments of an anti-FcγRIIB antibody and an anti-huIgE antibody as described previously, see, e.g., Glennie et al., 1995, *Tumor Immunobiology*, Oxford University press, Oxford, p. 225; which is incorporated herein by reference in its entirety). The F(ab') fragments may be produced by limited proteolysis with pepsin and reduced with mercaptoethanol amine to provide Fab' fragments with free hinge-region sulfhydryl (SH) groups. The SH group on one of the Fab' (SH) fragments may be alkylated with excess O-phenylenedimaleimide (O-PDM) to provide a free maleimide group (mal). The two preparations Fab'(mal) and Fab'(SH) may be combined at an appropriate ratio, preferably 1:1 to generate heterodimeric constructs. The BsAbs can be purified by size exclusion chromatography and characterized by HPLC using methods known to one skilled in thr art.

In particular, the invention encompasses bispecific antibodies comprising a first heavy chain-light chain pair that binds FcγRIIB with greater affinity than said heavy chain-light chain pair binds FcγRIIA, and a second heavy chain-light chain pair that binds IgE receptor, with the provision that said first heavy chain-light chain pair binds FcγRIIB first. The bispecific antibodies of the invention can be engineered using standard techniques known in the art to ensure that the binding to FcγRIIB precedes the binding to the IgE receptor. It will be understood to one skilled in the art to engineer the bispecific antibodies, for example, such that said bispecific antibodies bind FcγRIIB with greater affinity than said antibodies bind IgE receptor. Additionally, the bispecific antibodies can be engineered by techniques known in the art, such that the hinge size of the antibody can be increased in length, for example, by adding linkers, to provide the bispecific antibodies with flexibility to bind the IgE receptor and FcγRIIB receptor on the same cell.

The antibodies of the invention can also be used in combination with other therapeutic antibodies or drugs known in the art for the treatment or prevention of IgE-mediated allergic disorders. For example, the antibodies of the invention can be used in combination with any of the following: azelastine (ASTELIN®), beclomethasone dipropionate inhaler, (VANCERIL®), beclomethasone dipropionate nasal inhaler/spray (VANCENASE®), Beconase budesonide nasal inhaler/spray (RHINOCORT®), cetirizine (ZYRTEC®), chlorpheniramine, pseudoephedrine, Deconamine (SUDAFED®), cromolyn (NASALCROM®, INTAL®, OPTICROM®), desloratadine (CLARINEX®), fexofenadine and pseudoephedrine (ALEGRA-D®), fexofenadinea (ALLEGRA®), flunisolide nasal sprays (NASALIDE®), fluticasone propionate nasal inhaler/spray, (FLONASE®), fluticasone propionate oral inhaler (FLOVENT®), hydroxyzine, (VISTARIL®), ATARAX®), loratadine, pseudoephedrine, (CLARITIN-D®), loratadine (CLARITIN®), prednisolone (PREDNISOLONE®, PEDIAPRED® Oral Liquid, MEDROL® prednisone, DELTASONE®, Liquid Predsalmeterol), salmeterol xinafoate (SEREVENT®), triamcinolone acetonide inhaler (AZMACORT®), triamcinolone acetonide nasal inhaler/spray (NASACORT®, or NASACORT AQ®). Antibodies of the invention can be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of IgE-mediated allergic disorders (See also Weeratna et al., 2001, *FEMS Immunol Med Microbiol.*, 32(1):65-71, which is incorporated herein by reference).

The invention encompasses the use of the antibodies of the invention in combination with any therapeutic antibodies known in the art for the treatment of allergy disorders, e.g., XOLAIR™ (Omalizumab; Genentech); rhuMAB-E25 (BioWorld Today, Nov. 10, 1998, p. 1; Genentech); CGP-51901 (humanized anti-IgE antibody), etc.

Additionally, the invention encompasses the use of the antibodies of the invention in combination with other compositions known in the art for the treatment of allergy disorders. In particular methods and compositions disclosed in Carson et al. (U.S. Pat. No. 6,426,336; US 2002/0035109 µl; US 2002/0010343) is incorporated herein by reference in its entirety.

5.3.5 Immunomodulatory Agents and Anti-Inflammatory Agents

The method of the present invention provides methods of treatment for autoimmune diseases and inflammatory diseases comprising administration of the antibodies of the present invention in conjunction with other treatment agents. Examples of immunomodulatory agents include, but are not limited to, methothrexate, ENBREL® (etanerecent), REMICADE™® (infliximab), leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYNT™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRONT™), cortisone, hydrocortisone, prednisone (DELTASONE™), prednisolone, triamcinolone, azulfidine, and eicosanoids such as prostaglandins, thromboxanes, and leukotrienes.

5.3.6 Anti-Cancer Agents and Therapeutic Antibodies

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-LC11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Anti-cancer agents that can be used in combination with antibodies of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil, fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecroprn B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarnycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; ririmostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxyiriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™® (edrecolomab) which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); CAMPATH® (alemtuzumab) 1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™® (epratuzumab) which is a humanized anti-CD22 IgG antibody (Immunomedics); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BAS F); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-a IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™® (ruplizumab) is a humanized anti-CD40L IgG antibody (Biogen); ANTEGREN™® (natalizumab) is a humanized anti-VLA-4 IgG antibody (Elan); and CAT-152 is a human anti-TGF-β$_2$ antibody (Cambridge Ab Tech).

Other examples of therapeutic antibodies that can be used in combination with the antibodies of the invention are presented in Table 5.

TABLE 5

Monoclonal antibodies for Cancer Therapy that can be used in combination with the antibodies of the invention.

| Company | Product | Disease | Target |
|---|---|---|---|
| Abgenix | ABX-EGF | Cancer | EGF receptor |
| AltaRex | OVAREX ® (oregoromab) | ovarian cancer | tumor antigen CA125 |
|  | BravaRex | metastatic cancers | tumor antigen MUC1 |
| Antisoma | THERAGYN ® (pemtumomabytrrium-90) | ovarian cancer | PEM antigen |
|  | Therex | breast cancer | PEM antigen |
| Boehringer Ingelheim | blvatuzumab | head & neck cancer | CD44 |
| Centocor/J&J | PANOREX ® (edrecolomab) | Colorectal cancer | 17-1A |
|  | REOPRO ® (abciximab) | PTCA | gp IIIb/IIIa |
|  | REOPRO ® (abciximab) | Acute MI | gp IIIb/IIIa |
|  | REOPRO ® (abciximab) | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | HERCEPTIN ® (trastuzumab) | metastatic breast cancer | HER-2 |
|  | HERCEPTIN ® (trastuzumab) | early stage breast cancer | HER-2 |
|  | RITUXAN ® (rituximab) | Relapsed/refractory low-grade or follicular NHL | CD20 |
|  | RITUXAN ® (rituximab) | intermediate & high-grade NHL | CD20 |
|  | MAb-VEGF | NSCLC, metastatic | VEGF |
|  | MAb-VEGF | Colorectal cancer, metastatic | VEGF |
|  | AMD Fab | age-related macular degeneration | CD18 |
|  | E-26 (2$^{nd}$ gen. IgE) | allergic asthma & rhinitis | IgE |
| IDEC | ZEVALIN ® (RITUXAN ® (rituximab) + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
|  | Cetuximab + cisplatin & radiation | newly diagnosed or recurrent head & neck cancer | EGF receptor |
|  | Cetuximab + gemcitabine | newly diagnosed metastatic pancreatic carcinoma | EGF receptor |
|  | Cetuximab + cisplatin + 5FU or Taxol | recurrent or metastatic head & neck cancer | EGF receptor |
|  | Cetuximab + carboplatin + paclitaxel | newly diagnosed non-small cell lung carcinoma | EGF receptor |
|  | Cetuximab + cisplatin | head & neck cancer (extensive | EGF receptor |

TABLE 5-continued

Monoclonal antibodies for Cancer Therapy that can be used in combination with the antibodies of the invention.

| Company | Product | Disease | Target |
|---|---|---|---|
| | | incurable local-regional disease & distant metasteses) | |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LYMPHOCIDE ® (epratuzumab) | Non-Hodgkins lymphoma | CD22 |
| | LYMPHOCIDE ® (epratuzumab) Y-90 | Non-Hodgkins lymphoma | CD22 |
| | CEA-CIDE ® (labetuzumab) | metastatic solid tumors | CEA |
| | CEA-CIDE ® (labetuzumab) Y-90 | metastatic solid tumors | CEA |
| | CEA-SCAN ® (Tc-99m-labeled arcitumomab) | colorectal cancer (radioimaging) | CEA |
| | CEA-SCAN ® (Tc-99m-labeled arcitumomab) | Breast cancer (radioimaging) | CEA |
| | CEA-SCAN ® (Tc-99m-labeled arcitumomab) | lung cancer (radioimaging) | CEA |
| | CEA-SCAN > (Tc-99m-labeled arcitumomab) | intraoperative tumors (radioimaging) | CEA |
| | LEUKOSCAN ® (Tc-99m-labeled sulesomab) | soft tissue infection (radioimaging) | CEA |
| | LymphoScan (Tc-99m) bectumomab) | lymphomas (radioimaging) | CD22 |
| | AFP-Scan (Tc-99m-labeled) | liver 7 gem-cell cancers (radioimaging) | AFP |
| Intracel | HumaRAD-HN (+ yttrium-90) | head & neck cancer | NA |
| | HumaSPECT | colorectal imaging | NA |
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v \beta_3$ |
| Merck KGaA | MAb 425 | Various cancers | EGF receptor |
| | IS-IL-2 | Various cancers | Ep-CAM |
| Millennium | CAMPATH ® (alemtuzumab) | chronic lymphocytic leukemia | CD52 |
| NeoRx | CD20-streptavidin (+ biotin-yttrium 90) | Non-Hodgkins lymphoma | CD20 |
| | Avidicin (albumin + NRLU13) | metastatic cancer | NA |
| Peregrine | ONCOLYM ® (+ iodine-131) | Non-Hodgkins lymphoma | HLA-DR 10 beta |
| | COTARA (+ iodine-131) | unresectable malignant glioma | DNA-associated proteins |

TABLE 5-continued

Monoclonal antibodies for Cancer Therapy that can be used in combination with the antibodies of the invention.

| Company | Product | Disease | Target |
|---|---|---|---|
| Pharmacia Corporation | C215 (+ staphylococcal enterotoxin) | pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | NUVION ® (visilizumab) | T cell malignancies | CD3 |
| | SMART M195 | AML | CD33 |
| | SMART 1D10 | NHL | HLA-DR antigen |
| Titan | CEAVac | colorectal cancer, advanced | CEA |
| | TRIGEM ® | metastatic melanoma & small cell lung cancer | GD2-ganglioside |
| | TRIAB ® | metastatic breast cancer | MUC-1 |
| Trilex | CEAVAC ® | colorectal cancer, advanced | CEA |
| | TRIGEM ® | metastatic melanoma & small cell lung cancer | GD2-ganglioside |
| | TRIAB ® | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+ gelonin toxin) | gliorna, melanoma & neuroblastoma | NA |
| Xoma | RITUXAN (rituzimab) | Relapsed/refractory low-grade or follicular NHL | CD20 |
| | RITUXAN (rituzimab) | intermediate & high-grade NHL | CD20 |
| | ING-1 | adenomcarcinoma | Ep-CAM |

5.3.7 Vaccine Therapy

The invention provides a method for enhancing an immune response to a vaccine composition in a subject, said method comprising administering to said subject an antibody or a fragment thereof that specifically binds FcγRIIB with greater affinity than said antibody or a fragment thereof binds FcγRIIA, and a vaccine composition, wherein said antibody or a fragment thereof enhances the immune response to said vaccine composition. In one particular embodiment, said antibody or a fragment thereof enhances the immune response to said vaccine composition by enhancing antigen presentation/and or antigen processing of the antigen to which the vaccine is directed at. Any vaccine composition known in the art is useful in combination with the antibodies or fragments thereof of the invention.

In one embodiment, the invention encompasses the use of the antibodies of the invention in combination with any cancer vaccine known in the art, e.g., CANVAXIN™ (Cancer Vax, Corporation, melanoma and colon cancer); ONCOPHAGE® (HSPPC-96; Antigenics; metastatic melanoma); HER-2/neu cancer vaccine, etc. The cancer vaccines used in the methods and compositions of the invention can be, for example, antigen-specific vaccines, anti-idiotypic vaccines, dendritic cell vaccines, or DNA vaccines. The invention encompasses the use of the antibodies of the invention with cell-based vaccines as described by Segal et al. (U.S. Pat. No. 6,403,080), which is incorporated herein by reference in its entirety. The cell based vaccines used in combination with the antibodies of the invention can be either autologous or allogeneic. Briefly, the cancer-based vaccines as described by Segal et al. are based on Opsonokine™ product by Genitrix, LLC. Opsonokines™ are genetically engineered cytokines that, when mixed with tumor cells, automatically attach to the surface of the cells. When the "decorated" cells are administered as a vaccine, the cytokine on the cells activates critical antigen presenting cells in the recipient, while also allowing the antigen presenting cells to ingest the tumor cells. The antigen presenting cells are then able to instruct "killer" T cells to find and destroy similar tumor cells throughout the body. Thus, the Opsonokine™ product converts the tumor cells into a potent anti-tumor immunotherapeutic.

In one embodiment, the invention encompasses the use of the antibodies of the invention in combination with any allergy vaccine known in the art. The antibodies of the invention, can be used, for example, in combination with recombinant hybrid molecules coding for the major timothy grass pollen allergens used for vaccination against grass pollen allergy, as described by Linhart et al. (2000, *FASEB Journal*, 16(10):1301-3, which is incorporated by reference). In addition the antibodies of the invention can be used in combination with DNA-based vaccinations described by Horner et al. (2002, Allergy, 57 Suppl, 72:24-9, which is incorporated by reference). Antibodies of the invention can be used in combination with Bacille Clamett-Guerin ("BCG") vaccination as described by Choi et al. (2002, *Ann. Allergy Asthma Immunology,* 88(6): 584-91) and Barlan et al. (2002, *Journal Asthma,* 39(3):239-46), both of which are incorporated herein by reference in entirety, to downregulate IgE secretion. The antibodies of the invention are useful in treating food allergies. In particular the antibodies of the invention can be used in combination with vaccines or other immunotherapies known in the art (see Hourihane et al., 2002, *Curr. Opin. Allergy Clin. Immunol.* 2(3):227-31) for the treatment of peanut allergies.

The methods and compositions of the invention can be used in combination with vaccines, in which immunity for the antigen(s) is desired. Such antigens may be any antigen known in the art. The antibodies of the invention can be used to enhance an immune response, for example, to infectious agents, diseased or abnormal cells such as, but not limited to, bacteria (e.g., gram positive bacteria, gram negative bacteria, aerobic bacteria, Spirochetes, *Mycobacteria, Rickettsias, Chlamydias*, etc.), parasites, fungi (e.g., *Candida albicans, Aspergillus*, etc.), viruses (e.g., DNA viruses, RNA viruses, etc.), or tumors. Viral infections include, but are not limited to, human immunodeficiency virus (HIV); hepatitis A virus, hepatitis B virus, hepatitis C virus, hepatitis D virus, or other hepatitis viruses; cytomagaloviruses, herpes simplex virus-1 (-2,-3,-4,-5,-6), human papilloma viruses; Respiratory syncytial virus (RSV), Parainfluenza virus (PIV), Epstein Barr virus, or any other viral infections.

The invention encompasses the use of the antibodies of the invention to enhance a humoral and/or cell mediated response against the antigen(s) of the vaccine composition. The invention further encompasses the use of the antibodies of the invention to either prevent or treat a particular disorder, where an enhanced immune response against a particular antigen or antigens is effective to treat or prevent the disease or disorder. Such diseases and disorders include, but are not limited to, viral infections, such as HIV, CMV, hepatitis, herpes virus, measles, etc., bacterial infections, fungal and parasitic infections, cancers, and any other disease or disorder amenable to treatment or prevention by enhancing an immune response against a particular antigen or antigens.

5.4 Compositions and Methods of Administering

The invention provides methods and pharmaceutical compositions comprising antibodies of the invention. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or conjugated molecules of the invention. In a preferred aspect, an antibody or fusion protein or conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising antibodies of the invention, e.g., encapsulation in liposomes, microparticles, microcapsules, recombinant cells capable of expressing the antibody or fusion protein, receptor-mediated endocytosis (See, e.g., Wu and Wu, 1987, *J. Biol. Chem.* 262:4429-4432), construction of a nucleic acid as part of a retroviral or other vector, etc.

In some embodiments, the antibodies of the invention are formulated in liposomes for targeted delivery of the antibodies of the invention. Liposomes are vesicles comprised of concentrically ordered phopsholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545; all of which are incorporated herein by reference in their entirety.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome see, e.g., Bendas et al., 2001 *BioDrugs,* 15(4): 215-224; Allen et al., 1987 *FEBS Lett* 223: 42-6; Klibanov et al., 1990 *FEBS Lett.,* 268: 235-7; Blum et al., 1990, *Biochim. Biophys. Acta,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta,* 1062; 142-8; Allen et al., 1994, *Adv. Drug Deliv. Rev,* 13: 285-309; all of which are incorporated herein by reference in their entirety. The invention also encompasses liposomes that are adapted for specific organ targeting, see, e.g., U.S. Pat. No. 4,544,545. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al., 1982, *J. Biol. Chem.* 257: 286-288, which is incorporated herein by reference in its entirety.

The antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., Allen et al., 1995, *Stealth Liposomes*, Boca Rotan: CRC Press, 233-44; Hansen et al., 1995, *Biochim. Biophys. Acta*, 1239: 133-44; which are incorporated herein by reference in their entirety. In most preferred embodiments, immunoliposomes for use in the methods and compositions of the invention are further sterically stabilized. Preferably, the antibodies of the invention are linked covalently or non-covalently to a hydrophobic anchor, which is stably rooted in the lipid bilayer of the liposome. Examples of hydrophobic anchors include but are not limited to phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., 1997, *Gene Therapy: Advances in Pharmacology*, Volume 40, Academic Press, San Diego, Calif., p. 399-435, which is incorporated herein by reference in its entirety. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors such as pyridylthiopropionyl-phosphatidylethanolamine. See, e.g., Dietrich et al., 1996, *Biochemistry*, 35: 1100-1105; Loughrey et al., 1987, *Biochim. Biophys. Acta*, 901: 157-160; Martin et al., 1982, *J. Biol. Chem.* 257: 286-288; Martin et al., 1981, *Biochemistry*, 20: 4429-38; all of which are incorporated herein by reference in their entirety. Although not intending to be bound by a particular mechanism of action, immunoliposomal formulations comprising an antibody of the invention are particularly effective as therapeutic agents, since they deliver the antibody to the cytoplasm of the target cell, i.e., the cell comprising the FcγRIIB receptor to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The invention encompasses immunoliposomes comprising an antibody of the invention or a fragment thereof. In some embodiments, the immunoliposomes further comprise one or more additional therapeutic agents, such as those disclosed herein.

The immunoliposomal compositions of the invention comprise one or more vesicle forming lipids, an antibody of the invention or a fragment or derivative thereof, and optionally a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and gnaglioside GM1, which increases the serum half life of the liposome. Methods of conjugating hydrophilic polymers to liposomes are well known in the art and encompassed within the invention. For a review of immunoliposomes and methods of preparing them, see, e.g., PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August, ed., 1997, *Gene Therapy: Advances in Pharmacology*, Volume 40, Academic Press, San Diego, Calif., p. 399-435, all of which are incorporated herein by reference in their entireties.

Methods of administering an antibody of the invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the antibodies of the invention are packaged in a hermetically sealed container such as an ampoule or sachette indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the antibodies of the invention administered to a patient are 0.01 mg to 1000 mg/day, when used as single agent therapy. In another embodiment the antibodies of the invention are used in combination with other therapeutic compositions and the dosage administered to a patient are lower than when said antibodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In another embodiment, the compositions can be delivered in a vesicle, in particular a liposome (See Langer, *Science* 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising one or more antibodies of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of antibodies (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, *Ann. Neurol.* 25:351; Howard et al., 1989, *J. Neurosurg.* 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526, 938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bloact. Mater.* 24:853-854; and Lam et al., 1997, *Proc. Int'l Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage and frequency of administration of antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of antibodies of the invention can include a single treatment or, preferably, can include a series of treatments. In a preferred example, a subject is treated with antibodies of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

5.4.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of antibodies of the invention and a pharmaceutically acceptable carrier.

In one particular embodiment, the pharmaceutical composition comprises of a therapeutically effective amount of an antibody or a fragment thereof that binds FcγRIIB with a greater affinity than said antibody or a fragment thereof binds FcγRIIA, a cytotoxic antibody that specifically binds a cancer antigen, and a pharmaceutically acceptable carrier. In another embodiment, said pharmaceutical composition further comprises one or more anti-cancer agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with captions such as those derived from sodium, potassium, ammonium, calcium, ferric hydroxides, isopropylamine, triethylamine, 2-ethylamino ethanol, histidine, procaine, etc.

5.4.2 Gene Therapy

In a specific embodiment, nucleic acids comprising sequences encoding antibodies or fusion proteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, Science 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect, a composition of the invention comprises nucleic acids encoding an antibody, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, *Proc. Natl. Acad. Sci. USA* 86:8932-8935; and Zijlstra et al., 1989, *Nature* 342:435-438).

In another preferred aspect, a composition of the invention comprises nucleic acids encoding a fusion protein, said nucleic acids being a part of an expression vector that expression the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein encoding nucleic acids.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (See, e.g., Wu and Wu, 1987, *J. Biol. Chem.* 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (See, e.g., PCT Publications WO 92/06180; WO 92/22635; WO92/20316; WO93/14188; WO 93/20221). Alternatively, the nucleic acid can be introduced intracellularly and incorporated within host cell DNA for expression, by homologous recombination (Koller and Smithies, 1989, *Proc. Natl. Acad. Sci. USA* 86:8932-8935; and Zijlstra et al., 1989, *Nature* 342:435-438).

In a specific embodiment, viral vectors that contain nucleic acid sequences encoding an antibody or a fusion protein are used. For example, a retroviral vector can be used (See Miller et al., 1993, *Meth. Enzymol.* 217:581-599). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitates delivery of the nucleotide sequence into a subject. More detail about retroviral vectors can be found in Boesen et al., (1994, *Biotherapy* 6:291-302), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, *J. Clin. Invest.* 93:644-651; Klein et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (*Current Opinion in Genetics and Development* 3:499-503, 1993, present a review of adenovirus-based gene therapy. Bout et al., (*Human Gene Therapy*, 5:3-10, 1994) demonstrated the use of adenovirus vectors to transfer genes to the respiratory epithelia of rhesus monkeys. Other instances of the use of adenoviruses in gene therapy can be found in Rosenfeld et al., 1991, *Science* 252:431-434; Rosenfeld et al., 1992, *Cell* 68:143-155; Mastrangeli et al., 1993, *J. Clin. Invest.* 91:225-234; PCT Publication WO94/12649; and Wang et al., 1995, *Gene Therapy* 2:775-783. In a preferred embodiment, adenovirus vectors are used.

Adeno-associated virus (AAV) has also been proposed for use in gene therapy (see, e.g., Walsh et al., 1993, *Proc. Soc. Exp. Biol. Med.* 204:289-300 and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to, transfection, electroporation, microinjection, infection with a viral or bacteriophage vector, containing the nucleic acid sequences, cell fusion, chromosome-mediated gene transfer, microcellmediated gene transfer, spheroplast fusion, etc. Numerous techniques are known in the art for the introduction of foreign genes into cells (See, e.g., Loeffler and Behr, 1993, *Meth. Enzymol.* 217:599-618, Cohen et al., 1993, *Meth. Enzymol.* 217:618-644; and Clin. Pharma. Ther. 29:69-92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (See e.g., PCT Publication WO 94/08598; Stemple and Anderson, 1992, *Cell* 71:973-985; Rheinwald, 1980, *Meth. Cell Bio.* 21A:229; and Pittelkow and Scott, 1986, *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.4.3 Kits

The invention provides a pharmaceutical pack or kit comprising one or more containers filled with antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

5.5 Characterization and Demonstration of Therapeutic Utility

Several aspects of the pharmaceutical compositions or prophylactic or therapeutic agents of the invention are preferably tested in vitro, e.g., in a cell culture system, and then in vivo, e.g., in an animal model organism, such as a rodent animal model system, for the desired therapeutic activity prior to use in humans. For example, assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed, e.g., inhibition of or decrease in growth and/or colony formation in soft agar or tubular network formation in three-dimensional basement membrane or extracellular matrix preparation. The tissue sample can be obtained by biopsy from the patient. This test allows the identification of the therapeutically most effective prophylactic or therapeutic molecule(s) for each individual patient. Alternatively, instead of culturing cells from a patient, therapeutic agents and methods may be screened using cells of a tumor or malignant cell line. In various specific embodiments, in vitro assays can be carried out with representative cells of cell types involved in an autoimmune or inflammatory disorder (e.g., T cells), to determine if a pharmaceutical composition of the invention has a desired effect upon such cell types. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Preferred animal models for use in the methods of the invention are for example, transgenic mice expressing FcγR on mouse effector cells, e.g., any mouse model described in U.S. Pat. No. 5,877,396 (which is incorporated herein by reference in its entirety). Transgenic mice for use in the methods of the invention include but are not limited to mice carrying human FcγRIIIA, mice carrying human FcγRIIA, mice carrying human FcγRIIB and human FcγRIIIA, mice carrying human FcγRIIB and human FcγRIIA.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," *Inflammation*, 24(2): 141-155, (2000). Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol Med.* 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al., 1992, *Scand. J. Gastroentrol.* 27:529-537; Strober, 1985, *Dig. Dis. Sci.* 30(12 Suppl): 3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, *J. Exp. Med.* 1861737-1747).

Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed (Flanders et al., 1999, *Autoimmunity* 29:235-246; Krogh et al., 1999, *Biochimie* 81:511-515; Foster, 1999, *Semin. Nephrol.* 19:12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in *Relevance of Tumor Models for Anticancer Drug Development* (1999, eds. Fiebig and Burger); *Contributions to Oncology* (1999, eds. Karger); *The Nude Mouse in Oncology Research* (1991, eds. Boven and Winograd); and *Anticancer Drug Development Guide* (1997 ed. Teicher), herein incorporated by reference in their entireties.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3H$-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

5.6 Diagnostic Methods

Labeled antibodies of the invention can be used for diagnostic purposes to detect, diagnose, or monitor diseases, disorders or infections. The invention provides for the detection or diagnosis of a disease, disorder or infection, particularly an autoimmune disease comprising: (a) assaying the expression of FcγRIIB in cells or a tissue sample of a subject using one or more antibodies that immunospecifically bind to FcγRIIB; and (b) comparing the level of the antigen with a control level, e.g., levels in normal tissue samples, whereby an increase in the assayed level of antigen compared to the control level of the antigen is indicative of the disease, disorder or infection.

Antibodies of the invention can be used to assay FcγRIIB levels in a biological sample using classical immunohistological methods as described herein or as known to those of skill in the art (e.g., see Jalkanen et al., 1985, *J. Cell. Biol.* 101:976-985; Jalkanen et al., 1987, *J. Cell. Biol.* 105:3087-3096). Other antibody-based methods useful for detecting protein gene expression include immunoassays, such as the enzyme linked immunosorbent assay (ELISA) and the radio-immunoassay (RIA). Suitable antibody assay labels are known in the art and include enzyme labels, such as, alkaline phosphatase, glucose oxidase; radioisotopes, such as iodine ($^{125}$I, $^{131}$I), carbon ($^{14}$C), sulfur ($^{35}$S), tritium ($^{3}$H), indium ($^{121}$In), and technetium ($^{99m}$Tc); luminescent labels, such as luminol; and fluorescent labels, such as fluorescein and rhodamine.

One aspect of the invention is the detection and diagnosis of a disease, disorder, or infection in a human. In one embodiment, diagnosis comprises: a) administering (for example, parenterally, subcutaneously, or intraperitoneally) to a subject an effective amount of a labeled antibody that immunospecifically binds to FcγRIIB; b) waiting for a time interval following the administration for permitting the labeled antibody to preferentially concentrate at sites in the subject where FcγRIIB is expressed (and for unbound labeled molecule to be cleared to background level); c) determining background level; and d) detecting the labeled antibody in the subject, such that detection of labeled antibody above the background level indicates that the subject has the disease, disorder, or infection. In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

6. EXAMPLES 6.1 Preparation of Monoclonal Antibodies

A mouse monoclonal antibody was produced from clones 3H7 or 2B6 with ATCC accession numbers PTA-4591 and PTA-4592, respectively. A mouse monoclonal antibody that specifically binds FcγRIIB with greater affinity than said monoclonal antibody binds FcγRIIA, was generated. Transgenic FcγRIIA mice (generated in Dr. Ravetch Laboratory, Rockefeller University) were immunized with FcγRIIB purified from supernatant of 293 cells that had been transfected with cDNA encoding the extracellular domain of the human FcγRIIB receptor, residues 1-180. Hybridoma cell lines from spleen cells of these mice were produced and screened for antibodies that specifically bind FcγRIIB with greater affinity than the antibodies bind FcγRIIA.

6.2 Antibody Screening and Characterization
Materials and Methods

Supernatants from hybridoma cultures are screened for immunoreactivity against FcγRIIA or FcγRIIB using ELISA assays. In each case, the plate is coated with 100 ng/well of FcγRIIA or FcγRIIB. The binding of the antibody to the specific receptor is detected with goat anti-mouse HRP conjugated antibody by monitoring the absorbance at 650 nm.

In the blocking ELISA experiment, the ability of the antibody from the hybridoma supernatant to block binding of aggregated IgG to FcγRIIB is monitored. The plate is blocked with the appropriate "blocking agent", washed three times (200 µl/well) with wash buffer (PBS plus 0.1% Tween). The plate is pre-incubated with hybridoma supernatant for 1 hour at 37° C. Subsequent to blocking, a fixed amount of aggregated biotinylated human IgG (1 µg/well) is added to the wells to allow the aggregate to bind to the FcγRIIB receptor. This reaction is carried out for two hours at 37° C. Detection is then monitored, after additional washing, with streptavidin horseradish peroxidase conjugate, which detects the bound aggregated IgG. The absorbance at 650 nm is proportional to the bound aggregated IgG.

In a β-hexoaminidase release assay the ability of an antibody from the hybridoma supernatant to inhibit Fcε-induced release of β-hexoaminidase is monitored. RBL-2H3 cells are transfected with human FcγRIIB; cells are stimulated with various concentration of goat anti-mouse F(ab)$_2$ fragment ranging from 0.03 µg/mL to 30 µg/mL; sensitized with either mouse IgE alone (at 0.01 µg/mL) or with an anti-FcγRIIB antibody. After 1 hour incubation at 37° temperature, the cells are spun down; the supernatant is collected; and the cells are lysed. The β-hexoaminidase activity released in the supernatant is determined in a colorometric assay using p-nitrophenyl N-acetyl-β D-glucoasminide. The release β-hexoaminidase activity is expressed as a percentage of the released activity relative to the total activity.

FACS Analysis

CHO cells, expressing FcγRIIB are stained with various antibodies and analyzed by FACS. In one series of experiment, the cells are directly labeled to determine if the monoclonal antibodies recognize the receptor.

In the blocking FACS experiment, the ability of the antibody from the hybridoma supernatant to block the binding of aggregated IgG to FcγRIIB is monitored. About 1 million cells (CHO cells expressing FcγRIIB) for each sample are incubated on ice for 30 minutes with 2 µg of the isotype control (mouse IgG1) or with the 2B6 or 3H7 antibody. Cells are washed once with PBS+1% BSA and incubated with 1 µg of aggregated biotinylated human IgG for 30 minutes on ice. Cells are washed and the secondary antibodies are added, goat anti-mouse-FITC to detect the bound antibody and Streptavidin-PE conjugated to detect the bound aggregated biotinylated human IgG and incubated on ice for 30 minutes. Cells are washed and analyzed by FACS.

B Lymphocytes are stained to detect the presence of FcγRIIB and CD20. 200 µl of "buffy coat" for each sample is incubated on ice with 2 µg of isotype control or the monoclonal antibodies, 2B6 or 3H7. Cells are washed once with PBS+1% BSA and incubated with 1 µl of goat anti mouse-PE antibody for 30 minutes on ice. Cells are washed once and CD20-FITC antibody (2 µg) is added to the samples and incubated on ice for 30 minutes. All samples are washed with PBS+1% BSA once and the cells are analyzed by FACS.

Human PBMCs were stained with 2B6, 3H7, and IV.3 antibodies, followed by a goat anti-mouse-Cyanine (Cy5) conjugated antibody (two color staining using anti-CD20-FITC conjugated for B lymphocytes, anti-CD14-PE conjugated for monocytes, anti-CD56-PE conjugated for NK cells and anti-CD16-PE conjugated for granulocytes.

ADCC ASSAY $4-5 \times 10^6$ target cells expressing Her2/neu antigen (IGROV-1 or SKBR-3 cells) are labeled with bis(acetoxymethyl) 2,2':6',2''-terpyridine-t-6''-dicarboxylate (DELFIA BATDA Reagent, Perkin Elmer/Wallac). BATDA reagent is added to the cells and the mixture is incubated at 37° C. preferably under 5% $CO_2$, for at least 30 minutes. The cells are then washed with a physiological buffer, e.g., PBS with 0.125 mM sulfinpyrazole, and media containing 0.125 mM sulfinpyrazole. The labeled target cells are added to effector cells, e.g., PBMC, to produce effector:target ratios of approximately 50:1, 75:1, or 100:1. PBMC is isolated by layering whole blood onto Ficoll-Hypaque (Sigma) and spinning at room temperature for 30 mins at 500 g. The leukocyte layer is harvested as effectors for Europium-based ADCC assays. Frozen or freshly isolated elutriated monocytes (Advanced Biolechnologies, MD) is used as effectors with the tumor target cell lines at varying effector to target ratio of 1100:1 to 10:1 and the concentration of the antibodies is titrated from 1-15 g/ml. Monocytes obtained as frozen stocks stimulated with cytokines is used as effector cells in ADCC assays. If frozen monocytes perform optimally they will be routinely used otherwise fresh cells will be used. MDM will be prepared by treatment with cytokines GM-CSF or M-CSF that are known to enhance the viability and differentiation of monocytes in culture. MDM will be stimulated with cytokines and the expression of the various FcγRs (I, IIA, IIB, and IIIA) determined by FACS analysis.

The effector and target cells are incubated for at least two hours, and up to 16 hours, at 37° C., under 5% $CO_2$ in the presence of an anti-tumor antibody, specific for an antigen expressed on the target cells, Her2/neu, and in the presence or absence of an anti-FcγRIIB antibody. A chimeric 4D5 antibody that has been engineered to contain the N297A mutation which is used as a negative control since this antibody binds the tumor target cells via its variable region. Loss of glycosylation at this site abolishes binding of the Fc region of the antibody to FcγR. Commercially available human IgG1/k serves as an isotype control for the anti-FcγIIB antibody. Cell supernatants are harvested and added to an acidic europium solution (e.g., DELFIA Europium Solution, Perkin Elmer/Wallac). The fluorescence of the Europium-TDA chelates formed is quantitated in a time-resolved fluorometer (e.g., Victor 1420, Perkin Elmer/Wallac). Maximal release (MR) and spontaneous release (SR) are determined by incubation of target cells with 1% TX-100 and media alone, respectively. Antibody independent cellular cytotoxicity (AICC) is measured by incubation of target and effector cells in the absence of antibody. Each assay is preferably performed in triplicate. The mean percentage specific lysis is calculated as: Experimental release (ADCC)–AICC)/(MR–SR)×100.

Characterization of the Monoclonal Antibody Produced from THE 3H7 CLONE

The Direct Binding of Different Batches of Hybridoma Cultures

Figure 1B:
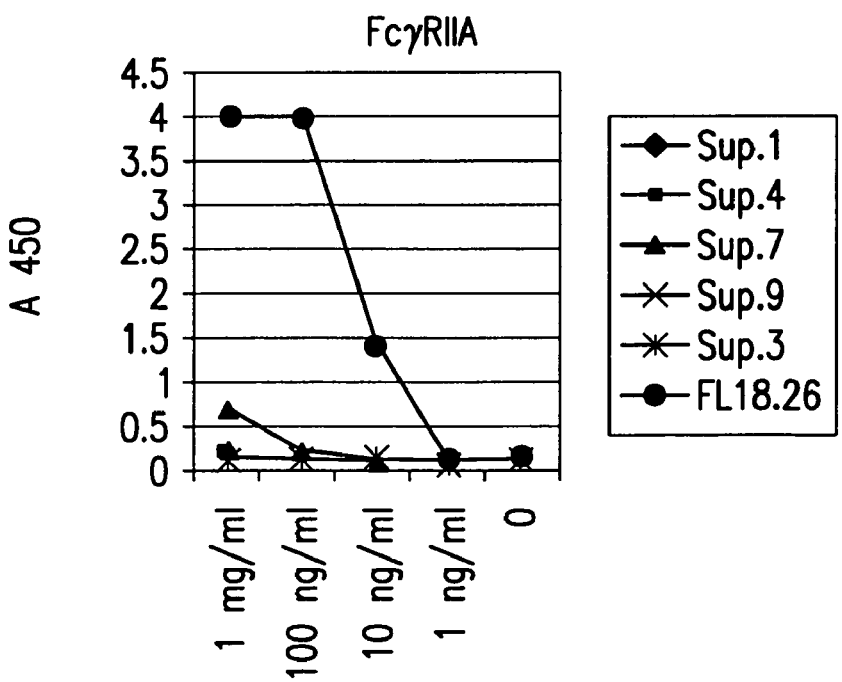

The direct binding of different batches of hybridoma cultures to FcγRIIA and FcγRIIB were compared using an ELISA assay (FIG. 1A). Supernatants numbered 1, 2, 7, 9, and 3 were tested for specific binding and their binding was compared to a-commercially available antibody, FL18.26. As shown in FIG. 1A, supernatant from clone 7 has the maximal binding to FcγRIIB, which is about four times higher under saturating conditions than the binding of the commercially available antibody to FcγRIIB. However, the supernatant from clone 7 has hardly any affinity for FcγRIIA, as seen in FIG. 1B, whereas the commercially available antibody binds FcγRIIA at least 4 times better.

Figure 1C:
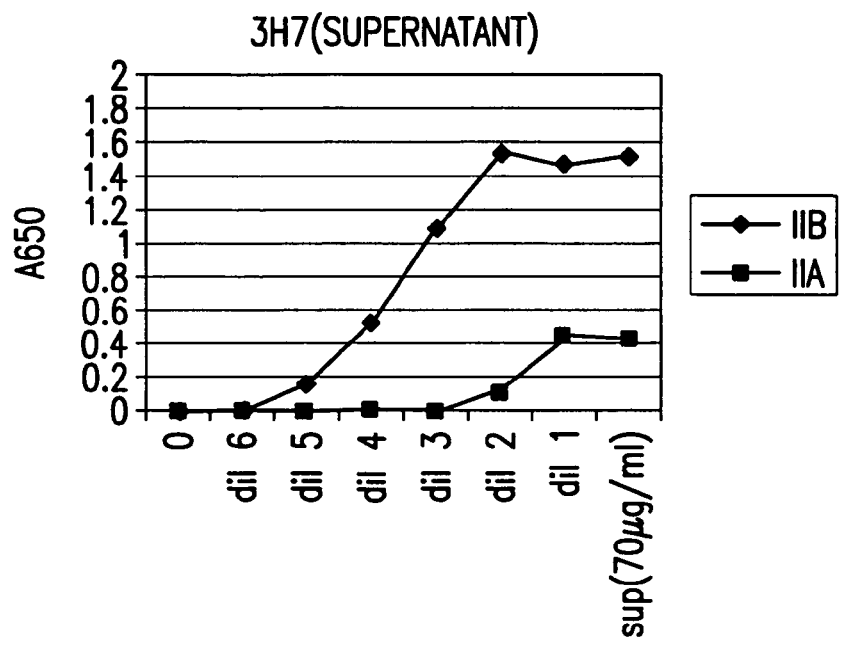
Figure 1D:
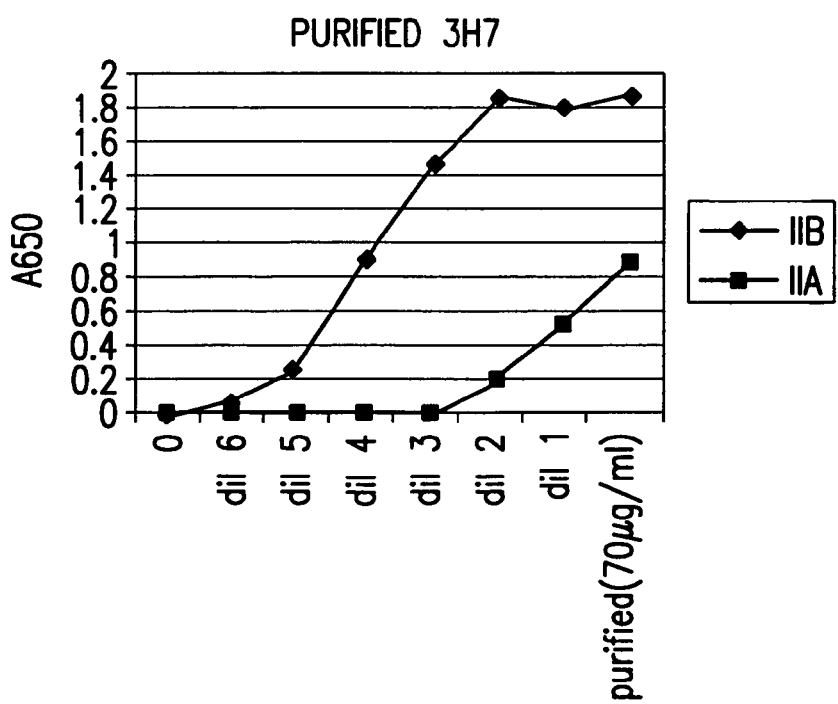

Direct Binding of the Antibody Produced from the 3H7 Clone to FcγRIIA and FcγRIIB The binding of crude 3H7 supernatant (FIG. 1C) and purified 3H7 supernatant was measured (FIG. 1D). In each case, the supernatant was supplied as a concentration of 70 µand diluted up to 7-fold. As shown in FIG. 1C, upon saturating conditions, the 3F7 supernatant binds FcγRIIB four times better than it binds FcγRIIA. Upon purification with an protein G column, the absolute binding of the 3H7 supernatant to each immunogen improves.

Blocking of Aggregated Human IgG Binding to FcγRIIB by the Antibody Produced from the 3H7 Clone.

If the antibody present in the hybridoma supernatant binds FcγRIIB at the IgG binding site and blocks IgG binding, then the aggregated IgG cannot bind the receptor and hence no absorbance at 650 can be detected. The antibody in effect is a "blocking agent" that blocks the IgG binding site on FcγRIIB. As a control, the ELISA was carried out with no blocking, with a control supernatant, and with supernatant from the 3H7 clone. As shown in FIG. 2, the 3H7 supernatant completely blocks IgG binding, since aggregated IgG cannot bind the receptor as evident from the lack of absorbance at 650 nm. The control supernatant however fails to block IgG binding; aggregated IgG binds the receptor as evident by the reading at 650 nm. The control supernatant behaves similarly to the condition where no blocking was done.

Comparison of the Direct Binding of the Antibody Produced from the 3H7 Clone to Bacterial and Mammalian FcγRIIB As shown in FIG. 3, the supernatant from the 3H7 clone, binds comparably to mammalian and bacterial FcγRIIB. Upon saturating conditions, the 3H7 supernatant binds bacterial and mammalian FcγRIIB about three times better than it binds FcγRIIA. The monoclonal antibody from the 3H7 clone is thus able to specifically bind to mammalian FcγRIIB which has been post-transnationally modified (e.g., glycosylation).

Direct Binding of the Antibody Produced from the 3H7 Clone to FcγRIIA, FcγRIIB, and FcγRIIIA The direct binding of supernatant from the hybridoma cultures from the 3H7 cell line to FcγRIIA, FcγRIIIA and FcγRIIB were compared using an ELISA assay (FIG. 4).

The antibody produce from clone 3H7 has no affinity for FcγRIIIA, and binds FcγRIIB with about 4 times greater affinity than it binds FcγRIIA.

Characterization of the Monoclonal Antibody Produced from the 2B6 Clone

Comparison of Direct Binding of the Antibody Produced from Clone 2B6 Compared to other Three Commercially Available Monoclonal Antibodies Against FcγRII The binding of the antibody produced from clone 2B6 to FcγRIIA and FcγRIIB is compared to that of three other commercially available antibodies, AT10, FL18.26, and IV.3, against FcγRII in an ELISA assay. As seen in FIG. 5A, the antibody produced from clone 2B6 binds FcγRIIB up to 4.5 times better than the other commercially available antibodies. Additionally, the antibody produced from clone 2B6 has minimal affinity for FcγRIIA, whereas the other three commercially available antibodies bind FcγRIIA in a saturable manner and twice as much as the antibody from clone 2B6 binds FcγRIIA (FIG. 5B.

Blocking of Aggregated Human IgG to FcγRIIB by the Antibody Produced from Clone 2B6.

The ability of the antibody produced from clone 2B6 to block binding of the aggregated IgG to FcγRIIB was investigated by a blocking ELISA assay and compared to that of the antibody produced by clone 3H7. As shown in FIG. 6A, the control supernatant does not bind FcγRIIB on the IgG binding site and the aggregated IgG can bind the receptor and hence absorbance at 650 nm is maximal. Clone 3H7, however, blocks the IgG binding up to 75%. Clone 2B6 completely blocks the binding of the IgG binding site and does not allow the aggregated IgG to bind the receptor, and even at very high dilutions no absorbance is detected at 650 nm. FIG. 6B represents the data in a bar diagram.

Competition of 2B6 Antibody and Aggregated IgG in Binding FcγRIIB Using Double-Staining FACS Assays A double staining FACS assay was used to characterize the antibody produced from clone 2B6 in CHO cells that had been transfected with full-length mammalian FcγRIIB.

As shown in FIG. 7C, the antibody produced from clone 2B6 effectively blocks the binding of aggregated IgG to the FcγRIIB receptor in CHO cells since no staining is observed for biotinylated aggregated IgG after the cells were pre-incubated with the monoclonal antibody. The cells are only stained in the lower right panel, indicating that most of the cells were bound to the monoclonal antibody from the 2B6 clone. In the control experiments, using IgG1 as the isotype control, FIG. 7A, when the cells are stained with the isotype labeled IgG, no staining is observed since the monomeric IgG does not bind FcγRIIB with any detectable affinity, whereas in FIG. 7B, about 60% of the cells are stained with aggregated IgG, which is capable of binding FcγRIIB.

Monoclonal Anti-FcγRIIB Antibodies and CD20 Co-Stain Human B Lymphocytes

A double staining FACS assay was used to characterize the antibody produced from clones 2B6 and 3H7 in human B lymphocytes. Cells were stained with anti-CD20 antibody which was FITC conjugated, to selected the B-lymphocyte population, as well as the antibodies produced from clone 3H7 and 2B6, labeled with goat anti-mouse peroxidase. The horizontal axis represents the intensity of the anti-CD20 antibody fluorescence and the vertical axis represents the intensity of the monoclonal antibody fluorescence. As shown in FIGS. 8B and 8C, cells are double stained with the anti-CD20 antibody as well as the antibodies produced from clone 2B6 and 3H7, however, the antibody produced from clone 2B6 shows more intense staining than that produced from clone 3H7. FIG. 8A shows the staining of the isotype control, mouse IgG1.

Staining of CHO Cells Expressing FcγRIIB

CHO cells, stably expressing FcγRIIB were stained with IgG1 isotype control (FIGS. 9A and B) or with supernatant from the 3H7 hybridoma (FIGS. 9C and D). Goat anti-mouse peroxidase conjugated antibody was used as a secondary antibody. The cells were then analyzed by FACS: cells that are stained with the supernatant from the 3H7 hybridoma show a strong fluorescence signal and a peak shift to the right; indicating the detection of FcγRIIB in the CHO cells by the supernatant produced from the 3H7 hybridoma. Cells stained with the supernatant from the 2B6 hybridoma, also show a significant fluorescence, as compared to cells stained with IgG1, and a peak shift to the right, indicating the detection of FcγRIIB in the CHO cells by supernatant produced from the 2B6 hybridoma.

CHO cells expressing huFcγRIIB were incubated with the anti CD32B antibodies, 2B6 or 3H7. Cells were washed and 9 μg/ml of aggregated human IgG were added to the cells on ice. The human aggregated IgG were detected with goat anti human-IgG GITC conjugated. Samples were analyzed by FACS cells labeled with 2B6 or 3H7 showed a significant fluorescence peak in the presence of aggregated human IgG (FIGS. 10A and 10B). 2BG antibody completely blocks binding of aggregated IgG as evidenced by the fluorescent peak shift to the left. Whereas the 3H7 antibody partially blocks binding of aggregated IgG as shown by the intermediate fluorescent peak. The other antibodies, 1D5 (FIG. 10E), 1F2 (FIG. 10G), 2E1 (FIG. 10C), 2H9 (FIG. 10D), and 2D11 (FIG. 10F) do not block binding of aggregated IgG. The amount of each antibody bound to the receptor on the cells was also detected (inset) on a separate set of samples using a goat anti-mouse PE conjugated antibody.

FACS Profiles Using 2B6, 3H7, and IV-3 Antibodies on Human Peripheral Blood Leukocyte.

The FACS profile of the anti-FcγRIIB antibodies and IV.3 antibody shows their ability to discriminate between the two FcγRII isoforms, IIB and IIA expressed on the human hematopoietic cells. IV.3, one of the first antibodies (commercially available) used to define FcγRII, shows preferential binding to FcγRIIA.

Figure 11B:
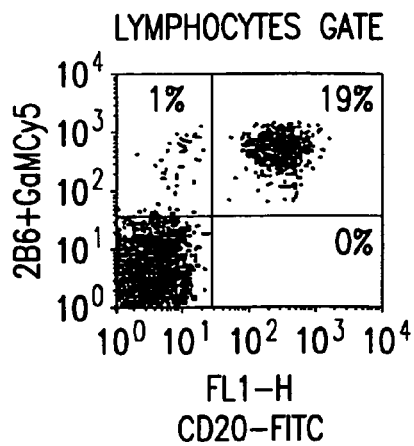
Figure 11C:
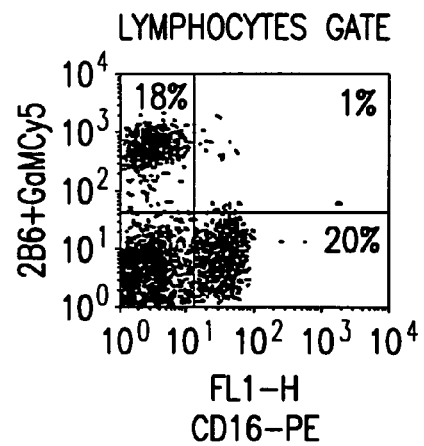
Figure 11D:
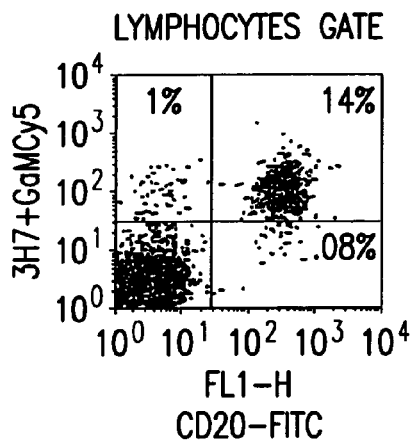
Figure 11E:
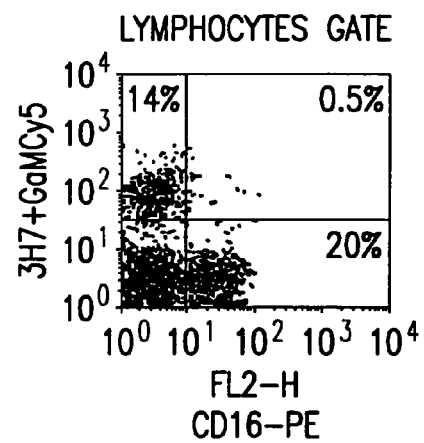
Figure 11F:
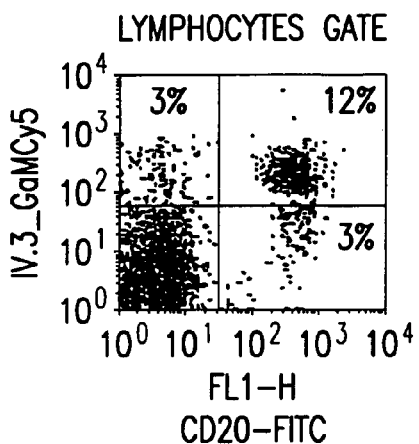
Figure 11G:
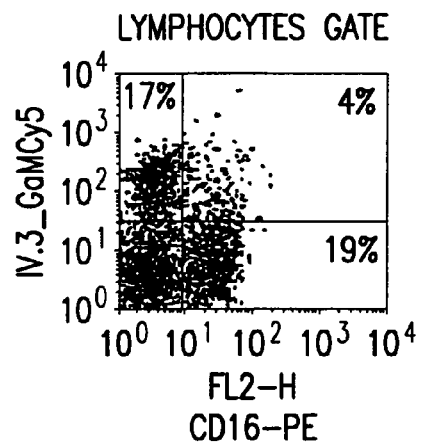
Figure 11H:
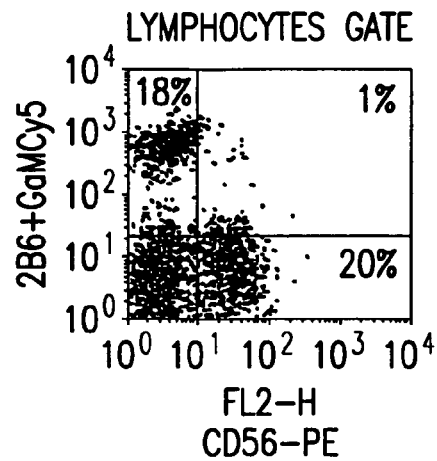
Figure 11I:
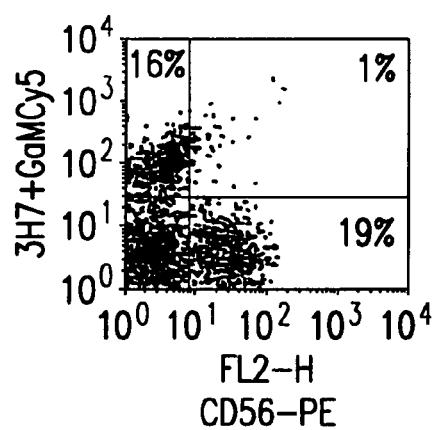
Figure 11J:
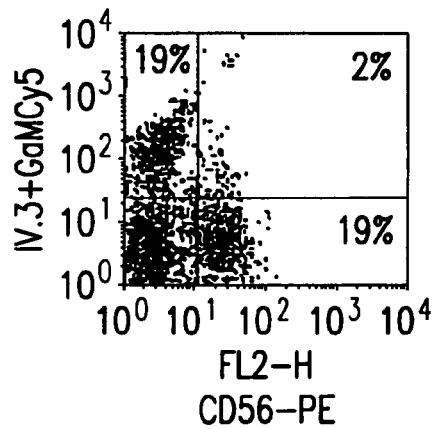
Figure 11K:
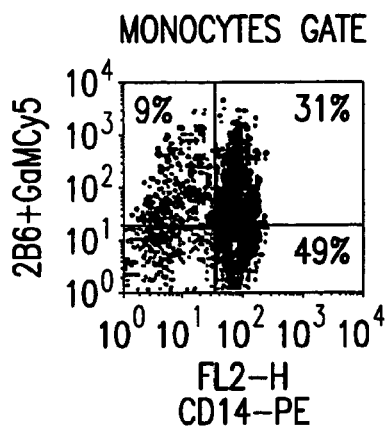
Figure 11L:
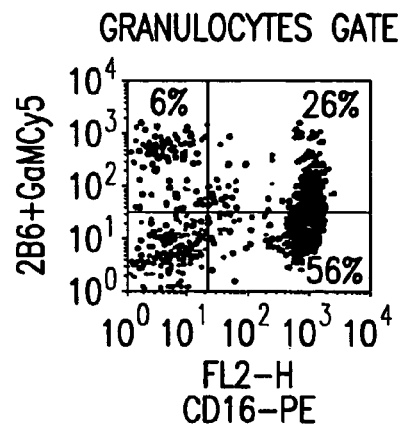
Figure 11M:
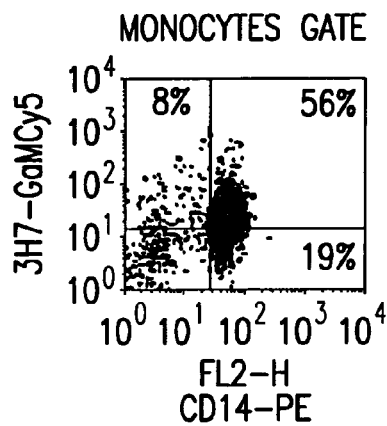
Figure 11N:
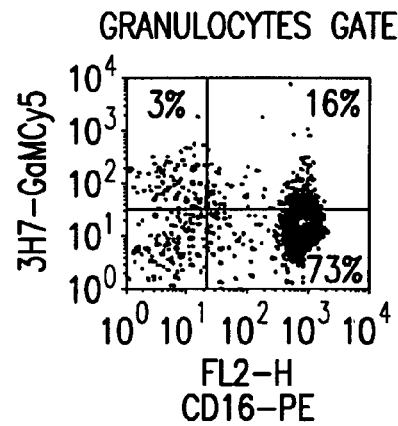
Figure 11O:
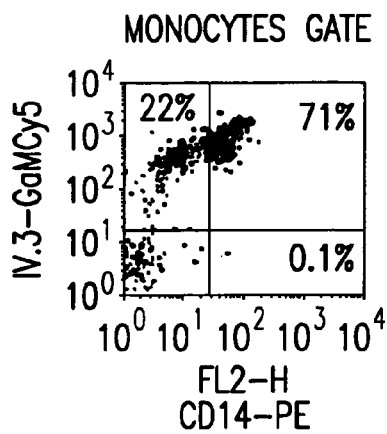
Figure 11P:
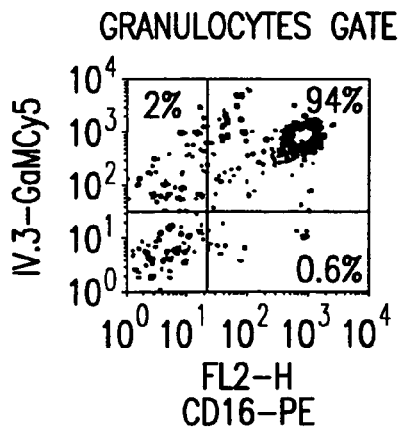

There are characteristic and functionally significant differences in isoform expression between major human hematopoietic cell types. Human B lymphocytes express exclusively the huFcγRIIB isoform while human monocytes express predominantly the huFcγRIIA isoform. Granulocytes are strongly positive for FcγRIIA and limited evidence suggest that FcγRIIB is marginally expressed in this population (Pricop et al., 2000, *J. Immunol.* 166:531-537). To further characterize the reactivity of the anti-FcγRIIB antibodies, huPBL were stained with the anti-FcγRIIB antibodies 2B6 and 3H7 and with IV.3, which preferentially (but not exclusively) recognizes the FcγRIIA isoform of the receptor, leukocytes populations were selected based on FSC vs. SSC gating (FIG. 11) and identified with specific markers: CD20 (B cells; FIGS. 11B, 11D and 11F), CD56 (FIG. 11H-11J) or CD16 (NK cells, lymphocyte gate; FIGS. 11C, 11E and 11G). CD14 (monocytes; FIGS. 11K, 11M and 11O) and CD16 (granulocytes, granulocyte gate; FIGS. 11L, 11N AND 11P). CD20-positive cells (B cells) were uniformly stained with 2B6, 3H7 (FIGS. 11B, 11D). IV.3 also stained the majority of CD20-positive cells (FIG. 11F). No staining was observed for CD16/CD56-positive NK cells, while only a fraction of CD14-(monocytes) and CD16-(granulocytes) positive cells were stained with 2B6, 3H7 (FIGS. 11L, 11N). In contrast, IV.3 strongly stained the vast majority of CD-14-positive monocytes (FIG. 11O) and the totality of CD16-positive granulocytes (FIGS. 11P). This differential pattern of reactivity between 2B6 and 3H7 on the one side and IV.3 on the other indicates that the new monoclonal antibodies react strongly with FcγRIIB, but not with FCγRIIA, while IV.3 cannot discriminate between FcγRIIA and FcγRIIB isoforms in vivo.

Inhibition of B-hexosaminidase Release by 2B6

Transfectants expressing human FcγRIIB were sensitized with mouse IgE and challenged with F(ab')$_2$ fragments of a polyclonal goat anti-mouse IgG to aggregate FcεRI. Crosslinking occurs because of the ability of the polyclonal antibody to recognize the light chain of the murine IgE antibody bound to FcεRI. This experiment id schematically shown in FIG. 12B. Transfectant sensitized with murine IgE and preincubated with 2B6 antibody were also challenged with F(ab')$_2$ fragments of a polyclonal goat anti-mouse IgG to cross link FcεRI to FcγRIIB. As shown in FIG. 12A, β-hexoaminidase release of a lower magnitude was observed when cells which were pre-incubated with 2B6 antibody and IgE were challenged with goat anti mouse F(ab')$_2$. As seen in FIG. 12B, 2B6 antibody does not block the inhibitory receptor activity, rather cross-linking with FcεRI activates the inhibitory pathway and results in a significant decrease in β-hexosaminidase release. These date also show that human FcγRIIB inhibitory receptor can effectively signal in rat basophils.

In Vitro Adcc Assays

In order to determine whether IGROV-1, OVAR-8, and SKBR-3 cells express the Her2neu antigen, cells were stained with either purified 4D5 or ch4D5 antibody on ice; the unbound antibody was washed out with PBS/BSA buffer containing sodium azide, and the binding of 4D5 or ch4D5 was detected by goat anti-mouse or goat anti-human antibody conjugated to PE (Jackson Laboratories), respectively. An irrelevant IgG1 antibody (Becton Dickinson) served as a control for non-specific binding. As shown in FIGS. 13A-C, the ovarian tumor cells lines express less Her2/neu antigens than the breast carcinoma cell line and evaluating these cell lines in parallel will determine the stringency of tumor clearance by an anti-FcγRIIB antibody of the invention.

Human monocytes are the effector population involved in ADCC that express both activating and inhibitory receptors. The expression of FcγRs was tested by FACS analysis using several lots of frozen monocytes as these cells will be adoptively transferred as effectors to investigate the role of ch2B6 in tumor clearance. Commercially obtained frozen elutriated monocytes were thawed in basal medium containing 10% human AB serum and in basal medium with human serum and 25-50 ng/ml GM-CSF. Cells were either stained directly or allowed to mature to macrophages for 7-8 days (MDM), lifted off the plastic, and then stained with IV.3-FITC (anti-hu FcγRIIA), 32.2-FITC (anti-FcγRI), CD16-PE (Pharmingen) or 3G8 (anti-FcγRIII)-goat anti-mouse-PE, 3H7 (anti-FcγRIIB), and CD14 marker for monocytes (Pharmingen), along with relevant isotype controls. A representative FACS profile of MDM from two donors, depicting FcγR expression on freshly thawed monocytes (FIGS. 14Q-T) and cultured monocytes (FIGS. 14A-P), is shown in FIG. 14. These results indicate that FcγRIIB is modestly expressed in monocytes (5-30% depending on donor). However this expression increases as they mature into macrophages. Preliminary data show that tumor-infiltrating macrophages in human tumor specimens are positively stained for FcγRIIB (data not shown). The pattern of FcγRs and the ability to morphologically differentiate into macrophages was found to be reproducible in several lots of frozen monocytes. These data indicate that this source of cells is adequate for adoptive transfer experiments.

Ch4D5 Mediates Effective ADCC with Ovarian and Breast Cancer Cells Lines using PBMC The ADCC activity of anti-Her2/neu antibody was tested in a europium based assay. The ovarian cell line, IGROV-1 (FIG. 15A), and the breast cancer cell line, SKBR-3 (FIG. 15B), were used as labeled targets in a 4 h assay with human PBL as effector cells. FIGS. 15A and B indicates that ch4D5 is functionally active in mediating lysis of targets expressing Her2neu. The effect of an antibody of the invention on the ADCC activity of the anti-Her2/neu antibody is subsequently measured.

In Vivo Activity of FcγRIIB Antibodies in Xenograft Murine Models Using Human Tumor Cell Lines Six to eight week old female Balb/c nude mice (Jackson Laboratories, Bar Harbor, Me.; Taconic) is utilized for establishing the xenograft ovarian and breast carcinoma models. Mice are maintained at BIOCON, Inc. Rockville, Md. (see attached protocol). Mice are housed in Biosafety Level-2 facilities for the xenograft model using the ascites-derived ovarian cells and pleural effusion-derived breast cancer cells as sources of tumors. Mice are placed in groups of 4 for these experiments and monitored three times weekly. The weight of the mice and survival time are recorded and criteria for growing tumors is abdominal distention and palpable tumors. Mice showing signs of visible discomfort or that reach 5 grams in tumor weight are euthanized with carbon dioxide and autopsied. The antibody-treated animals are placed under observation for an additional two months after the control group.

Establishment of the Xenograft Tumor Model with Tumor Cell Lines

In order to establish the xenograft tumor model, $5 \times 10^6$ viable IGROV-1 or SKBR-3 cells are injected s.c into three age and weight matched female nude athymic mice with Matrigel (Becton Dickinson). The estimated weight of the tumor is calculated by the formula: length×(width)$^2$/2 not to exceed 3 grams. For in vivo passaging of cells for expansion, anchorage-dependent tumor is isolated and the cells dissociated by adding 1 µg of collagenase (Sigma) per gram of tumor at 37 C overnight.

Injection of IGROV-1 cells s.c gives rise to fast growing tumors while the i.p route induces a peritoneal carcinomatosis which kills the mice in 2 months. Since the IGROV-1 cells form tumors within 5 weeks, at day 1 after tumor cell injection, monocytes as effectors are co-injected i.p along with therapeutic antibodies ch4D5 and ch2B6 at 4 μg each per gm of mouse body weight (mbw) (Table 6). The initial injection is followed by weekly injections of antibodies for 4-6 weeks thereafter. Human effectors cells are replenished once in two weeks. A group of mice will receive no therapeutic antibody but will be injected with ch4D5 N297A and human IgG1 as isotype control antibodies for the anti-tumor and ch2B6 antibody, respectively.

TABLE 6

Outline for tumor clearance studies with anti-Her2neu antibody, ch4D5 and ch2B6, anti-FcγRIIB antibody in xenograft tumor model in nude mice with adoptively transferred human monocytes as ADCC effectors. MWB (mouse body weight).

| 8 mice/group | Tumor cell s.c day 0 | Monocytes i.p at day 1 | ch4D5 4 μg/gm of mbw day 1 i.p | ch4D5 N297A at 4 μg/gm of mbw day 1 i.p | ch2B6 N297A at 4 μg/gm of mbw day 1 i.p | Human IgG1 4 μg/gm of mbw day 1 i.p |
|---|---|---|---|---|---|---|
| A | + | − | − | − | − | − |
| B | + | + | − | − | − | − |
| C | + | + | + | − | − | − |
| D | + | + | + | − | + | − |
| E | + | + | − | − | + | − |
| F | + | + | − | + | − | + |

As shown in Table 6, 6 groups of 8 mice each are required for testing the role of an anti-FcγRIIB antibody in tumor clearance with one target and effector combination, with two different combinations of the antibody concentrations. These groups are A) tumor cells, B) tumor cells and monocytes, C) tumor cells, monocytes, anti-tumor antibody, ch4D5, D) tumor cells, monocytes, anti-tumor antibody ch4D5, and an anti-FcγRIIB antibody, e.g., ch2B6, E) tumor cells, monocytes, and an anti-FcγRIIB antibody, e.g., ch2B6, and F) tumor cells, monocytes, ch4D5 N297A, and human IgG1. Various combination of antibody concentration can be tested in similar schemes.

Studies using the breast cancer cell line, SKBR-3, are carried out in parallel with the IGROV-1 model as SKBR-3 cells over-express Her2neu. This will increase the stringency of the evaluation of the role of anti-FcγRIIB antibody in tumor clearance. Based on the outcome of the tumor clearance studies with the IGROV-1 cells, modifications are made to experimental design of future experiments with other targets.

The endpoint of the xenograft tumor model is determined based on the size of the tumors (weight of mice), survival time, and histology report for each group in Table xx. Mice are monitored three times a week; criteria for growing tumors are abdominal distention and presence of palpable masses in the peritoneal cavity. Estimates of tumor weight versus days after inoculation is calculated. Based on these three criteria from group D mice in Table xx versus the other groups of mice will define the role of anti-FcγRIIB antibodies in enhancement of tumor clearance. Mice that show signs of visible pain or reach 5 grams of tumor weight are euthanized with carbon dioxide and autopsied. The antibody-treated animals are followed for two months after this time-point.

In Vivo Activity Of FcγRIIB Antibodies in Xenograft Murine Model with Human Primary Ovarian and Breast Carcinoma Derived Cells Primary tumors are established from primary ovarian and breast cancers by transferring tumors cells isolated from exudates from patients with carcinomatosis. In order to translate these studies into the clinic, the xenograft model are evaluated with ascites- and pleural effusion-derived tumor cells from two ovarian and two breast carcinoma patients, respectively. Pleural effusion, as a source of breast cancer cells, and implantation of malignant breast tissue have been used to establish xenograft murine models successfully, see, e.g., Sakakibara et al., 1996, *Cancer J. Sci. Am.* 2: 291, which is incorporated herein by reference in its entirety. These studies will determine the broad range application of the anti-FcγRIIB antibody in tumor clearance of primary cells. Tumor clearance is tested using anti-tumor antibody, ch4D5 and anti-FcγRIIB antibody, e.g., ch2B6, in Balb/c nude mouse model with adoptively transferred human monocytes Human Ascites and Pleural Effusion-Derived Primary Tumor Cells Ascites from patients with ovarian cancer and pleural effusions from breast cancer patients are provided by the St. Agnes Cancer Center, Baltimore, Md. The ascites and pleural effusion from patients may contain 40-50% tumor cells and samples with a high expression of Her2neu+ tumor cells will be used to establish the xenograft models.

Ascites and pleural effusion samples are tested for expression of Her2/neu on neoplastic cells prior to establishment of the xenograft tumor model. The percentage of the neoplastic cells versus other cellular subsets that may influence the establishment of the tumor model will be determined. Ascites and pleural effusion from patients with ovarian and breast cancer, respectively are routinely analyzed to determine the level of expression of Her2/neu+ on the neoplastic cells. FACS analysis is used to determine the percentage of Her2/neu+ neoplastic cells in the clinical samples. Samples with high percentage of Her2/neu+ neoplastic cells are selected for initiation of tumors in Balb/c mice.

Histochemistry and Immunochemistry

Histochemistry and immunohistochemistry is performed on ascites and pleural effusion of patients with ovarian carcinoma to analyze structural characteristics of the neoplasia. The markers that are monitored are cytokeratin (to identify ovarian neoplastic and mesothelial cells from inflammatory and mesenchymal cells); calretinin (to separate mesothelial from Her2/neu positive neoplastic cells); and CD45 (to separate inflammatory cells from the rest of the cell population in the samples). Additional markers that will be followed will include CD3 (T cells), $CD_{20}$ (B cells), CD56 (NK cells), and CD14 (monocytes).

For immunohistochemistry staining, frozen sections and paraffinized tissues are prepared by standard techniques. The frozen as well as the de-paraffinized sections are stained in a similar staining protocol. The endogenous peroxidase of the tissues is quenched by immersing the slides in 3% hydrogen peroxide and washed with PBS for 5 minutes. Sections are blocked and the primary antibody ch4D5 is added in blocking serum for 30 minutes followed by washing the samples with PBS three times. The secondary anti-human antibody conjugated with biotin is added for 30 minutes and the slides are washed in PBS for 5 minutes. Avidin-Biotin peroxidase complex (Vector Labs) is added for 30 minutes followed by washing. The color is developed by incubating the slides in fresh substrate DAB solution and the reaction is stopped by washing in tap water. For H& E staining, the slides are deparaffinized and then hydrated in different alcohol concentrations. The slides are washed in tap water and placed in hematoxylin for 5 minutes. Excess stain is removed with acid-alcohol, followed by ammonia, and water. The slides are placed in Eosin and followed by 90 to 100% alcohol washes for dehydration. Finally, the slides are placed in xylene and mounted with fixative for long-term storage. In all cases, the percentage of tumor cells is determined by Papanicolaou stain.

Histochemical Staining

Ascites from two different patients with ovarian carcinoma were stained by Hematoxylin and Eosin (H & E) and Giemsa to analyze the presence of tumor cells and other cellular types. The results of the histochemical staining is shown in FIG. 16.

Murine Models

Samples from ovarian carcinoma patients is processed by spinning down the ascites at 6370 g for 20 minutes at 4 C, lysing the red blood cells followed by washing the cells with PBS. Based on the percentage of Her2neu+ tumor cells in each sample, two samples, a median and high expresser are selected for s.c inoculation to establish the xenograft model to evaluate the role of anti-FcγRIIB antibody, in clearance of tumors. It has been reported that tumor cells make up 40-50% of the cellular subset of unprocessed ascites, and after purification ~10–50×10$^6$ tumor cells were obtained from 2 liters of ascites (Barker et al., 2001, *Gynecol. Oncol.* 82: 57-63). The isolated ascites cells are injected i.p into mice to expand the cells. Approximately 10 mice will be injected i. p and each mouse ascites further passaged into two mice each to obtain ascites from a total of 20 mice, which is used to inject a group of 80 mice. Pleural effusion is handled in a manner similar to ascites and Her2neu+tumor cells are injected into the upper right and left mammary pads in matrigel. After s.c inoculation of tumor cells, mice are followed for clinical and anatomical changes. As needed, mice may be necropsied to correlate total tumor burden with specific organ localization.

What is claimed is:

1. A mouse monoclonal antibody produced by a clone selected from the group consisting of clone 1D5 having ATCC accession no. PTA-5958, clone 2E1 having ATCC accession no. PTA-5961, clone 2H9 having ATCC accession no. PTA-5962, clone 2D11 having ATCC accession no. PTA-5960, and clone 1F2 having ATCC accession no. PTA-5959.

2. An antibody which is a chimeric or humanized version of the mouse monoclonal antibody produced by a clone selected from the group consisting of clone 1D5 having ATCC accession no. PTA-5958, clone 2E1 having ATCC accession no. PTA-5961, clone 2H9 having ATCC accession no. PTA-5962, clone 2D11 having ATCC accession no. PTA-5960, and clone 1F2 having ATCC accession no. PTA-5959, or antigen-binding fragment thereof.

3. The antibody of claim 2 which is a F(ab')$_2$ fragment.

4. The antibody of claim 2 which is a F(ab') fragment.

5. The antibody of claim 2 which is conjugated to a therapeutic agent.

6. The antibody of claim 5, wherein the therapeutic agent is a cytotoxin.

7. The antibody of claim 6 wherein said cytotoxin is paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, a glucocorticoids, procaine, tetracaine, lidocaine, propranolol, puromycin, epirubicin, or cyclophosphamide.

8. The antibody of claim 2 comprising at least one modification in the Fc region.

9. A pharmaceutical composition comprising (i) a therapeutically effective amount of an antibody which is a chimeric or humanized version of the mouse monoclonal antibody produced by a clone selected from the group consisting of clone 1D5 having ATCC accession no. PTA-5958, clone 2E1 having ATCC accession no. PTA-5961, clone 2H9 having ATCC accession no. PTA-5962, clone 2D11 having ATCC accession no. PTA-5960, and clone 1F2 having ATCC accession no. PTA-5959, or an antigen-binding fragment thereof, and (ii) a pharmaceutically acceptable carrier.

10. The pharmaceutical composition of claim 9, wherein said antibody is a chimeric version, or antigen-binding fragment thereof.

11. The pharmaceutical composition of claim 9, wherein said antibody is a humanized version, or antigen-binding fragment thereof.

12. The pharmaceutical composition of claim 9, wherein said antibody is a F(ab')$_2$ fragment.

13. The pharmaceutical composition of claim 9, wherein said antibody is a F(ab') fragment.

14. The antibody of claim 2, wherein said antibody is a chimeric version, or antigen-binding fragment thereof.

15. The antibody of claim 2, wherein said antibody is a humanized version, or antigen-binding fragment thereof.

* * * * *

SEQUENCE LISTING

<160> NUMBER OF SEQ ID NOS: 4

<210> SEQ ID NO 1
<211> LENGTH: 363
<212> TYPE: DNA
<213> ORGANISM: Homo sapiens

<400> SEQUENCE: 1

```
caggtccaat tgcagcagcc tgtgactgag ctggtgaggc cggggggcttc agtgatgttg      60 tcctgcaagg cttctgacta ccccttcacc aactactgga tacactgggt aaagcagagg     120
cctggacaag gcctggagtg gatcggagtg attgatcctt ctgatactta tccaaattac     180
aataaaaagt tcaagggcaa ggccacattg actgtagtcg tatcctccag cacagcctac     240
atgcagctca gcagcctgac atctgacgat tctgcggtct attactgtgc aagaaacggt     300
gattccgatt attactctgg tatggactac tggggtcaag gaacctcagt caccgtctcc     360
tca                                                                   363
```

<210> SEQ ID NO 2
<211> LENGTH: 121
<212> TYPE: PRT
<213> ORGANISM: Homo sapiens

<400> SEQUENCE: 2

```
Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Lys Ala Thr Leu Thr Val Val Ser Ser Ser Thr Ala Tyr
65                  70                  75                  80

Met Gln Leu Ser Ser Leu Thr Ser Asp Asp Ser Ala Val Tyr Tyr Cys
            85                  90                  95

Ala Arg Asn Gly Asp Ser Asp Tyr Tyr Ser Gly Met Asp Tyr Trp Gly
            100                 105                 110
```

```
Gln Gly Thr Ser Val Thr Val Ser Ser
        115                 120

<210> SEQ ID NO 3
<211> LENGTH: 321
<212> TYPE: DNA
<213> ORGANISM: Homo sapiens

<400> SEQUENCE: 3
gacatcttgc tgactcagtc tccagccatc ctgtctgtga gtccaggaga gagagtcagt      60
ttttcctgca ggaccagtca gagcattggc acaaacatac actggtatca gcaaagaaca     120
aatggttttc caaggcttct cataaagaat gtttctgagt ctatctctgg gatcccttcc     180
aggtttagtg gcagtggatc agggacagat tttattctta gcatcaacag tgtggagtct     240
gaagatattg cagattatta ttgtcaacaa agtaatacct ggccgttcac gttcggaggg     300
gggaccaagc tggaaataaa a                                                321

<210> SEQ ID NO 4
<211> LENGTH: 107
<212> TYPE: PRT
<213> ORGANISM: Homo sapiens

<400> SEQUENCE: 4

Asp Ile Leu Leu Thr Gln Ser Pro Ala Ile Leu Ser Val Ser Pro Gly
1               5                   10                  15

Glu Arg Val Ser Phe Ser Cys Arg Thr Ser Gln Ser Ile Gly Thr Asn
            20                  25                  30

Ile His Trp Tyr Gln Gln Arg Thr Asn Gly Phe Pro Arg Leu Leu Ile
        35                  40                  45

Lys Asn Val Ser Glu Ser Ile Ser Gly Ile Pro Ser Arg Phe Ser Gly
    50                  55                  60

Ser Gly Ser Gly Thr Asp Phe Ile Leu Ser Ile Asn Ser Val Glu Ser
65                  70                  75                  80

Glu Asp Ile Ala Asp Tyr Tyr Cys Gln Gln Ser Asn Thr Trp Pro Phe
                85                  90                  95

Thr Phe Gly Gly Gly Thr Lys Leu Glu Ile Lys
            100                 105
```